United States Patent
Dawson et al.

(10) Patent No.: US 7,053,071 B2
(45) Date of Patent: May 30, 2006

(54) INDUCTION OF APOPTOSIS IN CANCER CELLS

(75) Inventors: Marcia Dawson, Los Altos, CA (US); Joseph A. Fontana, West Bloomfield, MI (US); Xiao-kun Zhang, San Diego, CA (US); Mark Leid, Corvallis, OR (US); Ling Jong, Sunnyvale, CA (US); Peter D. Hobbs, Moss Beach, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 10/308,241

(22) Filed: Dec. 2, 2002

(65) Prior Publication Data

US 2003/0176506 A1 Sep. 18, 2003

Related U.S. Application Data

(60) Provisional application No. 60/406,252, filed on Aug. 26, 2002, provisional application No. 60/334,081, filed on Nov. 30, 2001.

(51) Int. Cl.

| | |
|---|---|
| *A01N 57/00* | (2006.01) |
| *A01N 57/10* | (2006.01) |
| *A01N 43/40* | (2006.01) |
| *A01N 43/78* | (2006.01) |
| *A01N 43/80* | (2006.01) |
| *A01N 41/02* | (2006.01) |
| *A01N 53/00* | (2006.01) |
| *A61K 31/675* | (2006.01) |
| *A61K 31/66* | (2006.01) |
| *A61K 31/54* | (2006.01) |
| *A61K 31/535* | (2006.01) |
| *A61K 31/445* | (2006.01) |
| *A61K 31/425* | (2006.01) |
| *A61K 31/42* | (2006.01) |
| *A61K 31/255* | (2006.01) |

(52) U.S. Cl. .......... 514/92; 514/148; 514/227.5; 514/237.5; 514/325; 514/369; 514/381; 514/517; 514/531; 514/532; 514/538; 514/563; 514/575; 514/577; 514/621; 514/623; 514/624; 544/59; 544/154; 546/203; 548/183; 548/252; 558/44; 558/51; 558/58; 558/177; 564/161; 564/170; 564/171; 564/176

(58) Field of Classification Search .......... 560/100, 560/104, 59, 62; 562/467, 478, 23, 25, 41, 562/74, 83, 87, 88, 466, 474, 475, 492; 564/170, 564/171, 176; 558/44, 51, 58, 177; 548/183, 548/252

See application file for complete search history.

(56) References Cited

U.S. PATENT DOCUMENTS 4,680,299 A * 7/1987 Hesson .......... 514/311

(Continued)

FOREIGN PATENT DOCUMENTS

EP 0947496 10/1999

(Continued)

OTHER PUBLICATIONS

Hawley's Condensed Chemical Dictionary, 12th ed., Richard J. Lewis, Sr., © 1993 by Van Nostrand Reinhold, p. 594.*

(Continued)

*Primary Examiner*—James O. Wilson
*Assistant Examiner*—Zachary C. Tucker
(74) *Attorney, Agent, or Firm*—Schwegman, Lundberg, Woessner & Kluth, P.A.

(57) ABSTRACT

The present invention provides compounds that are inducers or inhibitors of apoptosis or apoptosis preceded by cell-cycle arrest. In addition, the present invention provides pharmaceutical compositions and methods for treating mammals with leukemia or other forms of cancer or for treating disease conditions caused by apoptosis of cells.

24 Claims, 25 Drawing Sheets

4-[3-(1-Adamantyl)-4-hydroxyphenyl]-3-chlorocinnamic, acid (3-Cl-AHPC)

6-[3-(1-Adamantyl)-4-hydroxyphenyl]-2-naphthalenecarboxylic acid, (AHPN)

U.S. PATENT DOCUMENTS

| | | | | |
|---|---|---|---|---|
| 6,127,415 | A | 10/2000 | Pfahl et al. | 514/543 |
| 6,462,064 | B1 | 10/2002 | Pfahl et al. | 514/394 |
| 6,515,003 | B1 | 2/2003 | Pfahl et al. | 514/369 |
| 6,627,656 | B1 * | 9/2003 | Gallant et al. | 514/506 |
| 2002/0143182 | A1 | 10/2002 | Pfahl et al. | 546/14 |

FOREIGN PATENT DOCUMENTS

| | | | |
|---|---|---|---|
| JP | 10-20514 | * | 1/1998 |
| WO | WO 97/32853 | * | 9/1997 |
| WO | WO-98/01132 | | 1/1998 |
| WO | WO 01/36365 A2 | * | 5/2001 |
| WO | WO-01/56563 | | 8/2001 |
| WO | WO-03/011808 | | 2/2003 |

OTHER PUBLICATIONS

Concise Chemical Dictionary, edited by Drs. Hans-Dieter Jakubke and Hans Jeschkeit, © 1993 by Walter de Gruyter & Co., p. 490.*

McGraw-Hill Dictionary of Chemical Terms, 3rd ed. edited by Sybil P. Parker, © 1984 McGraw-Hill, Inc., p. 200.*

U.S. Appl. No. 60/199,299 (Gallant et al), filed Apr. 24, 2000.*

Benincori et al, "Rearrangements of Aromatic Carbonyl Arylhydrazones of Benzene, Naphthalene, and Azulene" J. Chem. Soc. Perking Transactions I., vol. 10, pp. 2721-2728 (1988).*

Brunow and Ilus, "Reaction of 2,6-di-tert-butyl-4-propionylphenoxy radicals with ethyl ferulate" Tetrahedron Letters, vol. 10, pp. 711-712 (1970). AS ABSTRACTED BY CAPLUS.*

Garcia-Conesa et al, "Ferulic acid dehydrodimers from wheat bran: isolation, purification and antioxidant properties of 8-O-4-diferulic acid" Redox Report, vol. 3(5/6) pp. 319-323 (1997). AS ABSTRACTED BY CAPLUS.*

Aravind, L., et al., "Apoptotic Molecular Machinery: Vastly Increased Complexity in Vertebrates Revealed by Genome Comparisons", *Science Magazine, 291*, (Feb. 2001), 1279-1284.

Bennett, John M., et al., "Proposed Revised Criteria for the Classification of Acute Myeloid Leukemia", *Annals of Internal Medicine, 103*, (1985),626-629.

Berman, Ellin, "Recent Advances in the Treatment of Acute Leukemia: 1999", *Current Opinions in Hematology, 4*,(2000),205-211.

Bernard, Bruno A., et al., "Identification of Synthetic Retinoids with Selectivity for Human Nuclear Retinoic Acid Receptor", *Biochemical and Biophysical Research Communications, 186*, (1992),977-983.

Boise, Lawrence H., et al., "bcl-x, a bcl-2-Related Gene That Functions as a Dominant Regulator of Apoptotic Cell Death", *Cell, 74*, (1993),597-608.

Bradner, William T., et al., "Myeloid Leukemia C1498 as a Screen for Cancer Chemotherapeutic Agents", *Cancer Research, 26*, (1966),375-390.

Breitman, T. R., et al., "Terminal Differentiation of Human Promyelocytic Leukemic Cells in Primary Culture in Response to Retinoic Acid", *Blood, 57, 6*, (1981),1000-1004.

Bruserud, Oystein, et al., "New Strategies for the Treatment of Acute Myelogenous Leukemia: Differentiation Induction-Present Use and Future Possibilities", *Stem Cells, 18*, (2000),57-165.

Bruserud, Oystein, et al., "New Strategies in the Treatment of Acute Myelogenous Leukemia: Mobilization and Transplantation of Autologous Peripherial Blood Stem Cells in Adult Patients", *Stem Cells, 18*, (2000),343-351.

Castaigne, Sylvie, et al., "All-Trans Retinoic Acid as a Differentiation Therapy for Acute Promyelocytic Leukemia. I. Clinical Results", *Blood, 76, 9*, (Nov. 1990),1704-1709.

Chao, W. R., et al., "Effects of Receptor Class- and Subtype-Selective Retinoids and an Apoptosis-Inducing Retinoid on the Adherent Growth of the NIH:OVCAR-3 Ovarian Cancer Cell Line in Culture", *Cancer Letters, 115*, (1997),1-7.

Chen, Zi-Xing, et al., "A Clinical and Experimental Study on All-Trans Retinoic Acid-Treated Acute Promyelocytic Leukemia Patients", *Blood, 78, 6*,(1991),1413-1419.

Corbett, Thomas H., et al., "Preclinical Efficacy of Thioxanthone SR271425 Against Transplanted Solid Tumors of Mouse and Human Origin", *In: Investigational New Drugs, 17*, Kluwer Academic Publishers, Netherlands,(1999),7-27.

Corbett, Thomas, et al., "Tumor Models and the Discovery and Secondary Evaluation of Solid Tumor Active Agents", *International Journal of Pharmacognosy, 33*, (1995),102-122.

Davis, Roger J., "Signal Transduction by the JNK Group of MAP Kinases", *Cell, 103*, (2000),239-252.

Franklin, R. A., et al., "Kinases: Positive and Negative Regulators of Apoptosis", *Leukemia, 14*, (2000),2019-2034.

Fujita, Naoya, et al., "Acceleration of Apoptotic Cell Death after the Cleavage of Bcl-X(L) Protein by Caspase-3-like Proteases", *Oncogene, 17*, (1998),1295-1304.

Gavrieli, Y., "Identification of Programmed Cell Death In Situ via Specific Labeling of Nuclear DNA Fragmentation", *The Journal of Cell Biology, 119 (3)*, (Nov. 1992),pp. 493-501.

Gross, Atan, et al., "BCL-2 Family Members and the Mitochondria in Apoptosis", *Genes and Development, 13*, (1999),1899-1911.

Hanada, Motoi, et al., "bcl-2 Gene Hypomethylation and High-Level Expression in B-Cell Chronic Lymphocytic Leukemia", *Blood, 82, 6*, (1993),1820-1828.

Hsu, C. A., et al., "Retinoid Induced Apoptosis in Leukemia Cells Through a Retinoic Acid Nuclear Receptor-Independent Pathway", *Blood, 89, 12*, (1997),4470-4479.

Jarpe, Matthew B., et al., "Anti-apoptotic Versus Pro-apoptotic Signal Transduction: Checkpoints and stop signs along the road to death", *Oncogene, 17*, (1998),1475-1482.

Lazebnik, Y. A., et al., "Cleavage of poly(ADP-ribose) polymerase by a proteinase with properties like ICE", *Nature, 371*, (Sep. 1994),346-347.

Parchment, Ralph E., et al., "In Vivo-In Vitro Correlation of Myelotoxicity of 9-Methoxypyrazoloacridine (NSC-366140, PD115934) to Myeloid and Erythroid Hematopoietic Progenitors From Human, Murine, and Canine Marrow", *Journal of the National Cancer Institute, 86, 4*, (Feb. 1994),273-280.

Saez, Ruben A., "Therapeutic Options in the Management of Acute Myelogenous Leukemia in Adults", *Cancer Control Journal of the Moffitt Cancer Center, 4, 5*, (1997),13 pgs.

Shao, Zhi-Ming, et al., "p53 Independent G(0)/G(1) Arrest and Apoptosis Induced by a Novel Retinoid in Human Breast Cancer Cells", *Oncogene, 11*, (1995),493-504.

Sharpless, T., et al., "Flow Cytofluorimetry: Discrimination Between Single Cells and Cell Aggregates by Direct Size Measurements", *Acta Cytologica, 19, 6*, (1975),577-581.

Sheikh, M. S., et al., "Mechanisms of Regulation of WAF1/Cip1 Gene Expression in Human Breast Carcinoma: Role of p53-dependent and Independent Signal Transduction Pathways", *Oncogene, 9*, (1994),3407-3415.

Stein, A. S., et al., "High-dose Cytosine Arabinoside and Daunorubicin Induction Therapy for Adult Patients with de novo Non M3 Acute Myelogenous Leukemia: Impact of Cytogenetics on Achieving a Complete Remission", *Leukemia, 14*, (2000),1191-1196.

Teicher, Beverly A., "In Vivo Tumor Response End Points", *In: Tumor Models in Cancer Research*, B. A. Teicher, ed., Humana Press, Totowa, New Jersey,(2002),593-616.

Thacker, J. D., et al., "Cytokine-Dependent Engraftment of Human Myeloid Leukemic Cell Lines in Immunosuppressed Nude Mice", *Leukemia, 8, 5*, (1994),871-877.

Thomas, Anju, et al., "Drug-induced Apoptosis in B-cell Chronic Lymphocytic Leukemia: Relationship Between p53 Gene Mutation and bcl-2/bax Proteins in Drug Resistance", *Oncogene, 12*, (1996),1055-1062.

Tournier, Cathy, et al., "Requirement of JNK for Stress-Induced Activation of the Cytochrome c-Mediated Death Pathway", *Science, 288*, (2000),870-874.

Vaux, D. L., et al., "The Molecular Biology of Apoptosis", *Proceedings of the National Academy of Science, 93*, (1996),2239-2244.

Wang, Xiantao, et al., "Requirement for ERK Activation in Cisplatin-induced Apoptosis", *The Journal of Biological Chemistry, 275, 50*, (2000),39435-39443.

Warrell, Raymond P., et al., "Differentiation Therapy of Acute Promyelocytic Leukemia with Tretinoin (All-Trans-Retinoic Acid)", *The New England Journal of Medicine, 324, 20*, (1991),1385-1393.

Whitacre, Cecilia M., et al., "Involvement of NAD-Poly(ADP-Ribose) Metabolism in p53 Regulation and Its Consequences", *Cancer Research, 55*, (Sep. 1995),3697-3701.

Widmann, Christian, et al., "Caspase-dependent Cleavage of Signaling Proteins during Apoptosis", *The Journal of Biological Chemistry, 273, 12*, (1998),7141-7147.

Wolf, Beni B., et al., "Suicidal Tendencies: Apoptotic Cell Death by Caspase Family Proteinases", *The Journal of Biological Chemistry, 274, 29*, (1999),20049-20052.

Woo, Minna, et al., "Essential Contribution of Caspase 3/CPP32 to Apoptosis and its Associated Nuclear Changes", *Genes and Development, 12*, (1998),806-819.

Zhang, Yuxiang, et al., "Induction of Apoptosis of Human B-CLL and ALL Cells by a Novel Retinoid and its Nonretinoidal Analog", *Blood, 100, 8*, (2002),2917-2925.

Zhou, Ping, et al., "Mcl-1, a Bcl-2 Family Member, Delays the Death of Hematopoietic Cells Under a Variety of Apoptosis-Inducing Conditions", *Blood, 82, 2*, (Jan. 1997),630-643.

Charpentier, B., et al., "Synthesis, Structure-Affinity Relationships, and Biological Activities of Ligands Binding to Retinoic Acid Receptor Subtypes", *J. Med. Chem., 38*, (1995),4993-5006.

Diaz, P., et al. "Synthesis and Biological Activities of New Heterocyclic Aromatic Retinoids", *Bioorganic and Medicinal Chemistry Letters, 7*, (1997),2289-2294.

Cook, J. W., et al., "Colchicine and Related Compounds. Part IX", *Journal of the American Chemical Society*, (1950),139-147.

Dawson, M. I., et al., "Apoptosis Induction in Cancer Cells by a Novel Analogue of 6-[3-(1-Adamantyl)-4-hydroxyphenyl]-2-naphthalenecarboxylic Acid Lacking Retinoid Receptor Transcriptional Activation Activity", *Cancer Research, 61*, (Jun. 15, 2001),4723-4730.

Dawson, M. I., et al., "Effects of Trans-retinoic Acid, 9-cis-retinoic Acid, 1alpha,25-(dihydroxy)vitamin D3 and a Novel Apoptosis-inducing Retinoid on Breast Cancer and Endothelial Cell Growth", *Cancer Letters, 133*, (1998),1-8.

El-Feraly, F. S., "Randainol: A Neolignan from Sassafras radndaiense", *Phytochemistry, 23*, (1984),2329-2331.

Fontana, Joseph A., et al., "Identification of a Unique Binding Protein Specific for a Novel Retinoid Inducing Cellular Apoptosis", *Int. J. of Cancer, 86*, (2000),474-479.

Hail, Numsen, Jr., et al., "Evidence Supporting a Role for Mitochondrial Respiration in Apoptosis Induction by the Synthetic Retinoid CD437", *Cancer Research, 61*, (2001),6698-6702.

Hail, Jr., Numsen, et al., "Synthetic Retinoid CD437 Promotes Rapid Apoptosis in Malignant Human Epidermal Keratinocytes and G1 Arrest in Their Normal Counterparts", *Journal of Cellular Physiology, 186*, (2001),24-34.

Holmes, William F., et al., "Induction of Apoptosis in Ovarian Carcinoma Cells by AHPN/CD437 Is Mediated by Retinoic Acid Receptors", *Journal of Cellular Physiology, 185*, (2000),61-67.

Joshi, K. C., et al., "Synthesis of Some Fluorine Containing Indoles and Related Compounds", *J. F. Prakt. Chem., 320*, (1978),701-704.

Kumar, Atul, et al., "Cross-Resistance to the Synthetic Retinoid CD437 in a Paclitaxel-Resistant Human Ovarian Carcinoma Cell Line Is Independent of the Overexpression of Retinoic Acid Receptor-γ1", *Cancer Research, 61*, (Oct. 15, 2001),7552-7555.

Marchetti, Philippe, et al., "The Novel Retinoid 6-[3-(1-adamantyl)-4-hydroxyphenyl]-2-naphthalene Carboxylic Acid Can Trigger Apoptosis Through a Mitochondrial Pathway Independent of the Nucleus", *Cancer Research, 59*, (Dec. 15, 1999),6257-6266.

Schadendorf, D., et al., "Retinoic Acid Receptor-gamma-selective Retinoids Exert Antiproliferative Effects on Human Melanoma Cell Growth in Vitro", *International Journal of Oncology, 5*, (1994),1325-1331.

Sun, Shi-Yong, et al., "Dual Mechanisms of Action of the Retinoid CD437: Nuclear Retinoic Acid Receptor-Mediated Suppression of Squamous Differentiation and Receptor-Independent Induction of Apoptosis in UMSCC22B Human Head and Neck Squamous Cell Carcinoma Cells", *Molecular Pharmacology, 58, 3*, (2000),508-514.

Sun, Shi-Yong, et al., "Mechanisms of Apoptosis Induced by the Synthetic Retinoid CD437 in Human Non-Small Cell Lung Carcinoma Cells", *Oncogene, 18*, (1999),2357-2365.

Zhao, X., et al., "Retinoic Acid Receptor-Independent Mechanism of Apoptosis of Melanoma Cells by the Retinoid CD437 (AHPN)", *Cell Death and Differentiation, 8*, (2001),878-886.

Farhana, L., et al., "Apoptosis signaling by the novel compound 3-Cl-AHPC involves increased EGFR proteolysis and accompanying decreased phosphatidylinositol 3-kinase and AKT kinase activities", *Oncogene*, (2004),pp. 1-11.

Zhang, Y., et al., "Induction of apoptosis in retinoid-refractory acute myelogenous leukemia by a novel AHPN analog", *Blood, 102(10)*, (2003),pp. 3743-3752.

* cited by examiner

4-[3-(1-Adamantyl)-4-hydroxyphenyl]-3-chlorocinnamic, acid (3-Cl-AHPC)

6-[3-(1-Adamantyl)-4-hydroxyphenyl]-2-naphthalenecarboxylic acid, (AHPN)

*MO7e*

*Pt. 1*

*Pt. 1*

Pt. 2

Pt. 1

INDUCTION OF APOPTOSIS IN CANCER CELLS

CROSS-REFERENCE TO RELATED APPLICATION

This application claims priority from U.S. Provisional Patent Application No. 60/334,081, filed, Nov. 30, 2001, and U.S. Provisional Patent Application No. 60/406,252, filed, Aug. 26, 2002, which are incorporated herein by reference.

STATEMENT OF GOVERNMENT RIGHTS

This invention was made with government support under grant number CA51993 awarded by the National Institutes of Health. The United States Government has certain rights in this invention.

BACKGROUND OF THE INVENTION

Acute myelogenous leukemia (AML) is a heterogeneous disease composed of numerous sub-classifications displaying a wide spectrum of phenotypes. (See Berman, E., Curr. Opin. Hematol., 4: 205–11 (1999) and Bruservd, O. et al., Stem Cells, 18: 157–65 (2000).) The major therapeutic approach to this disease has been the use of chemotherapeutic agents with associated life-threatening toxicity. Although non-specific in their effects, these regimens have significantly increased the survival of AML patients. (See Saez, R. A., Cancer Control, 4: 399–406 (1997); Bruservd, O. et al., Stem Cells, 18: 343–351 (2000); and Stein, A. S. et al., Leukemia, 14: 1191–1196 (2000).) Recently, more targeted therapy has been developed. Treatment of acute promyelocytic leukemia (APL) patients with trans-retinoic acid (tRA) results in the differentiation of the cells with 90 percent of the patients achieving a complete remission. (See Chen, Z. X. et al., Blood, 78: 1413–1419 (1991); Castaigne, S. et al., Blood, 76: 1704–1709 (1990); and Warrell, R. P. et al., N. Engl. J. Med., 324: 1385–1393 (1991). tRA exerts its effect by modulating gene expression through its role as a ligand to the retinoic acid nuclear receptors (RARs) with the subsequent binding of this complex to the RARE consensus sequences located in the regulatory regions of retinoid-responsive genes. The selective sensitivity of APL cells to tRA-mediated differentiation resides in their specific expression of a unique PML-RARα fusion product with subsequent maturation arrest of these cells at the promyelocyte stage; exposure of these cells to a micromolar concentration of tRA allows for the degradation of the PML-RARα fusion product and restitution of normal RARα receptor function with subsequent maturation of the APL cells.

Z. M. Shao et al.(1995) have recently shown that the retinoid 6-[3-(1-adamantyl)-4-hydroxyphenyl]-2-naphthalenecarboxylic acid (AHPN) is a potent inducer of apoptosis in a number of cell types. Both natural and synthetic retinoids exert their biological action through their binding to and activation of specific RARs and retinoic acid X nuclear receptors (RXRs). These receptors complexed with ligand and bound to specific regions in the promoters of genes designated as retinoid response elements (RAREs and RXREs) modulate gene expression. AHPN does not bind to the RXRs, is an extremely poor binder and transactivator of the RAR subtype α, but at 1 μM binds and transactivates RARβ and RARγ. Whether AHPN induces apoptosis through activation of these receptors is still controversial. AHPN exposure results in apoptosis of the human leukemia cell line HL-60R, which lacks functional RARs, and the cell line K562, which is resistant to the antiproliferative actions of tRA. These results suggest that AHPN induces cell death at least in myeloid leukemia cells through a novel pathway that does not involve its direct interaction with the retinoid receptors. AHPN also causes the rapid activation of the MAPK kinase pathway by inducing the activation of the p38 and JNK kinases within 1 hour. Activation of these kinases is not observed following exposure of the cells to standard retinoids that function through classical RAR/RXR-signaling pathways. JNK activation has been implicated as a major player in the induction of apoptosis by a number of agents and has recently been shown to result in p53 activation and subsequent p53-mediated-apoptosis in sympathetic neurons.

The ability of AHPN to induce apoptosis in the cell line ALL-REH, which was obtained from a patient with acute lymphocytic leukemia, was examined. AHPN treatment lead to stimulation of caspase 3 activity, which, in turn, resulted in the generation of a unique Bcl-$X_L$ cleavage product that promotes apoptosis. AHPN induced apoptosis in ALL cells obtained from patients. Unfortunately, the concentrations of AHPN required to induce leukemia cell apoptosis in a cell culture produced adverse side effects when administered to mice. These results strongly suggest similar toxicity when administered to humans.

Therefore, a continuing need exists for compounds that are more useful inducers, or inhibitors, of apoptosis or apoptosis preceded by cell-cycle arrest. In addition, there is a need for pharmaceutical compositions and methods for treating mammals with leukemia or other forms of cancer or for treating disease conditions caused by apoptosis of cells.

SUMMARY OF THE INVENTION

The present invention provides compounds that are useful inducers or inhibitors of apoptosis or apoptosis preceded by cell-cycle arrest. The compounds of the invention have formula (I)

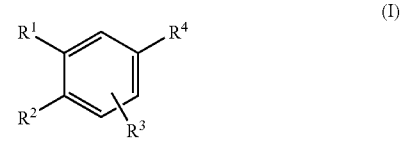

wherein $R^1$ is $C_{1-10}$alkyl, $C_{2-10}$alkenyl, $C_{2-10}$alkynyl, halo, halo$C_{1-10}$alkyl, $C_{1-10}$alkoxy, ($C_{1-10}$alkyl)mercapto, amino, ($C_{1-10}$alkyl)NH—, ($C_{1-10}$alkyl)$_2$N—, $C_{3-8}$cycloalkyl, $C_{3-8}$cycloalkenyl, $C_{6-30}$polycycloalkyl, $C_{6-30}$polycycloalkenyl, $C_{3-8}$heterocycloalkyl, $C_{6-30}$polyheterocycloalkyl, $C_{3-8}$heterocycloalkenyl, $C_{3-30}$polyheterocycloalkenyl, aryl, heteroaryl, ($C_{1-10}$alkyl)-C(O)—, ($C_{3-8}$cyclo-alkyl)-C(O)—, ($C_{3-8}$cycloalkenyl)-C(O)—, ($C_{3-8}$heterocycloalkyl)-C(O)—, or ($C_{3-8}$heterocycloalkenyl)-C(O)—; wherein the cyclic $R_1$ groups are optionally substituted with alkyl groups.

$R^2$ is hydrogen, hydroxy, —SH, amino, —CN, ($C_{1-10}$alkyl)NH—, ($C_{1-10}$alkyl)$_2$N—, —COOR$^{14}$, —C(=O)R$^{14}$, —C(=O)N(R$^{14}$)$_2$, —N(R$^{14}$)C(=O)R$^{14}$, —P(O)(OR$_{14}$)$_2$ (phosphonic acid), —S(O)$_2$OR$^{14}$ (sulfonic acid), —S(O)$_2$N(R$^{14}$)$_2$ (sulfonamide), —N—C(NH)—N(R$^{15}$)$_2$ (guanidino), (hydroxy)$C_{1-10}$alkylene-, ($C_{1-10}$alkyl)-C(O)—, —C(O)-NHOR$^{14}$ (hydroxamic acid), or oxime;

$R^3$ is hydrogen, $C_{1-10}$alkyl, hydroxy, amino, ($C_{1-10}$alkyl)NH—, ($C_{1-10}$alkyl)$_2$N—, —COOR$^{14}$ (carboxylic acid), —P(O)(OR$_{14}$)$_2$ (phosphonic acid), —S(O)$_2$OR$^{14}$ (sulfonic acid), —S(O)₂N(R¹⁴)₂ (sulfonamide), —N═C(NH)—N (R¹⁵)₂ (guanidino), (hydroxy)C$_{1-10}$alkylene, (C$_{1-10}$alkyl)-C(O)—, —C(O)—NHOR¹⁴ (hydroxamic acid), carbonyl oxime, fluoro, chloro, bromo, iodo, —CF₃ or nitro.

R¹ and R³ taken together with the ring to which they are attached can form a polycyclic group. The polycyclic group can be fully saturated or aromatic or partially saturated or partially aromatic.

R⁴ is

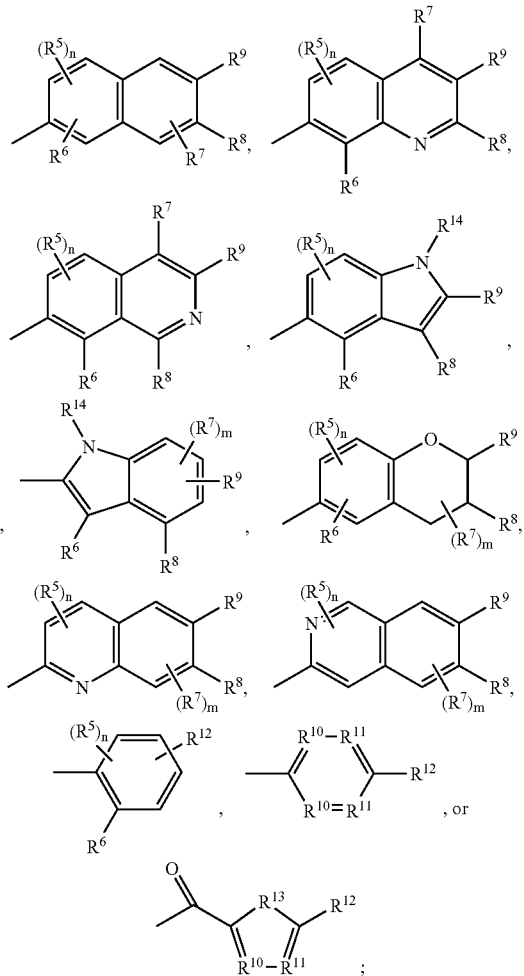

wherein each R⁵ group is independently hydroxy, C$_{1-10}$alkyl, C$_{1-10}$alkoxy, amino, (C$_{1-10}$alkyl)NH—, (C$_{1-10}$alkyl)₂N—, (amino)C$_{1-10}$alkyleneoxy)-, (acetamido)alkoxy, (C$_{1-10}$alkyl) mercapto, (hydroxy)C$_{1-10}$alkylene-, halo, halo(C$_{1-10}$ alkyl, (C$_{1-10}$alkoxy)C$_{1-10}$alkylene-, nitro, acetamido, phenyl, or substituted phenyl.

The R⁶, and R⁸ groups are independently hydrogen, hydroxy, C$_{1-10}$alkyl, C$_{1-10}$alkoxy, amino, (C$_{1-10}$alkyl)NH—, (C$_{1-10}$alkyl)₂N—, (amino)C$_{1-10}$alkyleneoxy)-, (acetamido) alkoxy, (C$_{1-10}$alkyl)mercapto, (hydroxy)C$_{1-10}$alkylene-, halo, halo(C$_{1-10}$)alkyl, (C$_{1-10}$alkoxy)C$_{1-10}$alkylene-, nitro, acetamido, phenyl, or substituted phenyl.

The R⁷ groups are independently hydroxy, C$_{1-10}$alkyl, C$_{1-10}$alkoxy, amino, (C$_{1-10}$alkyl)NH—, (C$_{1-10}$alkyl)₂N—, (amino)C$_{1-10}$alkyleneoxy)-, (acetamido)-alkoxy, (C$_{1-10}$alkyl)mercapto, (hydroxy)C$_{1-10}$alkylene-, halo, halo(C$_{1-10}$)alkyl, (C$_{1-10}$alkoxy)C$_{1-10}$alkylene-, nitro, aceta- mido, phenyl, or substituted phenyl, or two R⁷ groups or R⁷ and R⁸, attached to the same carbon atom can be oxo (═O).

R⁹ is —COOR¹⁴, —P(O)(OR¹⁴)₂, —S(O)₂OR¹⁴, —C(O)—NHOR¹⁴, thiazolidenedione, tropolone, tetrazole, nitro, —(CH₂)$_j$OR¹⁵, or —N═C(NH)—N(R¹⁵)₂;

R¹⁰ and R¹¹ are independently O, S, N, CH, or CR⁷; provided that when R¹⁰ or R¹¹ is O or S then the bonds attached to R¹⁰ or R¹¹ are single bonds.

R¹² is —C(R¹⁶)═C(R¹⁶)(R⁹), aryl-R⁹, or 2-cyclopropyl-R⁹, where each R¹⁶ is independently hydrogen or fluorine;

R¹³ is S, O, NH, N(C$_{1-10}$alkyl), or N(aryl);

R¹⁴ is hydrogen, (C$_{1-25}$)alkyl or aryl;

R¹⁵ is hydrogen, (C$_{1-10}$alkyl)-C(O)—, or (aryl)-C(O)—;

and j is from 1 to 10, n and m are independently 0, 1, 2, or 3.

wherein any alkyl, alkenyl, alkynyl, cycloalkyl, cycloalkenyl, polycycloalkyl, polycycloalkenyl, heterocycloalkyl, polyheterocycloalkyl, heterocycloalkenyl, polyheterocycloalkenyl, aryl, or heteroaryl group of R¹, R², R³, R⁵, R⁶, R⁷, and R⁸, is optionally substituted with one or more, such as 1, 2, 3, or 4, substituents independently selected from oxo (═O), halo, —OH, —CN, —NO₂, —CF₃, —OCF₃, —S(O)$_{0-2}$ C$_{1-6}$ alkyl, C$_{1-8}$alkyl, C$_{1-8}$alkoxy, C$_{1-8}$alkyl-NR$_a$R$_b$, phenyl, C$_{1-8}$alkanoyl, —NR$_a$R$_b$, —C(═O)NR$_a$R$_b$, or —SO₂NNR$_a$R$_b$;

wherein each R$_a$ and R$_b$ is independently hydrogen, C$_{1-6}$alkyl, C$_{1-6}$alkanoyl, C$_{1-6}$alkoxycarbonyl, aryl, (aryl)C$_{1-8}$alkylene-, arylcarbonyl, or aryloxycarbonyl; or R$_a$ and R$_b$ together with the nitrogen to which they are attached form a pyrrolidino, piperidino, morpholino, or thiomorpholino ring.

n and ma are independently 0, 1, 2, or 3.

The present invention also provides pharmaceutical salts of the compounds of formula (I).

The invention provides a compound of formula I for use in medical therapy (e.g., for use in inducing apoptosis, modulating caspase activity, inducing cell death, or treating cancer, preferably for use in treating lung cancer, breast cancer, prostate cancer, other forms of cancer, and leukemia, such as, for example, acute lymphocytic leukemia (ALL), acute myelogenous leukemia (AML), chronic myelogenous leukemia (CML), and other diseases of proliferation) as well as the use of a compound of formula I for the manufacture of a medicament for inducing apoptosis, modulating caspase activity, inducing cell death, or treating cancer, preferably for use in treating lung cancer, breast cancer, prostate cancer, CML, ALL, AML, other forms of cancer or leukemia, and other diseases of proliferation, in a mammal, such as a human. The compounds of the invention are also useful for treatment in diseases in which apoptosis, using the AHPN antagonist pathway, is one of the symptoms, such as, for example, heart conditions, Parkinson's disease, Alzheimer's disease and the like.

The invention also provides a method to induce apoptosis or death in a cell comprising contacting the cell, in vitro or in vivo, with an effective amount of a compound of the invention (as described herein).

The invention also provides a method to induce apoptosis in a mammal in need of such treatment comprising administering to the mammal, an effective amount of a compound of the invention (as described herein).

The invention also provides a method to activate a caspase (e.g., caspase 9 and/or 3) in a cell comprising contacting the cell, in vitro or in vivo, with an effective amount of a compound of the invention (as described herein).

The invention also provides a method for preventing or treating a pathological condition or symptom in a mammal, such as a human, associated with caspase (e.g., caspase 3) activation comprising administering to a mammal in need of such therapy, an effective caspase-modulating amount of a compound of the invention (as described herein).

The invention also provides a therapeutic method to induce cell death comprising contacting a cell, in vitro or in vivo, with an effective amount of a compound of the invention (as described herein).

The invention also provides a method to induce cell death in a mammal in need of such treatment comprising administering to the mammal, an effective amount of a compound of the invention (as described herein).

The invention also provides a method to treat cancer (e.g., lung cancer, breast cancer, prostate cancer, ALL, AML, solid tumors, other forms of cancer or leukemia, and other diseases of proliferation) in a mammal in need of such treatment comprising administering to the mammal, an effective amount of a compound of the invention (as described herein).

BRIEF DESCRIPTION OF THE FIGURES

FIG. 2 illustrates the 3-Cl-AHPC and tRA inhibition of growth and the induction of apoptosis in the M07e cell line. M07e cells were seeded in RPMI 1640 supplemented with 5% FBS, incubated overnight and varying concentrations of 3-Cl-AHPC or tRA added and the cells harvested at various times.

FIG. 6 illustrates 3-Cl-AHPC-mediated caspase activation. M07e and leukemic cells (patient 1) were treated with 3-Cl-AHPC or vehicle alone and caspase activation assessed as described in Materials and Methods.

DETAILED DESCRIPTION

Figure 1A:
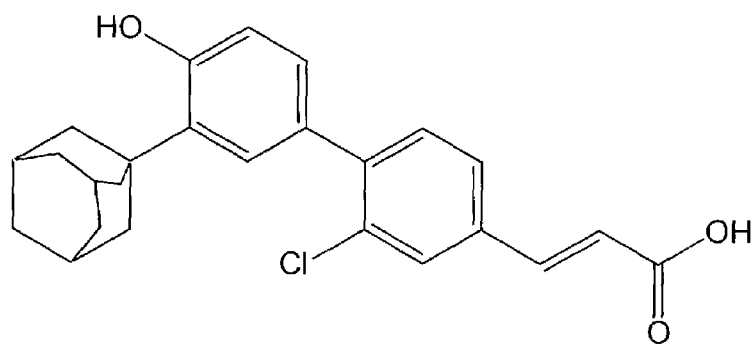
FIG. 1 illustrates the structures of the compounds AHPN and 3-Cl-AHPC.

The following definitions are used, unless otherwise described: halo is fluoro, chloro, bromo, or iodo. Alkyl, alkoxy, alkenyl, alkynyl, etc. denote both straight and branched groups; but reference to an individual group such as "propyl" embraces only the straight chain group, a branched chain isomer such as "isopropyl" being specifically referred to. Aryl denotes a phenyl group or an ortho-fused bicyclic carbocyclic group having about nine to ten ring atoms in which at least one ring is aromatic. Heteroaryl encompasses a group attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$–$C_4$) alkyl, phenyl or benzyl, as well as a group of an ortho-fused bicyclic-heterocycle of about eight to ten ring atoms derived therefrom, particularly a benz-derivative or one derived by fusing a propylene, trimethylene, or tetramethylene digroup thereto.

Specifically, the term "alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain one to 15 carbon atoms, such as, for example, (triethyl) methyl, t-methyl-2-butyl and the like.

As used herein the term "lower alkyl" refers to an alkyl group of 1 to 12 carbon atoms, preferably one to 10 carbon atoms.

As used herein the term "cycloalkyl" refers to a cyclic alkyl group of three to eight, preferably three, five or six, carbon atoms. The term "polycycloalkyl" refers to a cycloalkyl group of 6 to 30 carbon atoms having more than 1, i.e., at least two, rings. The term "cycloalkenyl" refers to a cycloalkyl group of three to eight, preferably five or six, carbon atoms having at least one double bond. The term "polycycloalkenyl" refers to a cycloalkyl group of 6 to 30 carbon atoms having at least one double bond and having more than 1, i.e., at least two, rings. Specific polycycloalkyl or polycycloalkenyl substituents include bicycloalkyl and bicycloalkenyl groups such as, for example, bicyclooctyl or bicyclooctenyl, and the like; tricycloalkyl and tricycloalkenyl groups such as, for example, adamantyl, bicyclo[2.2.2] octane, bicyclo[2.2.2]oct-2-ene and the like.

As used herein the term "heterocycloalkyl" refers to a cycloalkyl group wherein one or more carbon atoms is replaced with a heteroatom such as nitrogen, oxygen, and sulfur. The term "polyheterocycloalkyl" refers to a polycycloalkyl group wherein one or more carbon atoms is replaced with a heteroatom such as nitrogen, oxygen, and sulfur, and having more than 1, i.e., at least two rings. The term "heterocycloalkenyl" refers to a polycycloalkyl group wherein one or more carbon atoms is replaced with a heteroatom such as nitrogen, oxygen, and sulfur and having at least one double bond. The term "polyheterocycloalkenyl" refers to a polycycloalkyl group wherein one or more carbon atoms is replaced with a heteroatom such as nitrogen, oxygen, and sulfur and having at least one double bond and having more than 1, i.e., at least two, rings. Specific heteropolycycloalkyl or heteropolycycloalkenyl substituents include heterbicycloalkyl and heterobicycloalkenyl groups, such as, for example, aza-bicyclooctyl or aza-bicyclooctenyl, and the like.

The term "alkoxy" as used herein refers to an alkyl group bound through a single, terminal ether linkage, i.e., an "alkoxy" group may be defined as —OR where R is alkyl as defined above. A "lower alkoxy" group refers to an alkoxy group containing 1 to 12, more preferably 1 to 10, carbon atoms. The term "alkylmercapto" as used therein similarly intends an alkyl group bound through a single, terminal thioether linkage.

The terms "alkylamino" and "dialkylamino" refer to a terminal amine group having one and two alkyl groups, respectively.

The term "alkylene" as used herein refers to a divalent saturated branched or unbranched hydrocarbon chain containing from 1 to 24 carbon atoms, and includes, for example, methylene (—$CH_2$—), ethylene (—$CH_2CH_2$—), propylene (—$CH_2CH_2CH_2$—), 2-methylpropylene (—$CH_2CH(CH_3)$—$CH_2$—), hexylene (—$(CH_2)_6$—) and the like. "Lower alkylene" refers to an alkylene group of 1 to 8, more preferably 1 to 6, carbon atoms. The term "cycloalkylene" as used herein refers to a divalent cyclic alkylene group, typically a 3-, 5-, 6-, 9-, or 10-membered ring. The term "heterocycloalkylene" refers to a similar divalent cyclic alkylene group containing one or more hetero atoms.

The term "alkenyl" as used herein intends a mono-unsaturated, di-unsaturated or polyunsaturated hydrocarbon group of 2 to 24 carbon atoms. Preferred groups within this class contain 2 to 12 carbon atoms. Asymmetric structures such as (AB)C═C(DE) are intended to include both the E and Z isomers. This may be presumed in structural formulae herein wherein an asymmetric alkene is present, or it may be explicitly indicated by the bond symbol.

The term "aryl" as used herein intends an aromatic carbocyclic ring, typically 6- or 10-membered, wherein at least one ring is aromatic. The term "heteroaryl" as used herein intends an aromatic ring containing one or more heteroatoms that is typically 5-, 6-, 9-, or 10-membered and can be mono or bicyclic.

The term "hetero or heteroatom" as used herein intends an atom other than carbon, such as sulfur, oxygen, and nitrogen that is included in a cyclic or acyclic group.

It will be appreciated by those skilled in the art that compounds of the invention having a chiral center may exist in and be isolated in optically active and racemic forms. Some compounds may exhibit polymorphism. It is to be understood that the present invention encompasses any racemic, optically active, polymorphic, or stereoisomeric form, or mixtures thereof, of a compound of the invention, which possesses the useful properties described herein. It being well known in the art how to prepare optically active forms (for example, by resolution of the racemic form by recrystallization techniques, by synthesis from optically active starting materials, by chiral synthesis, or by chromatographic separation using a chiral stationary phase) and how to determine the anticancer activity using the standard tests described herein, or using other similar tests which are well known in the art.

Specific and preferred values listed below for groups, substituents, and ranges, are for illustration only; they do not exclude other defined values or other values within defined ranges for the groups and substituents.

Specifically, alkyl can be methyl, ethyl, propyl, isopropyl, butyl, iso-butyl, sec-butyl, pentyl, 3-pentyl, or hexyl; cycloalkyl can be cyclopropyl, cyclobutyl, cyclopentyl, or cyclohexyl; alkoxy can be methoxy, ethoxy, propoxy, isopropoxy, butoxy, iso-butoxy, sec-butoxy, pentoxy, 3-pentoxy, or hexyloxy; (alkyl)-C(O)— can be acetyl, propanoyl or butanoyl; (cycloalkyl)-C(O)— can be cyclopropylcarbonyl, cyclopentylcarbonyl, cyclohexylcarbonyl or cycloheptylcarbonyl; hydroxyalkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; alkylmercapto can be methylthio, ethylthio, propylthio, isopropylthio, butylthio, isobutylthio, pentylthio, or hexylthio; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is branched alkyl, unbranched alkyl, polycycloalkyl, polycycloalkenyl, heteropolycycloalkyl, or heteropolycycloalkenyl.

Another specific value for $R^1$ is adamantyl, 2-ethyl-2-pentyl, 2-methyl-2-pentyl, tert-butylcarbonyl, bicyclooctyl, bicyclooctenyl, aza-bicyclooctyl, or aza-bicyclooctenyl.

Another specific value for $R^1$ is adamantyl, bicyclooctyl, bicyclooctenyl, aza-bicyclooctyl, or aza-bicyclooctenyl.

Another specific value for $R^1$ is adamantyl.

A specific value for $R^2$ is hydroxy, —$COOR^{14}$, —C(=O)CH$_3$, or —SH.

A more specific value for $R^2$ is hydroxy.

A specific value for $R^3$ is hydrogen, methyl, ethyl, chloro, bromo, fluoro, or —CF$_3$.

A specific value for $R^3$ is hydrogen, or methyl.

A specific value for $R^4$ is

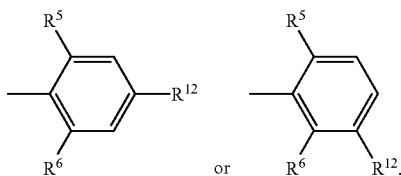

A specific value for $R^5$ is hydrogen, methyl, ethyl, methoxy, ethoxy, chloro, bromo, fluoro, —CF$_3$, —O—(CH$_2$)$_3$—NH$_2$ or —O—(CH$_2$)$_3$—NH—C(=O)CH$_3$.

A more specific value for $R^5$ is hydrogen, methyl, methoxy, ethoxy, chloro, bromo, or fluoro, —CF$_3$, —O—(CH$_2$)$_3$—NH$_2$ or —O—(CH$_2$)$_3$—NH—C(=O)CH$_3$.

A specific value for $R^6$ is hydrogen, methyl, ethyl, methoxy, ethoxy, chloro, bromo, fluoro, —CF$_3$, —O—(CH$_2$)$_3$—NH$_2$ or —O—(CH$_2$)$_3$—NH—C(=O)CH$_3$.

A more specific value for $R^6$ is hydrogen, methyl, methoxy, ethoxy, chloro, bromo, or fluoro, —CF$_3$, —O—(CH$_2$)$_3$—NH$_2$ OR or —O—(CH$_2$)$_3$—NH—C(=O)CH$_3$.

A more specific value for $R^6$ is hydrogen, methyl, chloro, bromo, or fluoro, —CF$_3$, —O—(CH$_2$)$_3$—NH$_2$ OR or —O—(CH$_2$)$_3$—NH—C(=O)CH$_3$.

A more specific value for $R^6$ is methyl, chloro, bromo, —CF$_3$, —O—(CH$_2$)$_3$—NH$_2$ OR or —O—(CH$_2$)$_3$—NH—C(=O)CH$_3$.

A specific value for $R^7$ is hydrogen, methyl, ethyl, alkoxy, chloro, bromo, fluoro, or —CF$_3$.

A more specific value for $R^7$ is hydrogen, methyl, methoxy, ethoxy, —O(CH$_2$)$_3$—NHR$_a$, chloro, bromo, or fluoro.

A more specific value for $R^7$ is hydrogen, methyl, methoxy, —O(CH$_2$)$_3$—NH—C(=O)CH$_3$, chloro, bromo, or fluoro.

A more specific value for $R^7$ is hydrogen, methyl, or chloro.

A specific value for $R^8$ is hydrogen, methyl, ethyl, methoxy, ethoxy, chloro, bromo, fluoro, or —CF$_3$.

A more specific value for $R^8$ is hydrogen, methyl, methoxy, ethoxy, chloro, bromo, or fluoro.

A specific value for $R^9$ is —$COOR^{14}$, —P(O)(OR$^{14}$)$_2$, —S(O)$_2$OR$^{14}$, or —C(O)—NHOR$^{14}$.

A more specific value for $R^9$ is —$COOR^{14}$.

Specific values for $R^{10}$ and $R^{11}$ are independently N, CH or CR$^7$.

More specific values for $R^{10}$ and $R^{11}$ are independently CH or CR$^7$.

A specific value for $R^{12}$ is —C(H)=C(H)(R$^9$), aryl-R$^9$,

A specific value for $R^{13}$ is NH, and N(C$_{1-10}$alkyl).

A specific value for $R^{14}$ is hydrogen, or alkyl.

A more specific value for $R^{14}$ is hydrogen, or —(CH$_2$)$_i$Me and i is from 0–22.

Another specific value for $R^{14}$ is hydrogen, methyl, or ethyl.

A specific group of compounds of the invention have the formula (II):

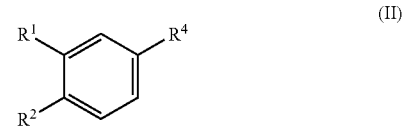

wherein $R^1$ is polycycloalkyl, e.g., adamantyl, $R^2$ is —OH, $R^4$ is

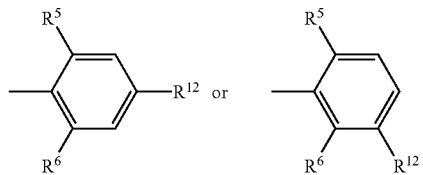

$R^{12}$ is —C(H)=C(H)—C(=O)OR$^{14}$ where $R^{14}$ is hydrogen or ethyl; and $R^5$ are $R^6$ are independently hydrogen, methyl, methoxy, chloro, fluoro, or —O—(CH$_2$)$_3$—NH—C(=O)CH$_3$.

A specific example of a compound of the invention is 4-[3-(1-adamantyl)-4-hydroxyphenyl]-3-chlorocinnamic acid (3-Cl-AHPC). 3-Cl-AHPC has the formula:

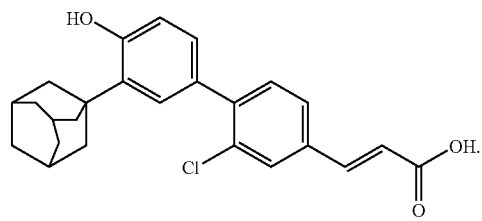

Another example of a specific compound of the invention has the formula:

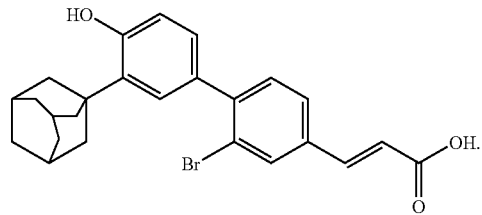

Another example of a specific compound of the invention has the formula:

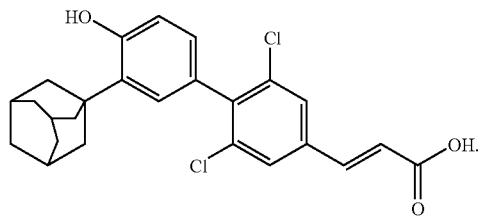

Another example of a specific compound of the invention has the formula:

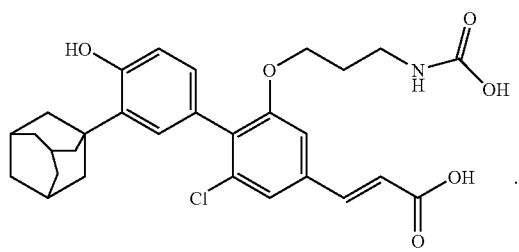

The compounds of the invention such as 3-Cl-AHPC induce apoptosis in cancer cells as indicated by the activation of caspases-9 and -3, cleavage of poly(ADP-ribose) polymerase, increase in annexin V binding and subsequent nuclear fragmentation. Apoptosis was not associated with the modulation of Bcl-2, Bax or Mcl-1 levels but with the cleavage of the anti-apoptotic protein Bcl-$X_L$ to a pro-apoptotic 18-kD form. This cleavage of Bcl-$X_L$ was dependent on caspase-3 activation since Bcl-$X_L$ cleavage and apoptosis was inhibited by the caspase-3 inhibitor Z-DVED-fmk. AHPN markedly inhibited the growth of AML cells in SCID mice. Tumor growth inhibition, growth delay and log cell kill were 85.7%, 21 days and 2.1, respectively, in the treated mice. Moreover, one out of the five treated mice was tumor-free more than 150 days and thus was considered cured. Exposure of both primary cultures of ALL cells obtained from patients to 3-Cl-AHPC resulted in their apoptosis. These results suggest that AHPN and 3-Cl-AHPC its analogs have a role in the treatment of ALL and other leukemias and cancers.

Processes for preparing compounds of formula I or for preparing intermediates useful for preparing compounds of formula I are provided as further embodiments of the invention. Intermediates useful for preparing compounds of formula I are also provided as further embodiments of the invention.

Compounds of the invention can generally be prepared using the synthetic schemes illustrated in the Schemes 1–6, below. Starting materials can be prepared by procedures described in these schemes or by procedures that would be well known to one of ordinary skill in organic chemistry. Any variables used in the Schemes are as defined below or as in the claims.

The syntheses of compounds 29–30 and 35–47 are illustrated in Schemes 1–3, which derive from routes for 3-Cl-AHPC (22) and 5-Cl-AHPN (19). Syntheses begin with commercially available materials and employ Pd-catalyzed couplings of aryl triflates (1-5, 1-20, 2-18, and 3-3) or bromides (1-8, 1-11, 2-14, and 3-10) with aryl stannanes (1-6 and 2-16) or boronic acids (1-3, 1-11, and 1-18) to form the diaryl bonds of 29–31 and 40–44, or carbonylative coupling of stannanes (3-6 and 3-8) to produce diaryl ketones (46 and 47), while the precursor of anthracene 45 employs an acyl stannane. Cinnamyl and 1,2-disubstituted trans-double bonds are generated by Horner-Wadsworth-Emmons olefinations of appropriately substituted benzaldehydes (1-21, 3-5, 3-9, and deprotected 2-15) or chlorination of a 1,2-diarylethyne (1-30). Reactive ring substituents are appropriately masked using protecting groups known in the art.

4-Br-3-nitroanisole (1-1) provides a means of introducing the 5'-Cl in compound 30, while 4-$NO_2$-3-$CF_3$-phenol (1-7) provides the 3- and 6'-$CF_3$ analogs 29 and 31. This synthesis provides the 3- and 6'-acetylenic analogs. Generation of the naphthalene ring of compound 35 is achieved using a Stobbe condensation of benzaldehyde 1-14 with dimethyl succinate, cyclization, and substituent manipulation to intermediate 1-18. Stereoselective syntheses of alkenyl-bridged analogs 37 and 38 are shown in (Scheme 1). The key steps in preparing compound 37 are the acid-catalyzed double-bond migration in compound 1-29 followed by photo-isomerization to the tetrasubstituted E-olefin, 37. The syntheses of benzothiophene, 39 and indoles, 40 and 41 (Scheme 2) are based on methods for preparing retinoids with heterocyclic five-membered rings. In preparing compound 40, N-acylation of the indole derived from compound 2-8 introduces an additional step but facilitates purification. The precursor for compounds 40 and 2-9 can also be deprotected and methylated to provide compound 41. Because indoles can be polymerized by Lewis acids, such as $BBr_3$, selective hydrogenation or treatment with NaSMe in DMF can be used. The route for 3-Cl-AHPC can be readily adapted for synthesis of thiophene, 42, while those for tetrahydrodinaphtho[1,2-b; 2', 3'-d]indole-3-carboxylic acids, 43 and 44 are adapted from our synthesis of the corresponding tetrahydrodinaphthothiophene.

$H_2$/Pt is used to selectively reduce the 6-$NO_2$ of compound 2-19 to the 6-$NH_2$ without benzyl ether cleavage. Diazotization and $NaN_3$ treatment will form azide 2-20, which on photolysis undergoes intramolecular insertion at the favored position (5-C—H) to provide 2-21 in good yield. Deprotection will afford compound 43, while compound 44 will require a penultimate methylation. The route to the oxime 45 of 6-(1-adamantylcarbonyl)-2-anthracenecarboxylic acid (Scheme 3) starts with 2,6-substituted anthracene 3-2. This compound can be prepared from compound 3-1 and has been reported in the literature. Oximation of ketone 3-4 followed by hydrolysis will provide compound 45 and its Z-isomer. These compounds can be used to prepare chlorinated analogs. Such groups can be inserted meta to the $CO_2H$ or ortho to the diaryl bond or C=O group.

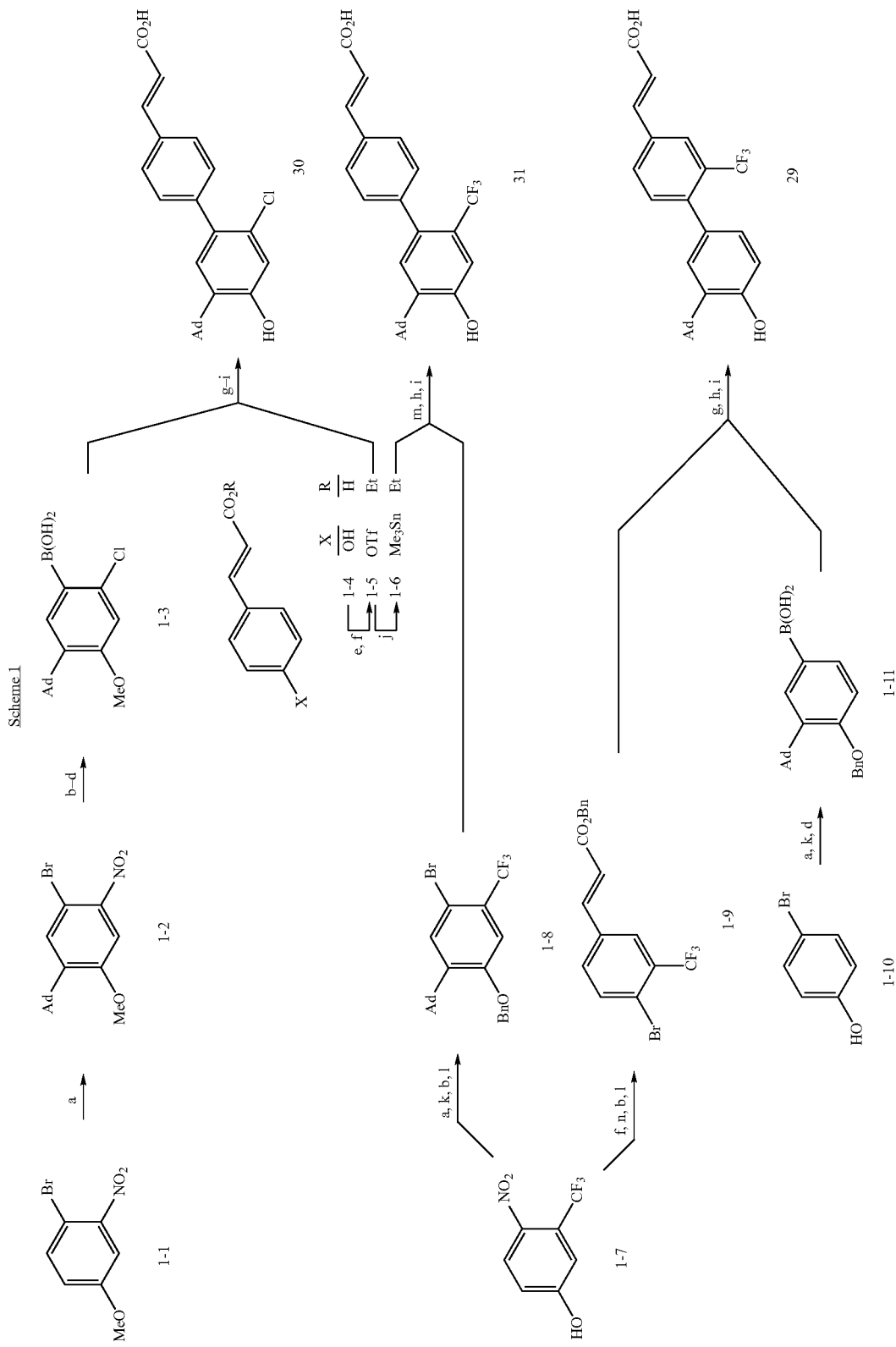

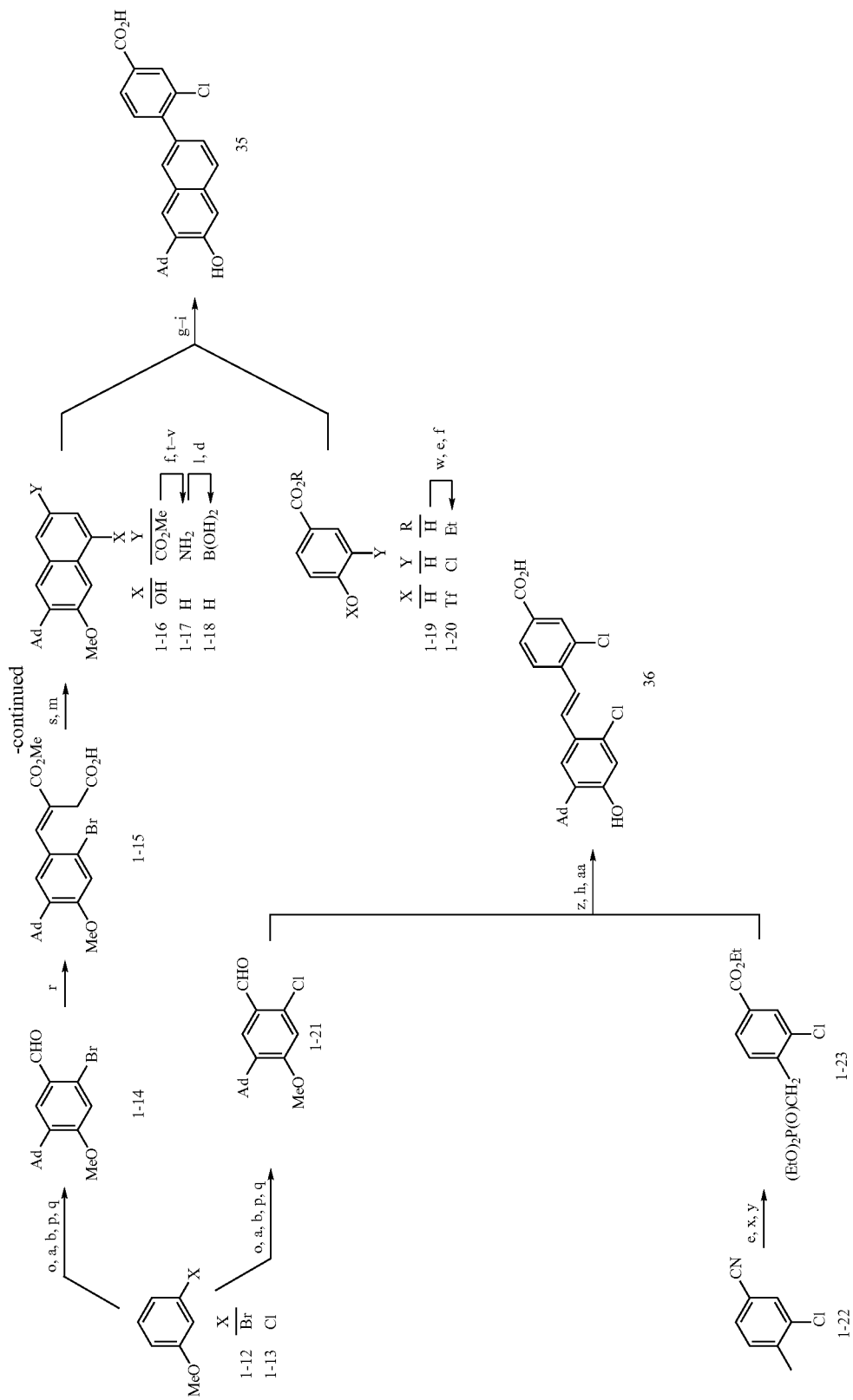

Scheme 1. (a) 1-AdOH, MeSO$_3$H. (b) SnCl$_2$, EtOH. (c) t-BuONO; CuCl. (d) n-BuLi, −78° C.; (i-PrO)$_3$B; aq. NH$_4$Cl. (e) EtOH, H$_2$SO$_4$. (f) Tf$_2$O, DMAP, py. (g) Pd(PPh$_3$)$_4$, PPh$_3$, aq. Na$_2$CO$_3$. (h) aq. KOH, EtOH; H$_3$O$^+$. (i) BBr$_3$, −78° C. (j) (Me$_3$Sn)$_2$, Pd(PPh$_3$)$_4$. (k) BnBr, K$_2$CO$_3$. (l) NaNO$_2$, H$_2$SO$_4$; CuBr. (m) PhPd(PPh$_3$)$_2$I. (n) (E)-(n-Bu)$_3$Sn(H)C=CHCO$_2$Bn, Pd(Ph$_3$)$_4$, LiCl. (o) HNO$_3$, HOAc. (p) NaNO$_2$, H$_2$SO$_4$; CuCN. (q) DIBAL; H$_3$O$^+$. (r) (CH$_2$CO$_2$t-Bu)$_2$, KOt-Bu. (s) (COCl$_2$)$_2$. (t) Me$_3$SnH, Pd(PPh$_3$)$_4$. (u) NH$_3$ (xs). (v) NaOBr. (w) SO$_2$Cl$_2$. (x) NBS, (BnO)$_2$, hv. (y) (EtO)$_3$P. (z) [1-23, KHMDS]. (aa) BBr$_3$, 0° C.

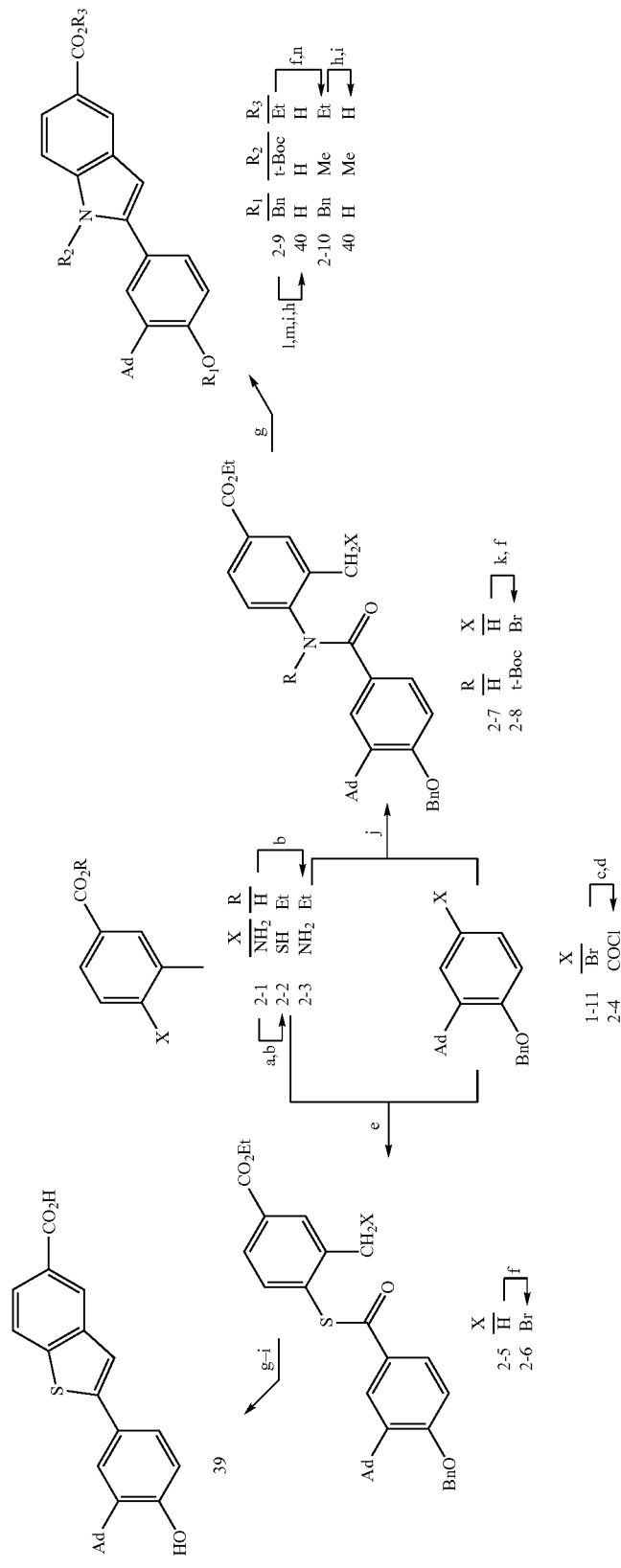
Scheme 2

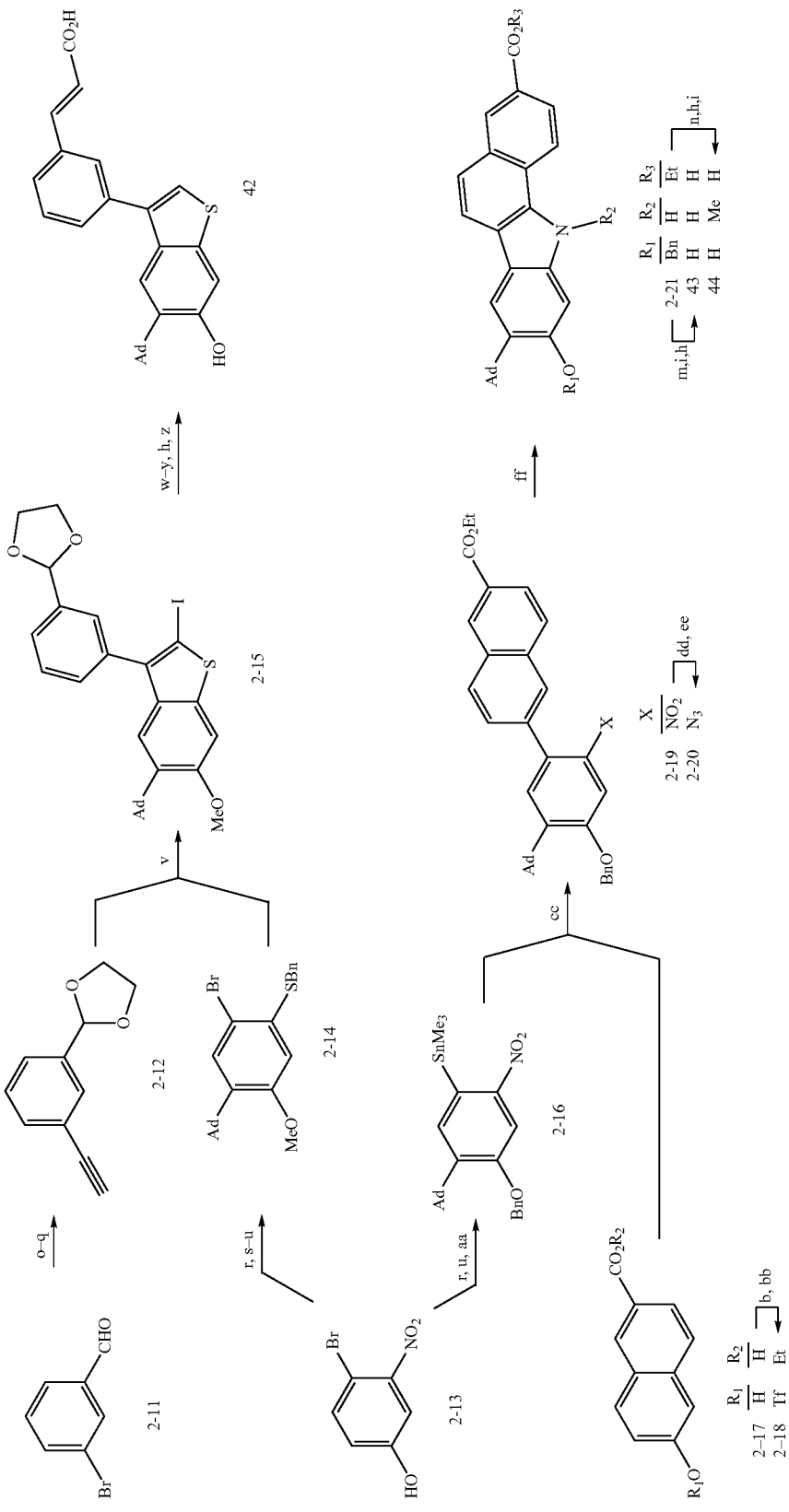

Scheme 2. (a) NaNO$_2$, HCl, 0° C.; [Na$_2$S, S, aq. NaOH, 100° C.], 5° C.; HCl; Zn, HOAc. (b) HCl (gas), EtOH. (c) Mg, Et$_2$O; CO$_2$ (gas), −78° C.; H$_3$O$^+$. (d) (COCl)$_2$. (e) TEA. (f) NBS, (BnO)$_2$, hv. (g) P(Ph)$_3$, DBU. (h) aq. KOH, EtOH; H$_3$O$^+$. (i) BBr$_3$, −78° C.; H$_3$O$^+$. (j) Et$_3$N, 0° C. (k) (t-BuCO)$_2$ O, DMAP TEA, 0°–20° C. (l) TFA. (m) AcCl. (n) NaH, MeI. (o) (CH$_2$OH)$_2$, TsOH. (p) (n-Bu)$_3$ SnC≡CTMS, Pd(PPh$_3$)$_4$ (q) (n-Bu)$_4$NF. (r) 1-AdOH, MeSO$_3$H. (s) MeI, K$_2$CO$_3$. (t) NaNO$_2$, HBF$_4$; KSC(S)OEt; KOH, MeOH. (u) BnBr, K$_2$CO$_3$. (v) [2-12, n-BuLi]; ZnCl$_2$; Pd(PPh$_3$)$_2$Cl$_2$; [2-14, n-BuLi]; I$_2$. (w) Me$_3$SnH. (x) H$_3$O$^+$. (y) [(EtO)$_2$P(O) CH$_2$CO$_2$Et, KHMDS]. (z) BBr$_3$, 0° C.; H$_3$O$^+$. (aa) (Me$_3$Sn)$_2$, Pd(PPh$_3$)$_4$. (bb) Tf$_2$O, DIMAP, TEA. (cc) Pd(PPh$_3$)$_2$Cl$_2$, LiCl. (dd) H$_2$, PtO$_2$, EtOH. (ee) i-AmONO, TFA, 0° C.; NaN$_3$, 0°–20° C. (ff) hv, 1,2-Cl$_2$–C$_6$H$_4$.

lidine, Pd(PPh$_3$)$_4$. (e) BBr$_3$, 0° C.; H$_3$O$^+$. (f) 1-AdCOSnMe$_3$, Pd(PPh$_3$)$_2$Cl$_2$. (g) TFA, Na$_2$SO$_4$, H$_2$O (trace); Ac$_2$O, py; [KOt-Bu, H$_2$O]; H$_3$O$^+$. (h) MeI, K$_2$CO$_3$. (i) HONH$_2$.HCl, NaOAc. (j) LiOH; H$_3$$^+$. (k) BnCl, K$_2$CO$_3$. (l) [(EtO)$_2$P(O) CHCO$_2$Et, KHMDS]. (m) BBr$_3$, −78° C.; H$_3$$^+$. (n) [(n-Bu)$_3$ Sn]$_2$, Pd(PPh$_3$)$_4$. (o) 3-(1-Ad)-4-(MOMO)—C$_6$H$_3$—Br, Pd(PPh$_3$)$_2$Cl$_2$, CO. (p) TFA. (q) aq. KOH, EtOH; H$_3$O$^+$. (r) 1-AdOH, MeSO$_3$H. (s) NaNO$_2$, H$_2$SO$_4$; CuCl. (t) MOMCl, NaH. (u) Pd(PPh$_3$)$_2$Cl$_2$, CO.

Scheme 4 illustrates routes to 3'-(alkyl) analogs 48–53. Friedel-Crafts alkylations can only be readily accomplished using symmetrical tertiary alkyl alcohols, such as 1-adamantanol, or bromides that do not undergo structural rearrangements. The 3,5-dimethyl-1-adamantyl (3,5-Me$_2$-Ad) group can be introduced by this alkylation of 4-Br-phenol (1-10).

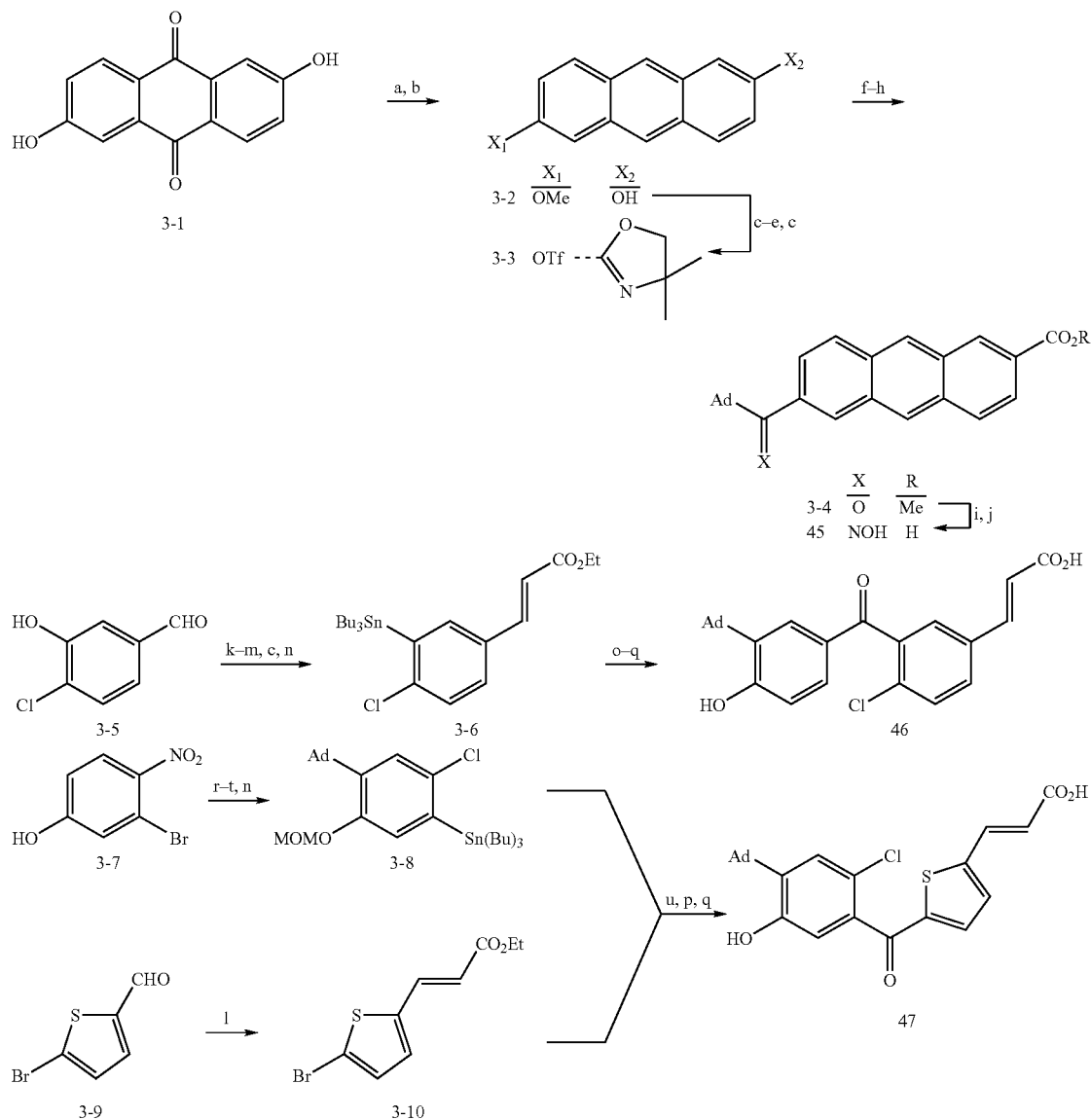

Scheme 3

Scheme 3. (a) Al(Hg), EtOH, H$_2$O. (b) HCl, MeOH, 3 days. (c) Tf$_2$O, DMAP, py. (d) 2-(Me$_3$Sn)-4,4-Me$_2$-oxazo- Other groups require different strategies. A useful synthon for introducing tertiary alkyl groups ortho to phenolic t-Boc esters can be used to produce 2-(3-ethylpent-3-yl)phenol and transform 4-3 to 4-5, a precursor of 49. The dimethylphenyl, t-Bu-ethynyl and bicycloalkenyl groups are introduced by a controlled Pd-catalyzed coupling of their corresponding stannanes with 2-iodo-4-bromophenol (4-3) so that the more reactive iodo group couples to leave the 4-bromo available for conversion to the boronic ester. Alternatively, the 4-Benzyloxy-2-iodo-phenol also undergoes coupling, methylation, debenzylation, then conversion to the 4-TfO for coupling with an aryl stannane. Ortho-iodination of 4-bromophenol (1-10) will provide 4-3. Analogs 50 and 51 are prepared by Pd-catalyzed coupling of 2,6-$Me_2$-phenyl and t-Bu-C≡C stannanes with 4-3. The bicycloalkenyl rings of 52 and 53 are similarly introduced using alkenylstannanes 4-14 and 4-17.

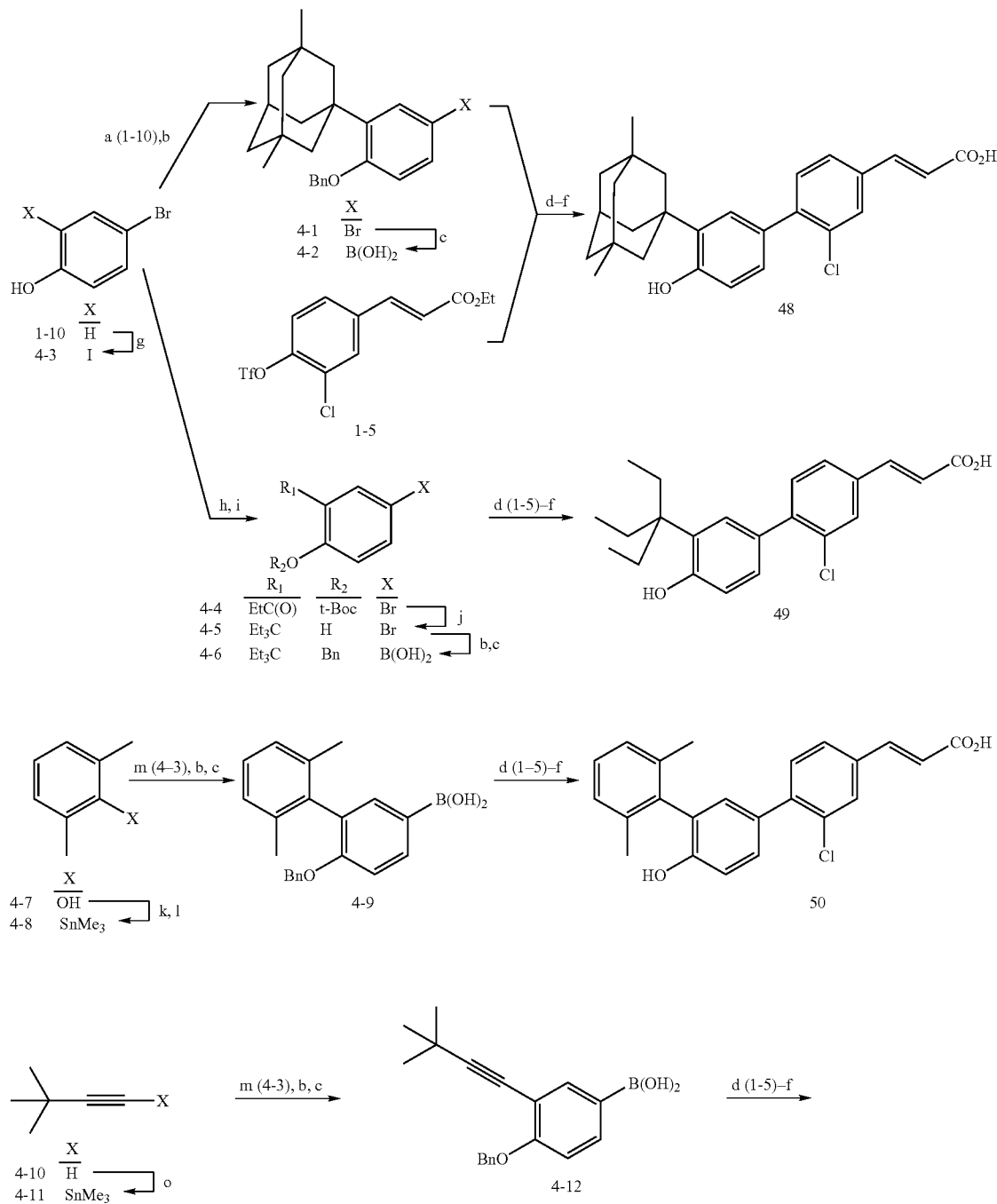

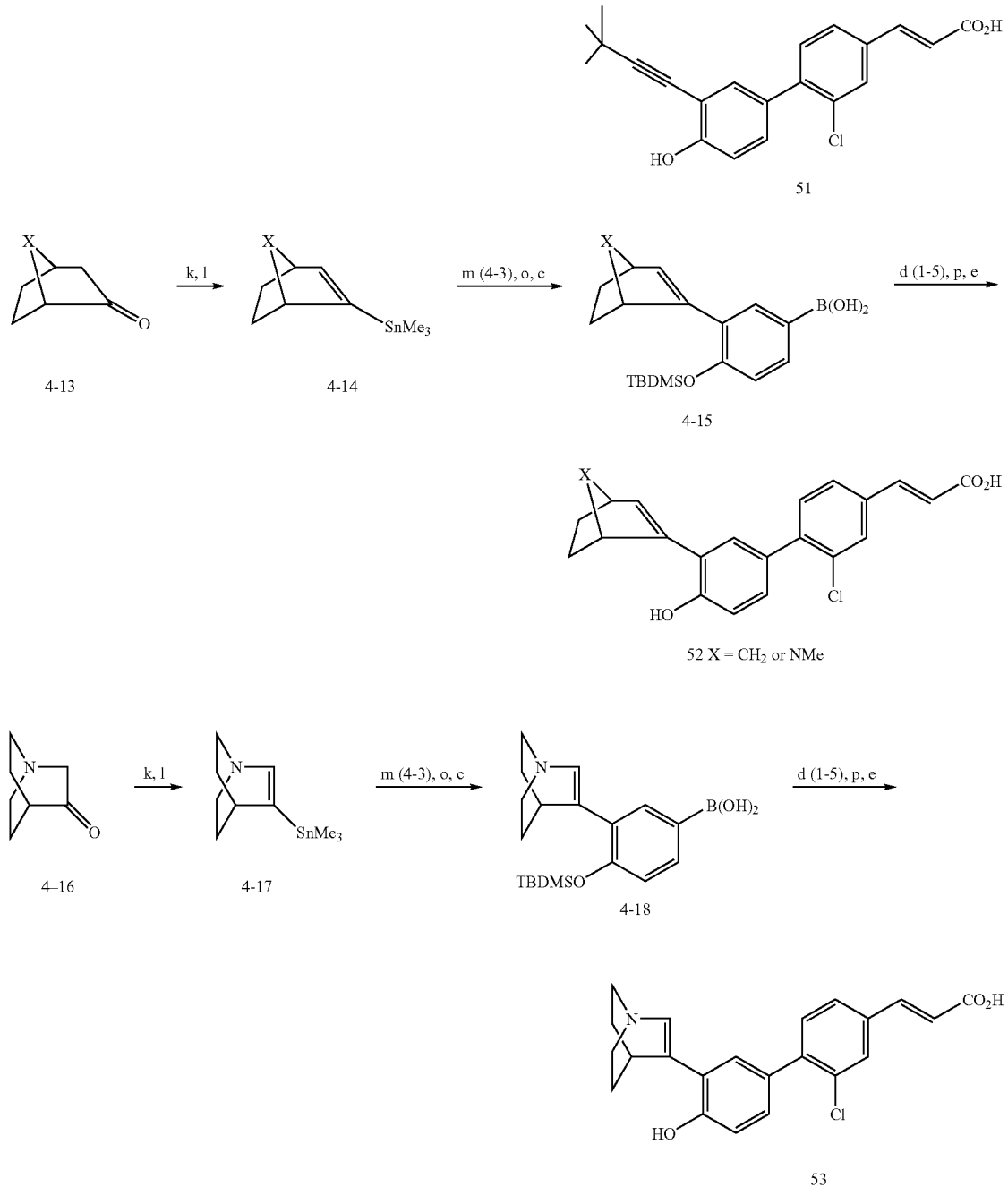

Scheme 4. (a) 1-Br-3,5-Me$_2$-Ad, ZnCl$_2$. (b) BnBr, K$_2$CO$_3$. (c) n-BuLi, −78° C.; (i-PrO)$_3$B; aq. NH$_4$Cl. (d) Pd(PPh$_3$)$_4$, PPh$_3$, aq. Na$_2$CO$_3$. (e) aq. KOH, MeOH. (f) BBr$_3$, −78° C. (g) I(sym-collidine)$_2$PF$_6$. (h) EtCN, ZnCl$_2$, HCl(g); H$_2$O. (i) NaH, (t-BOC)$_2$O. (j) EtMgBr (2 equiv.); H$_2$O. (k) Tf$_2$O, DIMAP. (l) (Me$_3$Sn)$_2$, Pd(PPh$_3$)$_4$, LiCl. (m) Pd$_2$(dba)$_3$, CuI, AsPh$_3$. (n) [n-BuLi], step (l). (o) TBDMSCl, imidazole. (p) (n-Bu)$_4$NF.

Synthetic routes to analogs having 4-azido-benzoyl photoaffinity-labeling groups are shown in Scheme 5. These groups are introduced at the 3-position of the AHPC cinnamyl ring (33) or at the 4'-position of the AHPN phenyl ring (58). 3-Amino-4-hydroxybenzoic acid (5-15) is available for preparing cinnamic ester 5-17. Intermediate 5-17 is deprotected, and the 4-OH compound is converted to the triflate for coupling with aryl boronic acid 5-9 to introduce the diaryl bond. Deprotection, acylation with activated 4-azidobenzoyl imidazolide, and selective hydrolysis of the ester formed provides compound 33. The 2-cinnamyl analog is prepared similarly from 2-amino-4-hydroxy-benzoic acid. The synthesis of compound 58 is accomplished by acylation of 54 with the same imidazolide.

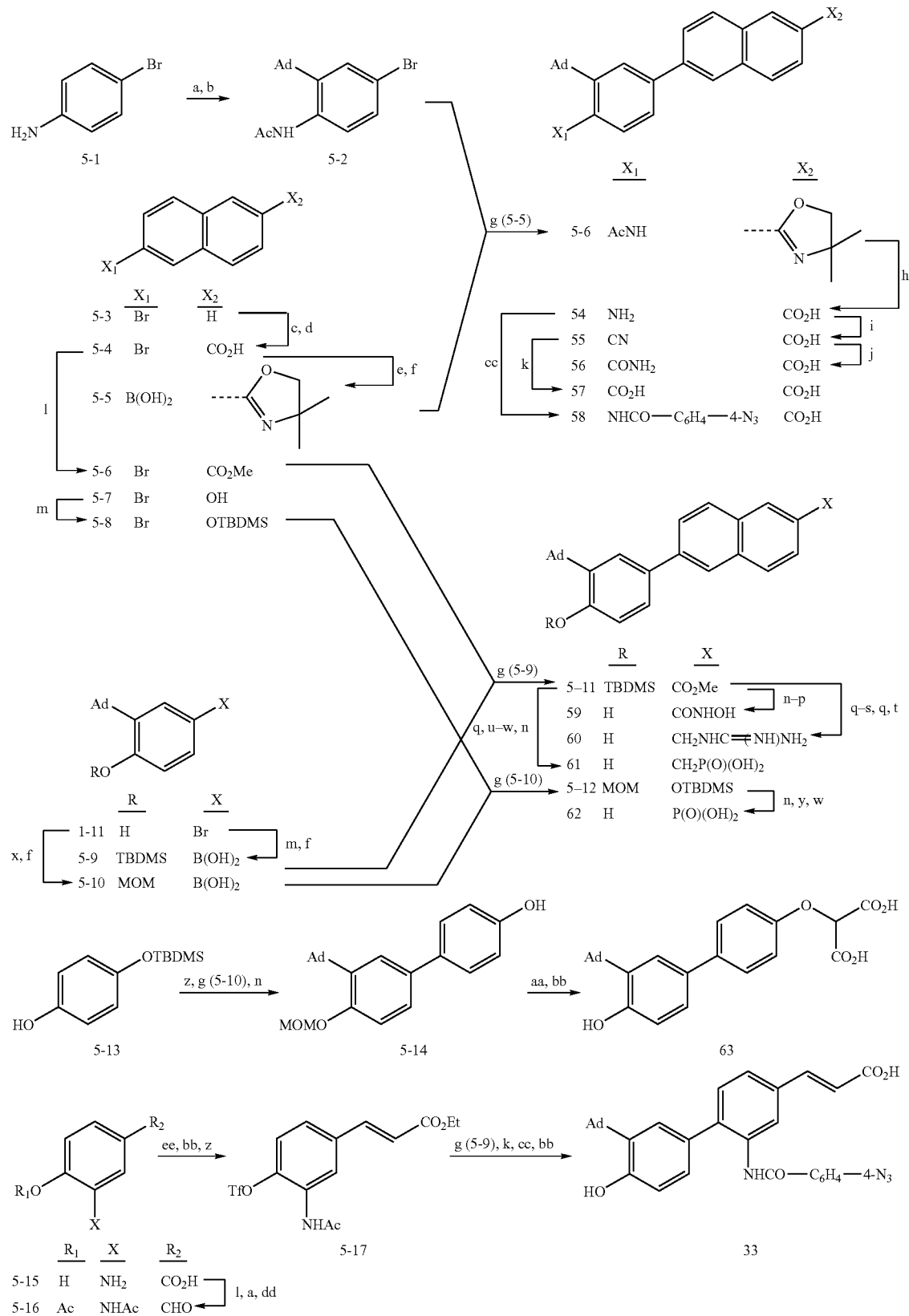
Scheme 5

Scheme 5. (a) Ac$_2$O, py. (b) 1-AdOH, MeSO$_3$H. (c) AcCl, AlCl$_3$, (CH$_2$Cl)$_2$. (d) NaOCl, NaOH, H$_3$O$^+$. (e) SOCl$_2$; HOCH$_2$CMe$_2$NH$_2$; SOCl$_2$. (f) n-BuLi, –78° C.; (i-PrO)$_3$B; aq. NH$_4$Cl. (g) Pd(PPh$_3$)$_4$, PPh$_3$, aq. Na$_2$CO$_3$. (h) TFA, Na$_2$SO$_4$, H$_2$O (trace); Ac$_2$O, py; aq. NaOH, EtOH; H$_3$O$^+$. (i) NaNO$_2$, H$_2$SO$_4$; NaCN. (j) KOH, (CH$_2$OH)$_2$; H$_3$O$^+$. (k) aq. KOH, EtOH; H$_3$O$^+$. (l) MeOH, H$_2$SO$_4$. (l) MeOH, H$_2$SO$_4$. (m) TBDMSCl, imid. DMF. (n) (n-Bu)$_4$NF. (o) LiOH. (p) EDIC, t-BuOH, O-trityl-ONH-resin; 30% HCO$_2$H. (q) LAH; H$_3$O$^+$. (r) MsCl, py. (s) NaN$_3$. (t) Me$_2$SC(=Nt-Boc)NHt-Boc; HgCl$_2$, TEA; TFA. (u) CBr$_4$, PPh$_3$. (v) (MeO)$_3$P. (w) TMSBr; H$_3$O$^+$(P-4). (x) MOMCl, NaH. (y) (EtO)$_2$POH, TEA, Pd(PPh$_3$)$_4$. (z) Tf$_2$O, DIMAP, py. (aa) N$_2$C(CO$_2$t-Bu)$_2$. (bb) TFA. (cc) 4-N$_3$–C$_6$H$_4$CO-imidazolide (dark). (dd) DIBAL. (ee) [(EtO)$_2$P(O)CH$_2$CO$_2$Et, KHMDS].

The invention will be further described by reference to the following detailed examples.

The following materials were used: fetal bovine serum (FBS), RPMI media and gentamycin, mouse anti-poly (ADP-ribose) polymerase antibody (PARP) anti-Bcl-X$_L$ antibodies, anti-phospho-p38 antibody, anti-phospho-JNK antibodies, t-RA, AHPN (Galderma) (Bernard, B. A., Bernardon, J. M., Delesclose C., et al., Biochem. Biophys. Res. Commun., 186: pages 977–983 (1992). The Z-oxime of 6-(5,6,7,8-tetrahydro-5,5,8,8-tetramethyl-2-naphthalenyl-carbonyl)-2-naphthalenecarboxylic acid (11254) is an RARγ-transcriptional agonist (Chao, W. R., Hobbs, P. D., Jong, L., et al., Cancer Lett., 115: pages 1–7 (1997)).

Figure 1B:
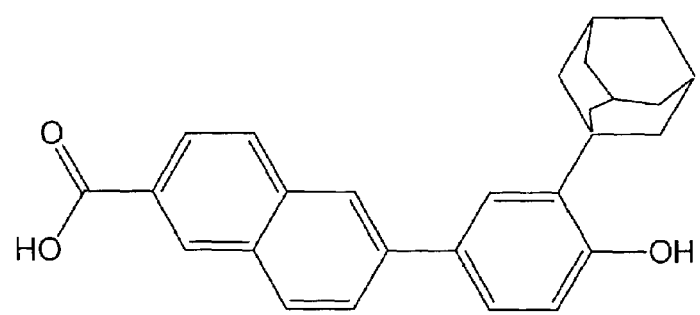

4-[3-(1-Adamantyl)-4-hydroxyphenyl]-3-chlorocinnamic acid (3-Cl-AHPC) (FIG. 1) at 1.0 μM does not activate RARα, RARβ, and RXRα on the (TREpal)$_2$-tk-CAT reporter construct and its activation of RARγ is less than 10 percent that of 1.0 μM tRA.

EXAMPLE 1

(E)-4-[3-(1-Adamantyl)-4-hydroxyphenyl]-3-chlorocinnamic acid (3-Cl-AHPC)

The synthesis of 3-Cl-AHPC was accomplished in seven steps as follows. Unless noted, the work-ups included extraction into ethyl acetate, washing (water, followed by saturated brine), drying (MgSO$_4$), concentration, and, if necessary, flash column chromatography on silica gel.

Step 1: 4-Acetoxy-3-chlorobenzaldehyde. Step 1: 4-Acetoxy-3-chlorobenzaldehyde.

To 3-chloro-4-hydroxybenzaldehyde (5.00 g, 31.9 mmol) and pyridine (5.0 mL, 61.8 mmol) in dichloromethane (40 mL) at 0° C. was added acetic anhydride (4.0 mL, 42.3 mmol) over a 20-minute period. The mixture was stirred for 1.5 hours more, warmed to 20° C., then worked-up (10% hydrochloric acid wash) to afford 4-acetoxy-3-chlorobenzaldehyde as a pale-yellow solid (6.01 g, 92% yield): m.p. 33–35° C.; R$_f$0.30 (20% ethyl acetate/hexane); $^1$H NMR spectrum (400 MHz, CDCl$_3$) δ 2.39 (s, 3, CH$_3$), 7.34 (d, J=8.0 Hz, 1, ArH), 7.82 (dd, J=7.6,2 Hz, 1, ArH), 7.98 (d, J=1.6 Hz, 1, ArH), 9.96 ppm (s, 1, CHO).

Step 2: Ethyl (E)-4-acetoxy-3-chlorocinnamate.

To the acetylated benzaldehyde (5.94 g, 29.9 mmol), prepared in Step 1, and K$_2$CO$_3$ (12.40 g, 89.7 mmol) in anhydrous tetrahydrofuran (40 mL) under argon was added triethyl phosphonoacetate (13.0 mL, 65.5 mmol). The mixture was stirred for 96 hours, then worked-up, and chromatographed (20% ethyl acetate/hexane) to yield ethyl (E)-4-acetoxy-3-chlorocinnamate as a white solid (6.96 g, 87%): m.p. 59–61° C.; R$_f$0.36 (20% ethyl acetate/hexane); $^1$H NMR spectrum (400 MHz, CDCl$_3$) δ 1.34 (t, J=6.4 Hz, 3, CH$_3$), 2.37 (s, 3, CH$_3$), 4.26 (q, J=8.0 Hz, 2, CH$_2$), 6.40 (d, J=16.4 Hz, 1, HC=CCO), 7.17 (d, J=9.2 Hz, 1, ArH), 7.42 (dd, J=8.6, 2.0 Hz, 1, ArH), 7.60 (d, J=16.0 Hz, 1, C=CHCO), 7.61 ppm (d, J=2.0 Hz, 1, ArH).

Step 3: Ethyl (E)-3-chloro-4-hydroxycinnamate.

To the ethyl cinnamate (6.89 g, 25.6 mmol), prepared in Step 2, in methanol (50 mL) was added K$_2$CO$_3$ (7.00 g, 50.6 mmol). This mixture was stirred for 4 hours, then worked-up (10% hydrochloric acid wash) to afford ethyl (E)-3-chloro-4-hydroxycinnamate as a white solid (5.05 g, 87% yield): m.p. 104–106° C.; R$_f$0.22 (20% ethyl acetate/hexane); $^1$H NMR spectrum (300 MHz, CDCl$_3$) δ 1.44 (t, J=7.1 Hz, 3, CH$_3$), 4.44 (q, J=7.1 Hz, 2, CH$_2$), 5.75 (s,1, OH), 6.31 (d, J=16.0 Hz, 1, HC=CCO), 7.03 (d, J=8.8 Hz, 1, ArH), 7.37 (dd, J=8.8, 2.0 Hz, 1, ArH), 7.51 (d, J=2.0 Hz, 1, ArH), 7.57 ppm (d, J=16.0 Hz, 1, C=CHCO).

Step 4: Ethyl (E)-3-chloro-4-(trifluoromethanesulfonyloxy)cinnamate.

To the ethyl hydroxycinnamate (5.02 g, 22.1 mmol), prepared in Step 3, and pyridine (4.0 mL, 50.0 mmol) in dichloromethane (50 mL) at 0° C. under argon was added trifluoromethanesulfonic anhydride (4.0 mL, 23.7 mmol) over a 30-minute period. The mixture was stirred for 4 hours, warmed to 20° C., then worked-up (10% hydrochloric acid and 5% NaHCO$_3$ washes) to afford ethyl (E)-3-chloro-4-(trifluoromethanesulfonyloxy)cinnamate as a white solid (7.90 g, 98% yield): m.p. 59–61° C.; R$_f$0.49 (20% ethyl acetate/hexane); $^1$H NMR spectrum (300 MHz, CDCl$_3$) δ 1.35 (t, J=7.1 Hz, 3, CH$_3$), 4.28 (q, J=7.1 Hz, 2, CH$_2$), 6.45 (d, J=16.0 Hz, 1, HC=CCO), 7.38 (d, J=8.5 Hz, 1, ArH), 7.48 (dd, J=8.5, 1.8 Hz, 1, ArH), 7.59 (d, J=16.0 Hz, 1, C=CHCO), 7.67 ppm (d, J=1.9 Hz, 1, ArH).

Step 5: Ethyl (E)-4-[3-(1-adamantyl)-4-benzyloxyphenyl]-3-chlorocinnamate.

Aqueous Na$_2$CO$_3$ (1.4 mL, 2.0 M) was added to the ethyl (trifluoro-methane-sulfonyloxy)cinnamate (0.55 g, 1.53 mmol), 3-(1-adamantyl)-4-benzyloxyphenylboronic acid (0.50 g, 1.38 mmol) [$^1$H NMR spectrum (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (mn, 5, ArH), 8.03 (d, J=7.8 Hz, 1, ArH), 8.19 ppm (s, 1, ArH)], tetrakis (triphenylphosphine)palladium (0.16 g, 0.14 mmol), and lithium chloride (0.13 g, 3.1 mmol) in dimethoxyethane (12 mL) under argon. The mixture was heated at reflux (80–85° C.) overnight to achieve the biaryl coupling, then worked-up, and chromatographed (10% ethyl acetate/hexane) to give ethyl (E)-4-[3-(1-adamantyl)-4-benzyloxyphenyl]-3-chlorocinnamate as a white solid (0.58 g, 79%): m.p. 148–150° C.; R$_f$0.61 (20% ethyl acetate/hexane); $^1$H NMR spectrum (300 MHz, CDCl$_3$) δ 1.73, 2.17 (2 s, 12, AdCH$_2$), 2.04 (s, 3, AdCH), 1.33 (t, J=7.1 Hz, 3 CH$_3$), 4.26 (q, J=7.1 Hz, 2, CH$_2$), 5.17 (s, 2, CH$_2$), 6.46 (d, J=15.9 Hz, 1, HC=CCO), 7.00 (d, J=8.2 Hz, 1, ArH), 7.3–7.5 (m, 8, ArH), 7.52 (d, J=7.1 Hz, 1, ArH), 7.62 (s, 1, ArH), 7.65 ppm (d, J=15.4 Hz, 1, C=CHCO).

Step 6: Ethyl (E)-4-[3-(1-adamantyl)-4-hydroxyphenyl]-3-chlorocinnamate.

To the ethyl benzyloxyphenylcinnamate (0.50 g, 0.95 mmol), prepared in Step 5, in dichloromethane (10 mL) at –78° C. under argon was added boron tribromide in dichloromethane (3.0 mL, 1.0 M) over a 30-minute period. The mixture was stirred for 2 hours, worked-up, and chromatographed (20% ethyl acetate/hexane) to yield ethyl (E)-4-[3-(1-adamantyl)-4-hydroxyphenyl]-3-chlorocinnamate as a pale-yellow solid (0.38 g, 92%): m.p. 216–218° C.; $R_f$ 0.37 (20% ethyl acetate/hexane); $^1$H NMR spectrum (300 MHz, CDCl$_3$) δ 1.79, 2.15 (2 s, 12, AdCH$_2$), 2.09 (s, 3, AdCH), 1.35 (t, J=7.1 Hz, 3, CH$_3$), 4.28 (q, J=7.1 Hz, 2, CH$_2$), 4.93 (s, 1, OH), 6.46 (d, J=15.4 Hz, 1, HC=CCO), 6.72 (d, J=7.8 Hz, 1, ArH), 7.19 (d, J=7.8 Hz, 1, ArH), 7.32 (s, 1, ArH), 7.36 (d, J=8.1 Hz, 1, ArH), 7.44 (d, J=8.2 Hz, 1, ArH), 7.62 (s, 1, ArH) 7.64 ppm (d, J=15.5 Hz, 1, C=CHCO).

Step 7: (E)-4-[3-(1-Adamantyl)-4-hydroxyphenyl]-3-chlorocinnamic acid.

To the ethyl ester (0.35 g, 0.80 mmol), prepared in Step 6, in aqueous ethanol (40 mL, 75%) was added NaOH (1 pellet). This mixture was stirred at 85° C. for 2 hours, acidified (10% hydrochloric acid), then worked-up to afford (E)-4-[3-(1-adamantyl)-4-hydroxyphenyl]-3-chlorocinnamic acid as a pale-tan solid (0.28 g, 85%): m.p. 257–259° C.; $R_f$ 0.42 (75% ethyl acetate/hexane); $^1$H NMR spectrum (300 MHz, DMSO-d$_6$) δ 1.73, 2.09 (2 s, 12, AdCH$_2$), 2.03 (s, 3, AdCH), 6.62 (d, J=16.4 Hz, 1, HC=CCO), 6.85 (d, J=8.3 Hz, 1, ArH), 7.14 (d, J=8.1 Hz, 1, ArH), 7.17 (s, 1, ArH), 7.41 (d, J=8.0 Hz, 1, ArH), 7.59 (d, J=15.9 Hz, 1, C=CHCO), 7.69 (d, J=7.9 Hz, 1, ArH), 7.88 ppm (s, 1, ArH); mass spectrum (electron-impact high-resolution): calculated for $C_{25}H_{25}ClO_3$, 408.1492. found, 408.1492.

EXAMPLE 2

Synthesis of (E)-4-[3-(1-Adamantyl)-4-hydroxyphenyl]-2-chlorocinnamic acid

Step 1: 4-Acetoxy-2-chlorobenzaldehyde.

A mixture of 2.43 g (15.5 mmol) of 2-chloro-4-hydroxybenzaldehyde and 5.0 ml (37.1 mmol) of pyridine in 40 ml of CH$_2$Cl$_2$ was stirred in a 0° C. ice bath, while 3.0 ml (31.8 mmol) of acetic anhydride was added over a period of 20 minutes. The reaction mixture was stirred for 1.5 hours more, then warmed to room temperature. The mixture was extracted with EtOAc, washed with 10% HCl, brine, and water, dried (MgSO$_4$), filtered, and concentrated to afford a pale-yellow solid (2.98 g, 96% yield): m.p. 41–43° C.; $R_f$ 0.41 (20% EtOAc/hexane); $^1$H NMR (400 MHz, CDCl$_3$) δ 2.33 (s, 3, CH$_3$), 7.16 (dd, J=8.6, 2.0 Hz, 1, ArH), 7.28 (d, J=1.6 Hz, 1, ArH), 7.97 (d, J=8.8 Hz, 1, ArH), 10.42 ppm (s, 1, CHO).

Step 2: Ethyl (E)-4-acetoxy-2-chlorocinnamate.

To a suspension of 2.91 g (14.6 mmol) of 4-acetoxy-2-chlorobenzaldehyde and 6.00 g (43.4 mmol) of K$_2$CO$_3$ in 40 ml of anhydrous THF under Ar, 6 ml (30.4 mmol) of triethyl phosphonoacetate was added. The reaction mixture was stirred at room temperature for 4 days at which time the reaction was complete, then extracted with EtOAc, washed with brine and water, dried (MgSO$_4$), filtered, and concentrated. Flash column chromatography (20% EtOAc/hexane) yielded a yellowish oil (3.03 g, 77% yield): $R_f$ 0.35 (20% EtOAc/hexane); $^1$H NMR (400 MHz, CDCl$_3$) δ 1.35 (t, J=6.8 Hz, 3, CH$_3$), 2.31 (s, 3, CH$_3$), 4.28 (q, J=6.4 Hz, 2, CH$_2$), 6.40 (d, J=16.0 Hz, 1, HC=CCO), 7.06 (dd, J=8.8, 2.4 Hz, 1, ArH), 7.22 (d, J=2.0 Hz, 1, ArH), 7.63 (d, J=8.8 Hz, 1, ArH), 8.04 ppm (d, J=16.0 Hz, 1, C=CHCO).

Step 3: Ethyl (E)-2-chloro-4-hydroxycinnamate.

To a solution of 2.87 g (10.6 mmol) of ethyl (E)-4-acetoxy-2-chlorocinnamate in 30 ml of MeOH was added 3.00 g (21.7 mmol) of K$_2$CO$_3$. This mixture was stirred at room temperature for 4 hours, at which time the reaction was complete. The mixture was extracted with EtOAc, and the extract was washed with 10% HCl, brine, and water, dried (MgSO$_4$), filtered and concentrated to afford a pale-yellow solid (1.73 g, 72% yield): m.p. 145–147° C.; $R_f$ 0.21 (20% EtOAc/hexane); $^1$H NMR (400 MHz, CDCl$_3$) δ 1.35 (t, J=6.8 Hz, 3, CH$_3$), 4.28 (q, J=6.4 Hz, 2, CH$_2$), 5.48 (s, 1, OH), 6.33 (d, J=16.0 Hz HC=CCO), 6.77 (dd, J=8.8, 2.4 Hz, 1, ArH), 6.93 (d, J=2.4 Hz, 1, ArH), 7.54 (d, J=8.8 Hz, 1, ArH), 8.04 ppm (d, J=16.0 Hz, 1, C=CHCO).

Step 4: Ethyl (E)-2-chloro-4-(trifluoromethanesulfonyloxy)cinnamate.

To a solution of 1.71 g (7.5 mmol) of ethyl (E)-2-chloro-4-hydroxycinnamate and 1.5 ml (18.5 mmol) of pyridine in 30 ml of CH$_2$Cl$_2$ in a 0° C. ice bath under Ar, 1.5 ml (8.9 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% NaHCO$_3$, brine, and water, dried (MgSO$_4$), filtered, and concentrated to afford a light-yellow oil (2.85 g, 95% yield): $R_f$ 0.62 (20% EtOAc/hexane); $^1$H NMR (400 MHz, CDCl$_3$) δ 1.35 (t, J=7.1 Hz, 3, CH$_3$), 4.28 (q, J=7.1 Hz, 2, CH$_2$), 6.45 (d, J=15.6 Hz, 1, HC=CCO), 7.24 (dd, J=9.0, 2.8 Hz, 1, ArH), 7.39 (d, J=2.4 Hz, 1, ArH), 7.70 (d, J=8.8 Hz, 1, ArH), 8.02 ppm (d, J=16.8 Hz, 1, C=CHCO).

Step 5: Ethyl (E)-4-[3-(1-adamantyl)-4-benzyloxyphenyl]-2-chlorocinnamate.

To a stirred suspension of 1.00 g (2.78 mmol) of ethyl (E)-2-chloro-4-(trifluoromethanesulfonyloxy)cinnamate, 1.00 g (2.76 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of Pd[P(C$_6$H$_5$)$_3$]$_4$, and 0.26 g (6.1 mmol) of LiCl in 20 ml of DME was added under Ar 2.8 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a white solid (1.33 g, 91%): m.p. 67–69° C.; $R_f$ 0.44 (20% EtOAc/hexane); $^1$H NMR (300 MHz, CDCl$_3$) δ 1.74, 2.19 (2 s, 12, AdCH$_2$), 2.07 (s, 3, AdCH), 5.17 (s, 2, CH$_2$), 1.33 (t, J=7.1 Hz, 3 CH$_3$), 4.26 (q, J=7.1 Hz, 2, CH$_2$), 6.46 (d, J=16.0 Hz, 1, HC=CCO), 7.01 (d, J=8.0 Hz, 1, ArH), 7.3–7.5 (m, 8, ArH), 7.61 (d, J=2.4 Hz, 1, ArH), 7.66 (d, J=8.4 Hz, 1, ArH), 8.13 ppm (d, J=16.4 Hz, 1, C=CHCO).

Step 6: Ethyl (E)-4-[3-(1-adamantyl)-4-hydroxyphenyl]-2-chlorocinnamate.

A mixture of 1.30 g (2.46 mmol) of ethyl (E)-4-[3-(1-adamantyl)-4-benzyloxyphenyl]-2-chlorocinnamate was stirred in 30 ml of CH$_2$Cl$_2$ at −78° C. under Ar, and 8.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a pale-yellow solid (0.87 g, 81%): m.p. 231–233° C.; $R_f$ 0.31 (20% EtOAc/hexane); $^1$H NMR (300 MHz, CDCl$_3$) δ 1.80, 2.17 (2 s, 12, AdCH$_2$), 2.11 (s, 3, AdCH), 1.35 (t, J=7.1 Hz, 3 CH$_3$), 4.28 (q, J=7.1 Hz, 2, CH$_2$), 4.98 (s, 1, OH), 6.46 (d, J=16.4 Hz, 1, HC=CCO), 6.74 (d, J=8.4 Hz, 1, ArH), 7.30 (dd, J=7.8, 2.4 Hz, 1, ArH), 7.43 (d, J=2.0 Hz, 1, ArH), 7.46 (dd, J=8.0, 2.0 Hz, 1, ArH), 7.60 (d, J=2.0 Hz, 1, ArH), 7.66 (d, J=7.6 Hz, 1, ArH), 8.13 ppm (d, J=16.4 Hz, 1, C=CHCO).

Step 7: (E)-4-[3-(1-adamantyl)-4-hydroxyphenyl]-2-chlorocinnamic acid.

To a solution of 0.85 g (1.94 mmol) of ethyl (E)-4-[3-(1-adamantyl)-4-hydroxyphenyl]-2-chlorocinnamate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried ($MgSO_4$), filtered, and concentrated to afford a yellow solid (0.78 g, 97%): m.p. 276–278° C.; $R_f$ 0.19 (75% EtOAc/hexane); $^1$H NMR (400 MHz, DMSO-$d_6$) δ 1.74, 2.13 (2 s, 12, $AdCH_2$), 2.05 (s, 3, AdCH), 6.62 (d, J=15.6 Hz, 1, HC=CCO), 6.86 (d, J=8.0 Hz, 1, ArH), 7.38 (s, 1, ArH), 7.41 (dd, J=7.8, 2.0 Hz, 1, ArH), 7.60 (dd, J=8.8, 1.2 Hz, 1, ArH), 7.72 (d, J=2.0 Hz, 1, ArH), 7.89 (d, J=16.0 Hz, 1, C=CHCO), 7.94 (d, J=8.0 Hz, 1, ArH), 9.67 (s, 1, OH), 12.61 ppm (s, 1, $CO_2H$); MS (EIHR): calculated for $C_{25}H_{25}ClO_3$, 408.1492. found, 408.1482.

EXAMPLE 3

Synthesis of (E)-4-[3-(1-Adamantyl)-4-hydroxyphenyl]-3-methylcinnamic acid

Step 1: 4-Acetoxy-3-methylbenzaldehyde

A mixture of 5.20 g (38.2 mmol) of 4-hydroxy-3-methylbenzaldehyde, 5.0 ml (61.8 mmol) of pyridine in 40 ml of $CH_2Cl_2$ was stirred in a 0° C. ice bath, then 4.0 ml (42.3 mmol) of acetic anhydride was added over a period of 20 min. The reaction mixture was stirred for 1.5 hours more, then warmed to room temperature. The mixture was extracted with EtOAc, washed with 10% HCl, brine, and water, dried ($MgSO_4$), filtered, and concentrated to afford a yellowish oil (6.51 g, 95% yield): $R_f$ 0.28 (20% EtOAc/hexane); $^1$H NMR (400 MHz, $CDCl_3$) δ 2.27 (s, 3, $CH_3$), 2.36 (s, 3, $CH_3$), 7.20 (d, J=7.6 Hz, 1, ArH), 7.75 (dd, J=7.8,1.6 Hz, 1, ArH), 7.78 (s, 1, ArH), 9.96 ppm (s, 1, CHO).

Step 2: Ethyl (E)-4-acetoxy-3-methylcinnamate.

To a suspension of 6.37 g (35.7 mmol) of 4-acetoxy-3-methylbenzaldehyde and 15.00 g (108.5 mmol) of $K_2CO_3$ in 40 ml of anhydrous THF under Ar, 16.0 ml (71.3 mmol) of triethyl phosphonoacetate was added. The reaction mixture was stirred at room temperature for 4 days at which time the reaction was complete. The mixture was extracted with EtOAc, washed with brine and water, dried ($MgSO_4$), filtered, and concentrated. Flash column chromatography (20% EtOAc/hexane) yielded a white solid (8.38 g, 94% yield): m.p. 33–35° C.; $R_f$ 0.35 (20% EtOAc/hexane); $^1$H NMR (400 MHz, $CDCl_3$) δ 1.34 (t, J=7.6 Hz, 3, $CH_3$), 2.20 (s, 3, $ArCH_3$), 2.33 (s, 3, $CH_3CO$), 4.26 (q, J=7.6 Hz, 2, $CH_2$), 6.38 (d, J=15.6 Hz, 1, HC=CCO), 7.03 (d, J=7.6 Hz, 1, ArH), 7.38 (dd, J=7.6, 1.6 Hz, 1, ArH), 7.39 (s, 1, ArH), 7.63 ppm (d, J=16.4 Hz, 1, C=CHCO).

Step 3: Ethyl (E)-4-hydroxy-3-methylcinnamate.

To a solution of 8.33 g (33.5 mmol) of ethyl (E)-4-acetoxy-3-methylcinnamate in 50 ml of MeOH was added 9.30 g (67.2 mmol) of $K_2CO_3$. This mixture was stirred at room temperature for 4 hours, at which time the reaction was complete. The mixture was extracted with EtOAc, and the extract was washed with 10% HCl, brine, and water, dried ($MgSO_4$), filtered, and concentrated to afford a pale-brown solid (5.97 g, 86% yield): m.p. 79–81° C.; $R_f$ 0.26 (20% EtOAc/hexane); $^1$H NMR (400 MHz, $CDCl_3$) δ 1.33 (t, J=6.4 Hz, 3, $CH_3$), 2.26 (s, 3, $ArCH_3$), 4.25 (q, J=7.6 Hz, 2, $CH_2$), 5.36 (s, 1, OH), 6.29 (d, J=16.4 Hz, 1, HC=CCO), 6.78 (d, J=8.0 Hz, 1, ArH), 7.27 (dd, J=7.6, 1.6 Hz, 1, ArH), 7.32 (s, 1, ArH), 7.62 ppm (d, J=16.0 Hz, 1, C=CHCO).

Step 4: Ethyl (E)-3-methyl-4-(trifluoromethanesulfonyloxy)cinnamate

To a solution of 5.93 g (28.7 mmol) of ethyl (E)-4-hydroxy-3-methylcinnamate and 5.0 ml (61.8 mmol) of pyridine in 50 ml of $CH_2Cl_2$ in a 0° C. ice bath under Ar, 4.9 ml (29.1 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% $NaHCO_3$, brine, and water, dried ($MgSO_4$), filtered, and concentrated to afford a white solid (8.53 g, 88% yield): m.p. 38–40° C.; $R_f$ 0.48 (20% EtOAc/hexane); $^1$H NMR (400 MHz, $CDCl_3$) δ 1.34 (t, J=8.0 Hz, 3, $CH_3$), 2.40 (s, 3, $ArCH_3$), 4.27 (q, J=7.2 Hz, 2, $CH_2$), 6.43 (d, J=15.6 Hz, 1, HC=CCO), 7.26 (d, J=8.0 Hz, 1, ArH), 7.42 (dd, J=8.8, 2.0 Hz, 1, ArH), 7.45 (s, 1, ArH), 7.63 ppm (d, J=16.8 Hz, 1, C=CHCO).

Step 5: Ethyl (E)-4-[3-(1-adamantyl)-4-benzyloxyphenyl]-3-methylcinnamate

To a stirred suspension of 1.00 g (2.95 mmol) of ethyl (E)-3-methyl-4-(trifluoromethanesulfonyloxy)cinnamate, 1.10 g (3.03 mmol) of 3-(1-adamantyl)-4-benzyloxyphenylboronic acid [$^1$H NMR (300 MHz, $CDCl_3$) δ 1.77, 2.26 (2 s, 12, $AdCH_2$), 2.07 (s, 3, AdCH), 5.21 (s, 2, $CH_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of $Pd[P(C_6H_5)_3]_4$, and 0.26 g (6.1 mmol) of LiCl in 20 ml of DME was added under Ar 3 ml of 2.0 M aq. $Na_2CO_3$. The reaction mixture was heated at reflux (80–85° C.) overnight, at which time the reaction was complete. The mixture was extracted with EtOAc. The extract was washed with brine and water, dried ($MgSO_4$), filtered, and concentrated. Flash column chromatography (10% EtOAc/hexane) yielded a white solid (1.46 g, 97%): m.p. 123–125° C.; $R_f$ 0.66 (20% EtOAc/hexane); $^1$H NMR (300 MHz, $CDCl_3$) δ 1.73, 2.16 (2 s, 12, $AdCH_2$), 2.04 (s, 3, AdCH), 2.33 (s, 3, $ArCH_3$), 5.17 (s, 2, $CH_1$ 1.35 (t, J=7.2 Hz, 3 $CH_3$), 4.27 (q, J=7.6 Hz, 2, $CH_2$), 6.46 (d, J=16.0 Hz, 1 HC=CCO), 7.00 (d, J=8.8 Hz, 1, ArH), 7.13 (dd, J=8.0, 2.0 Hz, 1, ArH), 7.21 (d, J=2.8 Hz, 1, ArH), 7.28 (s, 1, ArH), 7.53 (d, J=7.2 Hz, 1, ArH), 7.3–7.5 (m, 6, ArH), 7.70 ppm (d, J=15.6 Hz, 1, C=CHCO).

Step 6: Ethyl (E)-4-[3-(1-adamantyl)-4-hydroxyphenyl]-3-methylcinnamate

A mixture of 1.44 g (2.84 mmol) of ethyl (E)-4-[3-(1-adamantyl)-4-benzyloxyphenyl]-3-methylcinnamate was stirred in 10 ml of $CH_2Cl_2$ at −78° C. under Ar while 8.0 ml of 1.0 M $BBr_3$ in $CH_2Cl_2$ was added slowly over a period of 0.5 hour. The reaction mixture was stirred for 2 hours more, at which time the reaction was complete. The mixture was extracted with EtOAc, washed with brine and water, dried ($MgSO_4$), filtered, and concentrated. Flash column chromatography (20% EtOAc/hexane) yielded a pale-yellow solid (0.86 g, 73%: m.p. 193–195° C.; $R_f$ 0.47 (20% EtOAc/hexane); $^1$H NMR (300 MHz, $CDCl_3$) δ 1.78, 2.14 (2 s, 12, $AdCH_2$), 2.09 (s, 3, AdCH), 1.35 (t, J=7.2 Hz, 3 $CH_3$), 2.31 (s, 3, $ArCH_3$), 4.27 (q, J=7.6 Hz, 2, $CH_2$), 4.94 (s, 1, OH), 6.46 (d, J=16.4 Hz, 1, HC=CCO), 6.71 (d, J=8.4 Hz, 1, ArH), 7.03 (dd, J=8.4, 1.6 Hz, 1, ArH), 7.16 (d, J=2.8 Hz, 1, ArH), 7.25 (s, 1, ArH), 7.39 (dd, J=9.2, 2.4 Hz, 1, ArH), 7.41 (s, 1, ArH), 7.71 ppm (d, J=16.0 Hz, 1, C=CHCO).

Step 7: (E)-4-[3-(1-Adamantyl)-4-hydroxyphenyl]-3-methylcinnamic acid

To a solution of 0.82 g (1.96 mmol) of ethyl (E)-4-[3-(1-adamantyl)-4-hydroxyphenyl]-3-methylcinnamate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried ($MgSO_4$), filtered, and concentrated to afford a pale-brown solid (0.70 g, 92%): m.p. 232–234° C.; $R_f$ 0.45 (75% EtOAc/hexane); $^1$H NMR (400 MHz, DMSO-$d_6$) δ 1.73, 2.09 (2 s, 12, $AdCH_2$), 2.03 (s, 3, AdCH), 2.27 (s, 3, $ArCH_3$), 6.51 (d, J=16.4 Hz, 1, HC=CCO), 6.83 (d, J=8.8 Hz, 1, ArH), 7.01 (d, J=1.6 Hz, 1, ArH), 7.03 (s, 1, ArH), 7.21 (d, J=8.0 Hz, 1, ArH), 7.52 (d, J=8.0 Hz, 1, ArH), 7.57 (d, J=15.2 Hz, 1, C=CHCO), 7.58 (s, 1, ArH), 9.45 (s, 1, OH), 12.37 ppm (s, 1, $CO_2H$); MS [fast-atom-bombardment high-resolution (FABHR)]: calculated for $C_{26}H_{28}O_3$, 388.2038. found, 388.2046.

EXAMPLE 4

Synthesis of (E)-4-[3-(1-Adamantyl)-4-hydroxyphenyl]-3,5-dimethylcinnamic acid

Step 1: 4-Acetoxy-3,5-dimethylbenzaldehyde

A mixture of 3.36 g (22.4 mmol) of 3,5-dimethyl-4-hydroxybenzaldehyde and 3.0 ml (37.1 mmol) of pyridine in 40 ml of $CH_2Cl_2$ was stirred in a 0° C. ice bath, then 3.0 ml (37.1 mmol) of acetic anhydride was added over a period of 20 min. The reaction mixture was stirred for 1.5 hours more, then warmed to room temperature. The mixture was extracted with EtOAc, washed with 10% HCl, brine, and water, dried ($MgSO_4$), filtered, and concentrated to afford a pale-yellow solid (4.00 g, 93% yield): $R_f$ 0.33 (20% EtOAc/hexane); $^1$H NMR (400 MHz, $CDCl_3$) δ 2.24 (s, 6, $ArCH_3$), 2.38 (s, 3, $CH_3$), 7.61 (s, 2, ArH), 9.93 ppm (s, 1, CHO).

Step 2: Ethyl (E)-4-acetoxy-3,5-dimethylcinnamate.

To a suspension of 3.87 g (20.1 mmol) of 4-acetoxy-3,5-dimethyl-benzaldehyde and 8.30 g (60.0 mmol) of $K_2CO_3$ in 50 ml of anhydrous THF under Ar, 9.0 ml (40.0 mmol) of triethyl phosphonoacetate was added. The reaction mixture was stirred at room temperature for 4 days at which time the reaction was complete. The mixture was extracted with EtOAc, washed with brine and water, dried ($MgSO_4$), filtered, and concentrated. Flash column chromatography (15% EtOAc/hexane) yielded a white solid (3.45 g, 65% yield): m.p. 65–67° C.; $R_f$ 0.37 (20% EtOAc/hexane); $^1$H NMR (400 MHz, $CDCl_3$) δ 1.33 (t, J=7.6 Hz, 3, $CH_3$), 2.17 (s, 6, $ArCH_3$), 2.34 (s, 3, $CH_3$), 4.25 (q, J=8.0 Hz, 2, $CH_2$), 6.36 (d, J=16.4 Hz, 1, HC=CCO), 7.24 (s, 2, ArH), 7.60 ppm (d, J=15.6 Hz, 1, C=CHCO).

Step 3: Ethyl (E)-3,5-dimethyl-4-hydroxycinnamate.

To a solution of 3.38 g (12.9 mmol) of ethyl (E)-4-acetoxy-3,5-dimethylcinnamate in 50 ml of MeOH was added 4.00 g (28.9 mmol) of $K_2CO_3$. This mixture was stirred at room temperature for 4 hours, at which time the reaction was complete. The mixture was extracted with EtOAc, and the extract was washed with 10% HCl, brine, and water, dried ($MgSO_4$), filtered, and concentrated to afford a white solid (2.52 g, 89% yield): m.p. 82–84° C.; $R_f$ 0.22 (20% EtOAc/hexane); $^1$H NMR (400 MHz, $CDCl_3$) δ 1.33 (t, J=7.2 Hz, 3, $CH_3$), 2.26 (s, 6, $ArCH_3$), 4.24 (q, J=7.2 Hz, 2, $CH_2$), 4.93 (d, J=4.4 Hz, 1, OH), 6.28 (d, J=16.0 Hz, 1, HC=CCO), 7.18 (s, 2, ArH), 7.58 ppm (d, J=16.0 Hz, 1, C=CHCO).

Step 4: Ethyl (E)-3,5-dimethyl-4-(trifluoromethanesulfonyloxy)cinnamate.

To a solution of 2.50 g (11.3 mmol) of ethyl (E)-3,5-dimethyl-4-hydroxycinnamate and 3.0 ml (37.1 mmol) of pyridine in 40 ml of $CH_2Cl_2$ in a 0° C. ice bath under Ar, 3.5 ml (20.8 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% $NaHCO_3$, brine, and water, dried ($MgSO_4$), filtered, and concentrated to afford a white solid (1.15 g, 28% yield): m.p. 78–80° C.; $R_f$ 0.53 (20% EtOAc/hexane); $^1$H NMR (400 MHz, $CDCl_3$) δ 1.34 (t, J=7.6 Hz, 3, $CH_3$), 2.40 (s, 6, $ArCH_3$), 4.27 (q, J=7.6 Hz, 2, $CH_2$), 6.40 (d, J=16.8 Hz, 1, HC=CCO), 7.28 (s, 2, ArH), 7.58 ppm (d, J=16.4 Hz, 1, C=CHCO).

Step 5: Ethyl (E)-4-[3-(1-adamantyl)-4-benzyloxyphenyl]-3,5-dimethylcinnamate.

To a stirred suspension of 1.12 g (3.17 mmol) of ethyl (E)-3,5-dimethyl-4-(trifluoromethanesulfonyloxy)cinnamate, 1.15 g (3.17 mmol) of 3-(1-adamantyl)-4-benzyloxyphenylboronic acid [$^1$H NMR (300 MHz, $CDCl_3$) δ 1.77, 2.26 (2 s, 12, $AdCH_2$), 2.07 (s, 3, AdCH), 5.21 (s, 2, $CH_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of $Pd[P(C_6H_5)_3]_4$, and 0.30 g (7.1 mmol) of LiCl in 20 ml of DME was added under Ar 3.5 ml of 2.0 M aq. $Na_2CO_3$. The reaction mixture was heated at reflux (80–85° C.) overnight, at which time the reaction was complete. The mixture was extracted with EtOAc. The extract was washed with brine and water, dried ($MgSO_4$), filtered, and concentrated. Flash column chromatography (10% EtOAc/hexane) yielded a white solid (1.19 g, 72%): m.p. 129–131° C.; $R_f$ 0.42 (20% EtOAc/hexane); $^1$H NMR (400 MHz, $CDCl_3$) δ 1.34 (t, J=7.2 Hz, 3 $CH_3$), 1.74 (s, 6, $AdCH_2$), 2.08 (s, 9, AdCH, $AdCH_2$), 2.14 (s, 6, $ArCH_3$), 4.27 (q, J=7.2 Hz, 2, $CH_2$), 5.16 (s, 2, $ArCH_2$), 6.44 (d, J=15.6 Hz, 1, HC=CCO), 6.91 (dd, J=7.6, 1.6 Hz, 1, ArH), 6.98 (d, J=2.0 Hz, 1, ArH), 7.01 (d, J=7.6 Hz, 1, ArH), 7.28 (s, 2, ArH), 7.3–7.6 (m, 5, ArH), 7.68 ppm (d, J=15.6 Hz, 1, C=CHCO).

Step 6: Ethyl (E)-4-[3-(1-adamantyl)-4-hydroxyphenyl]-3,5-dimethylcinnamate.

A mixture of 1.13 g (2.17 mmol) of ethyl (E)-4-[3-(1-adamantyl)-4-benzyloxyphenyl]-3,5-dimethylcinnamate was stirred in 10 ml of $CH_2Cl_2$ at −78° C. under Ar while 6.0 ml of 1.0 M $BBr_3$ in $CH_2Cl_2$ was added slowly over a period of 0.5 hour. The reaction mixture was stirred for 2 hours more, at which time the reaction was complete. The mixture was extracted with EtOAc, washed with brine and water, dried ($MgSO_4$), filtered, and concentrated. Flash column chromatography (20% EtOAc/hexane) yielded a pale-yellow solid (0.47 g, 51%): m.p. 198–200° C.; $R_f$ 0.34 (20% EtOAc/hexane); $^1$H NMR (400 MHz, $CDCl_3$) δ 1.35 (t, J=7.2 Hz, 3, $CH_3$), 1.77 (s, 6, $AdCH_2$), 2.06 (s, 9, AdCH, $AdCH_2$), 2.12 (s, 6, $ArCH_3$), 4.27 (q, J=7.2 Hz, 2, $CH_2$), 4.82 (s, 1, OH), 6.44 (d, J=15.6 Hz, 1, HC=CCO), 6.70 (d, J=7.6 Hz, 1, ArH), 6.81 (dd, J=8.0, 2.4 Hz, 1, ArH), 6.94 (d, J=2.0 Hz, 1, ArH), 7.27 (s, 2, ArH), 7.68 ppm (d, J=16.0 Hz, 1, C=CHCO).

Step 7: (E)-4-[3-(1-Adamantyl)-4-hydroxphenyl]-3,5-dimethylcinnamic acid

To a solution of 0.45 g (1.04 mmol) of ethyl (E)-4-[3-(1-adamantyl)-4-hydroxyphenyl]-3,5-dimethylcinnamate in 30 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a brown solid (0.39 g, 95%): m.p. 127–129° C.; R$_f$0.51 (1% HOAc/2% MeOH/CHCl$_3$); $^1$H NMR (400 MHz, DMSO-d$_6$) δ 1.72 (s, 6, AdCH$_2$), 1.98 (s, 9, AdCH, AdCH$_2$), 2.07 (s, 6, ArCH$_3$), 6.49 (d, J=16.0 Hz, 1, HC=CCO), 6.75 (d, J=1.6 Hz, 1, ArH), 6.76 (d, J=2.4 Hz, 1, ArH), 6.83 (d, J=9.2 Hz, 1, ArH), 7.40 (s, 2, ArH), 7.52 (d, J=16.0 Hz, 1, C=CHCO), 9.33 (s, 1, OH), 12.34 ppm (s, 1, CO$_2$H); MS (FABHR): calculated for C$_{27}$H$_{30}$O$_3$, 402.2195. found, 402.2196.

EXAMPLE 5

6-[3-(1-Adamantyl)-4-hydroxphenyl]-2,5,7,8-tetramethylchroman-2-carboxylic acid

Step 1: Ethyl 6-hydroxy-2,5,7,8-tetramethylchroman-2-carboxylate.

To a solution of 4.80 g (19.2 mmol) of 6-hydroxy-2,5,7,8-tetra-methylchroman-2-carboxylic acid in 80 ml of EtOH, 5.0 ml (93.8 mmol) of H$_2$SO$_4$ was added. The reaction mixture was stirred at 60–70° C. for 2 days at which time the reaction was complete. The mixture was extracted with EtOAc, washed with 5% NaHCO$_3$, brine and water, dried (MgSO$_4$), filtered, and concentrated. Flash column chromatography (20% EtOAc/hexane) yielded a white solid (5.09 g, 95%): m.p. 116–118° C.; R$_f$0.38 (20% EtOAc/hexane); $^1$H NMR (400 MHz, CDCl$_3$) δ 1.18 (t, J=6.8 Hz, 3, CH$_3$), 1.60 (s, 3, 2-CH$_3$), 1.83–1.90 (m, 1, CH), 2.06, 2.16, 2.18 (3 s, 9, ArCH$_3$), 2.40–2.45 (m, 1, CH), 2.48–2.65 (m, 1, CH), 2.61–2.67 (m, 1, CH), 4.11 ppm (q, J=6.8 Hz, 2, CH$_2$).

Step 2: Ethyl 2,5,7,8-tetramethyl-6-(trifluoromethanesulfonyloxy)chroman-2-carboxylate.

To a solution of 5.00 g (17.9 mmol) of ethyl 6-hydroxy-2,5,7,8-tetra-methylchroman-2-carboxylate and 5.0 ml (61.9 mmol) of pyridine in 40 ml of CH$_2$Cl$_2$ in a 0° C. ice bath under Ar, 5.1 ml (30.3 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% NaHCO$_3$, brine, and water, dried (MgSO$_4$), filtered, and concentrated to afford a yellow oil (7.17 g, 97% yield): R$_f$0.63 (20% EtOAc/hexane); $^1$H NMR (400 MHz, CDCl$_3$) δ 1.17 (t, J=7.2 Hz, 3, CH$_3$), 1.63 (s, 3, 2-CH$_3$), 1.63–1.91 (m, 1, CH), 2.15, 2.19, 2.24 (3 s, 9, ArCH$_3$), 2.42–2.51 (m, 2, CH$_2$), 2.61–2.67 (m, 1, CH), 4.13 ppm (q, J=7.2 Hz, 2, CH$_2$).

Step 3: Ethyl 6-[3-(1-adamantyl)-4-benzyloxyphenyl]-2,5,7,8-tetramethylchroman-2-carboxylate.

To a stirred suspension of 1.32 g (3.21 mmol) of ethyl 2,5,7,8-tetra-methyl-6-(trifluoromethanesulfonyloxy)chroman-2-carboxylate, 1.20 g (3.31 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C$_6$H$_5$)$_3$]$_4$, and 0.30 g (7.1 mmol) of LiCl in 20 ml of anhydrous DME was added under Ar 3.5 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a yellow oil (1.62 g, 87%): R$_f$0.64 (20% EtOAc/hexane); $^1$H NMR (400 MHz, CDCl$_3$) δ 1.71, 2.14 (2 s, 12, AdCH$_2$), 2.02 (s, 3, AdCH), 1.18 (t, J=7.6 Hz, 3 CH$_3$), 1.63 (s, 3, 2-CH$_3$), 1.86–1.94 (m, 1, CH), 1.84, 1.93, 2.24 (3 s, 9, ArCH$_3$), 2.42–2.53 (m, 2, CH$_2$), 2.62–2.67 (m, 1, CH), 4.15 (q, J=7.6 Hz, 2, CH$_2$), 5.14 (s, 2, CH$_2$), 6.86–6.99 (m, 3, ArH), 7.32–7.56 ppm (m, 5, ArH).

Step 4: Ethyl 6-[3-(1-adamantyl)-4-hydroxyphenyl]-2,5,7,8-tetramethylchroman-2-carboxylate.

A mixture of 1.58 g (2.72 mmol) of ethyl 6-[3-(1-adamantyl)-4-benzyloxyphenyl]-2,5,7,8-tetramethylchroman-2-carboxylate was stirred in 10 ml of CH$_2$Cl$_2$ at −78° C. under Ar while 8.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (10% EtOAc/hexane) yielded a pink solid (0.58 g, 43%): m.p. 199–201° C.; R$_f$0.42 (20% EtOAc/hexane); $^1$H NMR (400 MHz, CDCl$_3$) δ 1.77, 2.11 (2 s, 12, AdCH$_2$), 2.06 (s, 3, AdCH), 1.23 (t, J=7.2 Hz, 3, CH$_3$), 1.64 (s, 3, 2-CH$_3$), 1.85–1.95 (m, 1, CH), 1.82, 1.92, 221 (3 s, 9, ArCH$_3$), 2.40–2.55 (m, 2, CH$_2$), 2.62–2.70 (m, 1, CH), 4.16 (q, J=7.2 Hz, 2, CH$_2$), 4.70 (s, 1, OH), 6.65 (d, J=8.0 Hz, 1, ArH), 6.75–6.78 (m, 1, ArH), 6.91 ppm (dd, J=6.8, 2.0 Hz, 1, ArH).

Step 5: 6-[3-(1-Adamantyl)-4-hydroxphenyl]-2,5,7,8-tetramethylchroman-2-carboxylic acid.

To a solution of 0.56 g (1.15 mmol) of ethyl 6-[3-(1-adamantyl)-4-hydroxyphenyl]-2,5,7,8-tetramethylchroman-2-carboxylate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a brown solid (0.48 g, 90%): m.p. 168–170° C.; R$_f$0.14 (75% EtOAc/hexane); $^1$H NMR (400 MHz, DMSO-d$_6$) δ 1.71, 2.06 (2 s, 12, AdCH$_2$), 2.01 (s, 3, AdCH), 1.55 (s, 3, 2-CH$_3$), 1.76–1.82 (m, 1, CH), 1.76, 1.82, 2.07 (3 s, 9, ArCH$_3$), 2.33–2.37 (m, 2, CH$_2$), 2.50–2.60 (m, 1, CH), 6.67 (s, 1, ArH), 6.62–6.67 (m, 1, ArH), 6.78 (dd, J=8.0, 1.6 Hz, 1, ArH), 9.20 (s, 1, OH), 12.76 ppm (s, 1, CO$_2$H); MS (FABHR): calculated for C$_{30}$H$_{36}$O$_4$, 460.2614. found, 460.2621.

EXAMPLE 6

5-[3-(1-Adamantyl)-4-hydroxphenyl]indole-2-carboxylic acid

Step 1: Ethyl 5-methoxyindole-2-carboxylate.

To a solution of 4.80 g (25.1 mmol) of 5-methoxyindole-2-carboxylic acid in 80 ml of EtOH, 5.0 ml (93.8 mmol) of H$_2$SO$_4$ was added. The reaction mixture was stirred at 60–70° C. for 2 days at which time the reaction was complete. The mixture was extracted with EtOAc, washed with 5% NaHCO$_3$, brine and water, dried (MgSO$_4$), filtered, and concentrated. Flash column chromatography (20% EtOAc/hexane) yielded a brown solid (5.42 g, 98%): m.p. 151–153° C.; R$_f$ 0.42 (20% EtOAc/hexane); $^1$H NMR (400 MHz, CDCl$_3$) δ 1.41 (t, J=7.6 Hz, 3, CH$_3$), 3.85 (s, 3, OCH$_3$), 4.41 (q, J=7.6 Hz, 2, CH$_2$), 7.00 (dd, J=9.6, 2.4 Hz, 1, ArH), 7.07 (d, J=2.4 Hz, 1, ArH), 7.14 (d, J=1.2 Hz, 1, ArH), 7.31 (d, J=9.6 Hz, 1, ArH), 8.89 ppm (s, 1, NH).

Step 2: Ethyl 5-hydroxyindole-2-carboxylate.

A mixture of 5.34 g (24.3 mmol) of ethyl 5-methoxyindole-2-carboxylate was stirred in 40 ml of CH$_2$Cl$_2$ at 0° C. under Ar while 40.0 ml of 1.0 M BBr$_3$ in CH$_2$Cl$_2$ was added slowly over a period of 0.5 hour. The reaction mixture was stirred for 2 hours more at which time the reaction was complete. The mixture was extracted with EtOAc, washed with brine and water, dried (MgSO$_4$), filtered, and concentrated. Flash column chromatography (30% EtOAc/hexane) yielded a pale-yellow solid (4.07 g, 82%): m.p. 142–144° C.; R$_f$ 0.18 (20% EtOAc/hexane); $^1$H NMR (400 MHz, CDCl$_3$) δ 1.41 (t, J=7.2 Hz, 3, CH$_3$), 4.40 (q, J=7.2 Hz, 2, CH$_2$), 4.70 (s, 1, OH), 6.93 (dd, J=8.4, 1.6 Hz, 1, ArH), 7.06 (d, J=2.8 Hz, 1, ArH), 7.10 (s, 1, ArH), 7.29 (d, J=9.2 Hz, 1, ArH), 8.79 ppm (s, 1, NH).

Step 3: Ethyl 5-(trifluoromethanesulfonyloxy)indole-2-carboxylate.

To a solution of 4.00 g (19.5 mmol) of ethyl 5-hydroxyindole-2-carboxylate and 4.0 ml (49.5 mmol) of pyridine in 40 ml of CH$_2$Cl$_2$ in a 0° C. ice bath under Ar, 4.2 ml (24.9 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% NaHCO$_3$, brine, and water, dried (MgSO$_4$), filtered, and concentrated to afford a yellow solid (4.89 g, 74% yield): m.p. 122–124° C.; R$_f$ 0.38 (20% EtOAc/hexane); $^1$H NMR (400 MHz, CDCl$_3$) δ 1.43 (t, J=7.6 Hz, 3, CH$_3$), 4.44 (q, J=7.6 Hz, 2, CH$_2$), 7.23 (dd, J=9.6, 2.4 Hz, 1, ArH), 7.25 (d, J=2.0 Hz, 1, ArH), 7.47 (d, J=9.2 Hz, ArH), 7.61 (d, J=2.0 Hz, 1, ArH), 9.23 ppm (s, 1, NH).

Step 4: Ethyl 5-[3-(1-adamantyl)-4-benzyloxyphenyl]indole-2-carboxylate.

To a stirred suspension of 1.00 g (2.96 mmol) of ethyl 5-(trifluoromethanesulfonyloxy)indole-2-carboxylate, 1.10 g (3.03 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C$_6$H$_5$)$_3$]$_4$ and 0.30 g (7.1 mmol) of LiCl in 20 ml of DME was added under Ar 3.5 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (15% EtOAc/hexane) yielded a yellow solid (0.38 g, 25%): m.p. 187–189° C.; R$_f$ 0.40 (20% EtOAc/hexane); $^1$H NMR (400 MHz, CDCl$_3$) δ 1.75, 2.23 (2 s, 12, AdCH$_2$), 2.07 (s, 3, AdCH), 1.43 (t, J=7.2 Hz, 3 CH$_3$), 4.42 (q, J=7.6 Hz, 2, CH$_2$), 5.18 (s, 2, CH$_2$), 7.02 (d, J=8.0 Hz, 1, ArH), 7.32–7.58 (m, 10, ArH), 7.83 (s, 1, ArH), 8.86 ppm (s, 1, NH).

Step 5: Ethyl 5-[3-(1-adamantyl)-4-hydroxphenyl]indole-2-carboxylate.

A mixture of 0.36 g (0.71 mmol) of ethyl 5-[3-(1-adamantyl)-4-benzyloxyphenyl]indole-2-carboxylate was stirred in 10 ml of CH$_2$Cl$_2$ at −78° C. under Ar while 3.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a pale-yellow solid (0.22 g, 75%): m.p. 125–127° C.; R$_f$ 0.17 (20% EtOAc/hexane); $^1$H NMR (400 MHz, CDCl$_3$) δ 1.81, 2.21 (2 s, 12, AdCH$_2$), 2.11 (s, 3, AdCH), 1.43 (t, J=7.6 Hz, 3 CH$_3$), 4.42 (q, J=7.2 Hz, 2, CH$_2$), 4.80 (s, 1, OH), 6.74 (d, J=8.4 Hz, 1, ArH), 7.25 (s, 1, ArH), 7.32 (dd, J=8.0, 2.4 Hz, 1, ArH), 7.45 (d, J=8.4 Hz, 1, ArH), 7.48 (d, J=2.0 Hz, 1, ArH), 7.53 (dd, J=8.4, 2.0 Hz, 1, ArH), 7.82 (s, 1, ArH), 8.84 ppm (s, 1, NH), Step 6: 5-[3-(1-Adamantyl)-4-hydroxphenyl]indole-2-carboxylic acid.

To a solution of 0.20 g (0.48 mmol) of ethyl 5-[3-(1-adamantyl)-4-hydroxyphenyl]indole-2-carboxylate in 30 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a yellow solid (0.17 g, 91%): m.p. 275–277° C.; R$_f$ 0.35 (1% HOAc/2% MeOH/CHCl$_3$); $^1$H NMR (400 MHz, DMSO-d$_6$) δ 1.75, 2.15 (2 s, 12, AdCH$_2$), 2.05 (s, 3, AdCH), 6.67 (s, 1, ArH), 6.83 (d, J=8.8 Hz, 1, ArH), 7.24 (d, J=7.6 Hz, 1, ArH), 7.25 (d, J=7.6 Hz, 1, ArH), 7.31 (s, 1, ArH), 7.40 (d, J=8.4 Hz, 1, ArH), 7.62 (s, 1, ArH), 9.35 (s, 1, OH), 10.99 ppm (s, 1, CO$_2$H); MS (FABHR): calcd. for C$_{25}$H$_{25}$NO$_3$, 387.1834. found, 387.1824.

EXAMPLE 7

3"-(1-Adamantyl)-4"-hydroxy[1", 4',1', 1]terphenyl-4-carboxylic acid

Step 1: Ethyl 4'-(trifluoromethanesulfonyloxy)[1', 1]biphenyl-4-carboxylate.

To a solution of 5.26 g (21.7 mmol) of ethyl 4'-hydroxy-4-biphenyl-carboxylate and 4.0 ml (49.5 mmol) of pyridine in 40 ml of CH$_2$Cl$_2$ in a 0° C. ice bath under Ar, 4.2 ml (24.9 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% NaHCO$_3$, brine, and water, dried (MgSO$_4$), filtered, and concentrated to afford a white solid (8.00 g, 98% yield): m.p. 63–65° C.; R$_f$ 0.59 (20% EtOAc/hexane); $^1$H NMR (400 MHz, CDCl$_3$) δ 1.42 (t, J=7.2 Hz, 3, CH$_3$), 4.41 (q, J=7.2 Hz, 2, CH$_2$), 7.38 (d, J=8.8 Hz, 2, ArH), 7.63 (d, J=8.0 Hz, 2, ArH), 7.69 (d, J=8.4 Hz, 2, ArH), 9.14 ppm (d, J=8.0 Hz, 2, ArH).

Step 2: Ethyl 3"-(1-adamantyl)-4"-benzyloxy[1", 4', 1', 1]terphenyl-4-carboxylate.

To a stirred suspension of 1.00 g (2.67 mmol) of ethyl 4'-(trifluoromethanesulfonyloxy)[1', 1]-biphenyl-4-carboxylate, 0.97 g (2.67 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C$_6$H$_5$)$_3$]$_4$ and 0.30 g (7.1 mmol) of LiCl in 20 ml of DME was added under Ar 3.5 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a white solid (1.34 g, 92%): m.p. 154–156° C.; R$_f$0.63 (20% EtOAc/hexane); $^1$H NMR (400 MHz, CDCl$_3$) δ 1.75, 2.22 (2 s, 12, AdCH$_2$), 2.07 (s, 3, AdCH), 1.42 (t, J=7.2 Hz, 3CH$_3$), 4.41 (q, J=7.6 Hz, 2, CH$_2$), 5.18 (s, 2, CH$_2$), 7.03 (d, J=8.4 Hz, 1, ArH), 7.33–7.36 (m, 1, ArH), 7.40–7.46 (m, 3, ArH), 7.51–7.55 (m, 3, ArH), 7.68 (d, J=1.6 Hz, 4, ArH), 7.70 (d, J=8.4 Hz, 2, ArH), 8.12 ppm (d, J=8.4 Hz, 2, ArH).

Step 3: Ethyl 3"-(1-adamantyl)-4"-hydroxy[1",4',1',1]terphenyl-4-carboxylate.

A mixture of 1.30 g (2.39 mmol) of ethyl 3"-(1-adamantyl)-4"-benzyloxy[1", 4', 1', 1]terphenyl-4-carboxylate was stirred in 10 ml of CH$_2$Cl$_2$ at –78° C. under Ar while 6.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a white solid (0.89 g, 93%): m.p. 184–186° C.; R$_f$0.36 (20% EtOAc/hexane); $^1$H NMR (400 MHz, CDCl$_3$) δ 1.81, 2.19 (2 s, 12, AdCH$_2$), 2.12 (s, 3, AdCH), 1.42 (t, J=7.2 Hz, 3 CH$_3$), 4.41 (q, J=7.2 Hz, 2, CH$_2$), 4.90 (s, 1, OH), 6.75 (d, J=8.4 Hz, 1, ArH), 7.35 (dd, J=8.4, 2.0 Hz, 1, ArH), 7.50 (d, J=2.4 Hz, 1, ArH), 7.63–7.72 (m, 6, ArH), 8.12 ppm (d, J=8.8 Hz, 2, ArH).

Step 4: 3"-(1-Adamantyl)-4"-hydroxy[1", 4', 1', 1]terphenyl-4-carboxylic acid.

To a solution of 0.85 g (1.87 mmol) of ethyl 3"-(1-adamantyl)-4"-hydroxy[1", 4', 1', 1]terphenyl-4-carboxylate in 30 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a white solid (0.75 g, 94%): m.p. 305–307° C.; R$_f$0.55 (1% HOAc/2% MeOH/CHCl$_3$); $^1$H NMR (400 MHz, DMSO-d$_6$) δ 1.75, 2.15 (2 s, 12, AdCH$_2$), 2.06 (s, 3, AdCH), 6.87 (d, J=8.4 Hz, 1, ArH), 7.37 (d, J=1.6 Hz, 1, ArH), 7.39 (s, 1, ArH), 7.69 (d, J=8.8 Hz, 2, ArH), 7.78 (d, J=8.8 Hz, 2, ArH), 7.83 (d, J=9.2 Hz, 2, ArH), 8.02 (d, J=8.0 Hz, 2, ArH), 9.52 (s, 1, OH), 12.98 ppm (s, 1, CO$_2$H); MS (EIHR): calcd. for C$_{29}$H$_{28}$O$_3$, 424.2038. found, 424.2036.

EXAMPLE 8

(E)-4-[3-(1-Adamantyl)-4-hydroxphenyl]-3,5-dimethoxycinnamic acid

Step 1 Ethyl (E)-3,5-dimethoxy-4-hydroxycinnamate.

To a solution of 4.91 g (21.9 mmol) of 3,5-dimethoxy-4-hydroxycinnamic acid (Sigma) in 80 ml of EtOH, 5.0 ml (93.8 mmol) of H$_2$SO$_4$ was added. The reaction mixture was stirred at 60–70° C. for 2 days at which time the reaction was complete. The mixture was extracted with EtOAc, washed with 5% NaHCO$_3$, brine and water, dried (MgSO$_4$), filtered, and concentrated. Flash column chromatography (30% EtOAc/hexane) yielded a white solid (2.65 g, 48%): m.p. 56–58° C.; R$_f$0.41 (40% EtOAc/hexane). $^1$H NMR (400 MHz, CDCl$_3$) δ 1.34 (t, J=7.2 Hz, 3, CH$_3$), 3.92 (s, 6, OCH$_3$), 4.26 (q, J=7.2 Hz, 2, CH$_2$), 5.77 (s, 1, OH), 6.30 (d, J=16.0 Hz, 1, HC=CCO), 6.77 (s, 2, ArH), 7.59 ppm (d, J=16.0 Hz, 1, C=CHCO).

Step 2: Ethyl (E)-3,5-dimethoxy-4-(trifluoromethanesulfonyloxy)cinnamate.

To a solution of 2.60 g (10.3 mmol) of ethyl (E)-3,5-dimethoxy-4-hydroxycinnamate and 3.0 ml (37.1 mmol) of pyridine in 40 ml of CH$_2$Cl$_2$ in a 0° C. ice bath under Ar, 3.5 ml (20.8 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% NaHCO$_3$, brine, and water, dried (MgSO$_4$), filtered, and concentrated to afford a white solid (3.80 g, 95% yield): m.p. 89–91° C.; R$_f$0.36 (20% EtOAc/hexane); $^1$H NMR (400 MHz, CDCl$_3$) δ 1.35 (t, J=7.6 Hz, 3, CH$_3$), 3.92 (s, 6, OCH$_3$), 4.28 (q, J=7.6 Hz, 2, CH$_2$), 6.41 (d, J=16.0 Hz, 1, HC=CCO), 6.77 (s, 2, ArH), 7.59 ppm (d, J=16.4 Hz, 1, C=CHCO).

Step 3: Ethyl (E)-4-[3-(1-adamantyl)-4-benzyloxyphenyl]-3,5-dimethoxycinnamate.

To a stirred suspension of 1.00 g (2.60 mmol) of ethyl (E)-3,5-dimethoxy-4-(trifluoromethanesulfonyloxy)cinnamate, 0.95 g (2.62 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C$_6$H$_5$)$_3$]$_4$ and 0.30 g (7.1 mmol) of LiCl in 20 ml of DME was added under Ar 3.5 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a pale-yellow solid (0.21 g, 15%): m.p. 88–90° C.; R$_f$0.62 (20% EtOAc/hexane); $^1$H NMR (400 MHz, CDCl$_3$) δ 1.77, 2.09 (2 s, 12, AdCH$_2$), 2.05 (s, 3, AdCH), 1.35 (t, J=7.2 Hz, 3 CH$_3$), 3.83 (s, 6, OCH$_3$), 4.28 (q, J=7.2 Hz, 2, CH$_2$), 5.18 (s, 2, CH$_2$), 6.46 (d, J=16.0 Hz, 1, HC=CCO), 6.71 (s, 2, ArH), 6.90–7.55 (m, 8, ArH), 7.68 ppm (d, J=16.0 Hz, 1, C=CHCO).

Step 4: Ethyl (E)-4-[3-(1-adamantyl)-4-hydroxphenyl]-3,5-dimethoxycinnamate.

A mixture of 0.20 g (0.38 mmol) of ethyl (E)-4-[3-(1-adamantyl)-4-benzyloxyphenyl]-3,5-dimethoxycinnamate was stirred in 10 ml of CH$_2$Cl$_2$ at –78° C. under Ar while 2.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a pale-yellow solid (0.11 g, 63%): m.p. 175–177° C.; R$_f$0.20 (20% EtOAc/hexane); $^1$H NMR (400 MHz, CDCl$_3$) δ 1.77, 2.09 (2 s, 12, AdCH$_2$), 2.05 (s, 3, AdCH), 1.35 (t, J=7.2 Hz, 3 CH$_3$), 3.83 (s, 6, OCH$_3$), 4.28 (q, J=7.2 Hz, 2, CH$_2$), 4.79 (s, 1, OH), 6.46 (d, J=16.0 Hz, 1, HC=CCO), 6.68 (d, J=8.4 Hz, 1, ArH), 6.71 (s, 2, ArH), 7.08 (dd, J=8.4, 2.4 Hz, 1, ArH), 7.22 (d, J=2.0 Hz, 1, ArH), 7.68 (d, J=16.0 Hz, 1, C=CHCO).

Step 5: (E)-4-[3-(1-Adamantyl)-4-hydroxphenyl]-3,5-dimethoxycinnamic acid.

To a solution of 0.10 g (0.22 mmol) of ethyl (E)-4-[3-(1-adamantyl)-4-hydroxyphenyl]-3,5-dimethoxycinnamate in 30 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried ($MgSO_4$), filtered, and concentrated to afford a brown solid (0.05 g, 53%): m.p. 150–152° C.; $R_f$ 0.35 (1% HOAc/2% MeOH/$CHCl_3$); $^1$H NMR (400 MHz, DMSO-$d_6$) δ 1.72, 2.06 (2 s, 12, $AdCH_2$), 2.02 (s, 3, AdCH), 3.70 (s, 6, $OCH_3$), 6.63 (d, J=16.0 Hz, 1, HC=CCO), 6.73 (d, J=7.6 Hz, 1, ArH), 6.86 (dd, J=7.6, 1.6 Hz, 1, ArH), 6.93 (d, J=1.6 Hz, 1, ArH), 7.04 (s, 2, ArH), 7.58 (d, J=16.0 Hz, 1, C=CHCO), 9.24 (s, 1, OH), 12.36 ppm (s, 1, $CO_2H$); MS (FABHR): calcd. for $C_{27}H_{30}O_5$, 434.2093. found, 434.2099.

EXAMPLE 9

(E)-3-[3-(1-Adamantyl)-4-hydroxphenyl]cinnamic acid

Step 1: Ethyl (E)-3-hydroxycinnamate.

To a solution of 5.00 g (30.5 mmol) of 3-hydroxycinnamic acid in 50 ml of EtOH, 5.0 ml (93.8 mmol) of $H_2SO_4$ was added. The reaction mixture was stirred at 60–70° C. for 2 days at which time the reaction was complete. The mixture was extracted with EtOAc, washed with 5% $NaHCO_3$, brine and water, dried ($MgSO_4$), filtered, and concentrated. Flash column chromatography (10% EtOAc/hexane) yielded a white solid (4.87 g, 83%): m.p. 58–60° C.; $R_f$ 0.36 (20% EtOAc/hexane). $^1$H NMR (400 MHz, $CDCl_3$) δ 1.33 (t, J=8.0 Hz, 3, $CH_3$), 4.26 (q, J=7.6 Hz, 2, $CH_2$), 5.25 (s, 1, OH), 6.40 (d, J=15.6 Hz, 1, HC=CCO), 6.86 (dd, J=2.4, 8.0 Hz, 1, ArH), 7.00 (s, 1, ArH), 7.09 (d, J=7.6 Hz, 1, ArH), 7.25 (t, J=8.0 Hz, 1, ArH), 7.62 ppm (d, J=15.6 Hz, 1, C=CHCO).

Step 2: Ethyl (E)-3-(trifluoromethanesulfonyloxy)cinnamate.

To a solution of 4.80 g (24.9 mmol) of ethyl (E)-3-hydroxycinnamate and 3.0 ml (37.1 mmol) of pyridine in 50 ml of $CH_2Cl_2$ in a 0° C. ice bath under Ar, 5.0 ml (29.7 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% $NaHCO_3$, brine, and water, dried ($MgSO_4$), filtered, and concentrated. Flash column chromatography (10% EtOAc/hexane) yielded a white solid (7.75 g, 91%): m.p. 46–48° C.; $R_f$ 0.66 (20% EtOAc/hexane); $^1$H NMR (400 MHz, $CDCl_3$) δ 1.34 (t, J=7.2 Hz, 3, $CH_3$), 4.27 (q, J=7.2 Hz, 2, $CH_2$), 6.46 (d, J=16.0 Hz, 1, HC=CCO), 7.28 (dd, J=2.8, 8.0 Hz, 1, ArH), 7.40 (s, 1, ArH), 7.47 (t, J=8.0 Hz, 1, ArH), 7.53 (t, J=7.2 Hz, 1, ArH), 7.64 ppm (d, J=16.0 Hz, 1, C=CHCO).

Step 3: Ethyl (E)-3-[3-(1-adamantyl)-4-benzyloxyphenyl]cinnamate.

To a stirred suspension of 1.00 g (2.93 mmol) of ethyl (E)-3-(trifluoromethanesulfonyloxy)cinnamate, 1.07 g (2.95 mmol) of 3-(1-adamantyl)-4-benzyloxyphenylboronic acid [$^1$H NMR (300 MHz, $CDCl_3$) δ 1.77, 2.26 (2 s, 12, $AdCH_2$), 2.07 (s, 3, AdCH), 5.21 (s, 2, $CH_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P($C_6H_5$)$_3$]$_4$ and 0.30 g (7.1 mmol) of LiCl in 20 ml of DME was added under Ar 3.5 ml of 2.0 M aq. $Na_2CO_3$. The reaction mixture was heated at reflux (80–85° C.) overnight, at which time the reaction was complete. The mixture was extracted with EtOAc. The extract was washed with brine and water, dried ($MgSO_4$), filtered, and concentrated. Flash column chromatography (10% EtOAc/hexane) yielded a white solid (1.40 g, 97%): m.p. 53–55° C.; $R_f$ 0.60 (20% EtOAc/hexane); $^1$H NMR (400 MHz, $CDCl_3$) δ 1.74, 2.20 (2 s, 12, $AdCH_2$), 2.06 (s, 3, AdCH), 1.35 (t, J=6.8 Hz, 3 $CH_3$), 4.27 (q, J=7.6 Hz, 2, $CH_2$), 5.17 (s, 2, $CH_2$), 6.49 (d, J=15.6 Hz, 1, HC=CCO), 7.01 (d, J=8.8 Hz, 1, ArH), 7.34–7.58 (m, 10, ArH), 7.68 (s, 1, ArH), 7.74 ppm (d, J=15.6 Hz, 1, C=CHCO).

Step 4: Ethyl (E)-3-[3-(1-adamantyl)-4-hydroxphenyl]cinnamate.

A mixture of 1.35 g (2.74 mmol) of ethyl (E)-3-[3-(1-adamantyl)-4-benzyloxyphenyl]cinnamate was stirred in 20 ml of $CH_2Cl_2$ at −78° C. under Ar while 9.0 ml of 1.0 M $BBr_3$ in $CH_2Cl_2$ was added slowly over a period of 0.5 hour. The reaction mixture was stirred for 2 hours more, at which time the reaction was complete. The mixture was extracted with EtOAc, washed with brine and water, dried ($MgSO_4$), filtered, and concentrated. Flash column chromatography (10% EtOAc/hexane) yielded a white solid (0.94 g, 85%): m.p. 191–193° C.; $R_f$ 0.52 (20% EtOAc/hexane); $^1$H NMR (400 MHz, $CDCl_3$) δ 1.80, 2.17 (2 s, 12, $AdCH_2$), 2.10 (s, 3, AdCH), 1.35 (t, J=7.2 Hz, 3 $CH_3$), 4.27 (q, J=7.6 Hz, 2, $CH_2$), 4.86 (s, 1, OH), 6.48 (d, J=16.4 Hz, 1, HC=CCO), 6.73 (d, J=8.4 Hz, 1, ArH), 7.28 (dd, J=8.4, 2.0 Hz, 1, ArH), 7.39–7.46 (m, 3, ArH), 7.66 (s, 1, ArH), 7.74 ppm (d, J=16.4 Hz, 1, C=CHCO).

Step 5: (E)-3-[3-(1-Adamantyl)-4-hydroxphenyl]cinnamic acid.

To a solution of 0.92 g (2.29 mmol) of ethyl (E)-3-[3-(1-adamantyl)-4-hydroxyphenyl]cinnamate in 60 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried ($MgSO_4$), filtered, and concentrated to afford a off-white solid (0.71 g, 83%): m.p. 253–255° C.; $R_f$ 0.45 (EtOAc); $^1$H NMR (400 MHz, DMSO-$d_6$) δ 1.75, 2.14 (2 s, 12, $AdCH_2$), 2.06 (s, 3, AdCH), 6.61 (d, J=16.4 Hz, 1, HC=CCO), 6.85 (d, J=8.4 Hz, 1, ArH), 7.36 (d, J=2.8 Hz, 1, ArH), 7.37 (s, 1, ArH), 7.43 (t, J=7.6 Hz, 1, ArH), 7.59 (dd, J=7.6, 1.6 Hz, 2, ArH), 7.67 (d, J=16.4 Hz, 1, C=CHCO), 7.85 (s, 1, ArH), 9.48 (s, 1, OH), 12.41 ppm (s, 1, $CO_2H$); MS (FABHR): calcd. for $C_{25}H_{26}O_3$, 374.1882. found, 374.1879.

EXAMPLE 10

(E)-5-[3-(1-Adamantyl)-4-hydroxphenyl]-2-methoxycinnamic acid

Step 1: Ethyl (E)-5-bromo-2-methoxycinnamate.

To a suspension of 5.36 g (24.9 mmol) of 5-bromo-o-anisaldehyde and 12.14 g (87.8 mmol) of $K_2CO_3$ in 100 ml of anhydrous THF under Ar, 13.0 ml (65.5 mmol) of triethyl phosphonoacetate was added. The reaction mixture was stirred at room temperature for 4 days at which time the reaction was complete. The mixture was extracted with EtOAc, washed with brine and water, dried ($MgSO_4$), filtered, and concentrated. Flash column chromatography (10% EtOAc/hexane) yielded a white solid (6.80 g, 96%): m.p. 55–56° C.; $R_f$ 0.46 (20% EtOAc/hexane). $^1$H NMR (400 MHz, CDCl$_3$) δ 1.34 (t, J=7.2 Hz, 3, CH$_3$), 3.87 (s, 3, OCH$_3$), 4.26 (q, J=7.2 Hz, 2, CH$_2$), 6.49 (d, J=16.0 Hz, 1, HC=CCO), 6.79 (d, J=8.0 Hz, 1, ArH), 7.42 (dd, J=2.4, 8.8 Hz, 1, ArH), 7.61 (d, J=2.4 Hz, 1, ArH), 7.89 ppm (d, J=16.4 Hz, 1, C=CHCO).

Step 2: Ethyl (E)-5-[3-(1-adamantyl)-4-benzyloxyphenyl]-2-methoxycinnamate.

To a stirred suspension of 0.90 g (3.16 mmol) of ethyl (E)-5-bromo-2-methoxycinnamate, 1.17 g (3.23 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C$_6$H$_5$)$_3$]$_4$ and 0.30 g (7.1 mmol) of LiCl in 20 ml of DME was added under Ar 3.5 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a white solid (1.44 g, 87%): m.p. 120–122° C.; $R_f$ 0.54 (20% EtOAc/hexane); $^1$H NMR (400 MHz, CDCl$_3$) δ 1.74, 2.20 (2 s, 12, AdCH$_2$), 2.07 (s, 3, AdCH), 1.35 (t, J=6.8 Hz, 3 CH$_3$), 3.92 (s, 3, OCH$_3$), 4.28 (q, J=7.6 Hz, 2, CH$_2$), 5.17 (s, 2, CH$_2$), 6.60 (d, J=16.4 Hz, 1, HC=CCO), 6.96 (d, J=8.8 Hz, 1, ArH), 7.00 (d, J=8.4 Hz, 1, ArH), 7.32–7.54 (m, 8, ArH), 7.68 (d, J=2.4 Hz, 1, ArH), 8.03 ppm (d, J=16.4 Hz, 1, C=CHCO).

Step 3: Ethyl (E)-5-[3-(1-adamantyl)-4-hydroxphenyl]-2-methoxycinnamate.

A mixture of 1.40 g (2.68 mmol) of ethyl (E)-5-[3-(1-adamantyl)-4-benzyloxyphenyl]-2-methoxycinnamate was stirred in 20 ml of CH$_2$Cl$_2$ at –78° C. under Ar while 9.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a white solid (0.87 g, 75%): m.p. 180–182° C.; $R_f$ 0.29 (20% EtOAc/hexane); $^1$H NMR (400 MHz, CDCl$_3$) δ 1.80, 2.17 (2 s, 12, AdCH$_2$), 2.11 (s, 3, AdCH), 1.35 (t, J=7.2 Hz, 3 CH$_3$), 3.92 (s, 3, OCH$_3$), 4.28 (q, J=8.0 Hz, 2, CH$_2$), 4.82 (s, 1, OH), 6.59 (d, J=16.8 Hz, 1, HC=CCO), 6.71 (d, J=8.0 Hz, 1, ArH), 6.96 (d, J=9.2 Hz, 1, ArH), 7.23 (dd, J=8.0, 2.4 Hz, 1, ArH), 7.38 (d, J=2.4 Hz, 1, ArH), 7.51 (dd, J=8.4, 2.4 Hz, 1, ArH), 7.66 (d, J=2.8 Hz, 1, ArH), 8.03 ppm (d, J=16.4 Hz, 1, C=CHCO).

Step 4: (E)-5-[3-(1-Adamantyl)-4-hydroxyphenyl]-2-methoxycinnamic acid.

To a solution of 0.85 g (1.97 mmol) of ethyl (E)-5-[3-(1-adamantyl)-4-hydroxyphenyl]-2-methoxycinnamate in 20 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a off-white solid (0.71 g, 94%): m.p. 227–229° C.; $R_f$ 0.41 (EtOAc); $^1$H NMR (300 MHz, DMSO-d$_6$) δ 1.74, 2.13 (2 s, 12, AdCH$_2$), 2.05 (s, 3, AdCH), 3.85 (s, 3, OCH$_3$), 6.65 (d, J=15.6 Hz, 1, HC=CCO), 6.82 (d, J=7.8 Hz, 1, ArH), 7.11 (d, J=8.7 Hz, 1, ArH), 7.30 (d, J=7.8 Hz, 2, ArH), 7.57 (dd, J=8.7, 2.7 Hz, 1, ArH), 7.81 (d, J=2.7 Hz, 1, ArH), 7.85 (d, J=15.6 Hz, 1, C=CHCO), 9.38 (s, 1, OH), 12.40 ppm (s, 1, CO$_2$H); MS (FABHR): calcd. for C$_{26}$H$_{28}$O$_4$, 404.1988. found, 404.1995.

EXAMPLE 11

(E)-3-[3-(1-Adamantyl)-4-hydroxphenyl]-4-fluorocinnamic acid

Step 1: Ethyl (E)-3-bromo-4-fluorocinnamate

To a suspension of 5.36 g (26.4 mmol) of 3-bromo-4-fluorobenzaldehyde and 11.82 g (85.5 mmol) of K$_2$CO$_3$ in 100 ml of anhydrous THF under Ar, 13.0 ml (65.5 mmol) of triethyl phosphonoacetate was added. The reaction mixture was stirred at room temperature for 4 days at which time the reaction was complete. The mixture was extracted with EtOAc, washed with brine and water, dried (MgSO$_4$), filtered, and concentrated. Flash column chromatography (10% EtOAc/hexane) yielded a white solid (6.49 g, 90%): m.p. 64–65° C.; $R_f$ 0.60 (20% EtOAc/hexane). $^1$H NMR (400 MHz, CDCl$_3$) δ 1.34 (t, J=6.8 Hz, 3, CH$_3$), 4.26 (q, J=6.8 Hz, 2, CH$_2$), 6.36 (d, J=15.6 Hz, 1, HC=CCO), 7.13 (t, J=8.4 Hz, 1, ArH), 7.44 (m, 1, ArH), 7.57 (d, J=16.0 Hz, 1, C=CHCO), 7.72 ppm (dd, J=8.0, 2.0 Hz, 1, ArH).

Step 2: Ethyl (E)-3-[3-(1-adamantyl)-4-benzyloxyphenyl]-4-fluorocinnamate.

To a stirred suspension of 0.80 g (2.93 mmol) of ethyl (E)-3-bromo-4-fluorocinnamate, 1.07 g (2.95 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C$_6$H$_5$)$_3$]$_4$ and 0.30 g (7.1 mmol) of LiCl in 20 ml of DME was added under Ar 3.5 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a oil (1.38 g, 92%): $R_f$ 0.58 (20% EtOAc/hexane); $^1$H NMR (400 MHz, CDCl$_3$) δ 1.73, 2.18 (2 s, 12, AdCH$_2$), 2.05 (s, 3, AdCH), 1.37 (t, J=6.8 Hz, 3 CH$_3$), 4.25 (q, J=6.8 Hz, 2, CH$_2$), 5.16 (s, 2, CH$_2$), 6.39 (d, J=15.6 Hz, 1, HC=CCO), 7.01 (d, J=8.4 Hz, 1, ArH), 7.13 (t, J=8.0 Hz, 1, ArH), 7.29–7.58 (m, 9, ArH), 7.68 ppm (d, J=16.0 Hz, 1, C=CHCO).

Step 3: Ethyl (E)-3-[3-(1-adamantyl)-4-hydroxyphenyl]-4-fluorocinnamate.

A mixture of 1.35 g (2.64 mmol) of ethyl (E)-3-[3-(1-adamantyl)-4-benzyloxyphenyl]-4-fluorocinnamate was stirred in 20 ml of CH$_2$Cl$_2$ at –78° C. under Ar while 9.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a white solid (0.45 g, 41%): m.p. 180–182° C.; $R_f$ 0.35 (20% EtOAc/hexane); $^1$H NMR (400 MHz, CDCl$_3$) δ 1.80, 2.17 (2 s, 12, AdCH$_2$), 2.10 (s, 3, AdCH), 1.35 (t, J=8.0 Hz, 3 CH$_3$), 4.27 (q, J=7.6 Hz, 2, CH$_2$), 4.92 (s, 1, OH), 6.40 (d, J=16.0 Hz, 1, HC=CCO), 6.74 (d, J=8.0 Hz, 1, ArH), 7.14 (dd, J=8.8, 10.2 Hz, 1, ArH), 7.27 (d, J=1.6 Hz, 1, ArH), 7.38 (s, 1, ArH), 7.44 (m, 1, ArH), 7.56 (dd, J=8.0, 1.6 Hz, 1, ArH), 7.69 ppm (d, J=16.0 Hz, 1, C=CHCO).

Step 4: (E)-3-[3-(1-Adamantyl)-4-hydroxphenyl]-4-fluorocinnamic acid.

To a solution of 0.43 g (1.02 mmol) of ethyl (E)-3-[3-(1-adamantyl)-4-hydroxyphenyl]-4-fluorocinnamate in 20 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried ($MgSO_4$), filtered, and concentrated to afford a white solid (0.36 g, 90%): m.p. 222–223° C.; $R_f$0.28 (60% EtOAcihexane); $^1$H NMR (400 MHz, DMSO-$d_6$) δ 1.72, 2.10 (2 s, 12, $AdCH_2$), 2.03 (s, 3, AdCH), 6.55 (d, J=15.6 Hz, 1, HC=CCO), 6.85 (d, J=8.0 Hz, 1, ArH), 7.22 (s, 1, ArH), 7.24 (s, 1, ArH), 7.28 (dd, J=8.4, 10.2 Hz, 1, ArH), 7.63 (d, J=16.0 Hz, 1, C=CHCO), 7.68 (m, 1, ArH), 7.78 (dd, J=8.0, 2.4 Hz, 1, ArH), 9.57 (s, 1, OH), 12.39 ppm(s, 1, $CO_2$H); MS (FABHR): calcd. for $C_{25}H_{25}FO_3$, 392.1788. found, 392.1793.

EXAMPLE 12

(E)-5-[3-(1-Adamantyl)-4-hydroxphenyl]-2-chlorocinnamic acid

Step 1: 5-Bromo-2-chlorobenzaldehyde.

To a suspension of 5.23 g (23.6 mmol) of 5-bromo-2-chlorobenzyl alcohol in 50 ml of $CH_2Cl_2$ at 0° C., 8.36 g (38.7 mmol) of pyridinium chlorochromate was added. The reaction mixture was stirred at room temperature for 3 hours at which time the reaction was complete. The mixture was filtered, washed with EtOAc, dried ($MgSO_4$), filtered, and concentrated. Flash column chromatography (10% EtOAc/hexane) yielded a pale yellow solid (4.62 g, 89%): m.p. 56–58° C.; $R_f$0.73 (20% EtOAc/hexane). $^1$H NMR (400 MHz, $CDCl_3$) δ 7.34 (d, J=8.4 Hz, 1, ArH), 7.65 (dd, J=8.4, 2.4 Hz, 1, ArH), 8.04 (d, J=2.4 Hz, 1, ArH), 10.41 ppm (s, 1, CHO).

Step 2: Ethyl (E)-5-bromo-2-chlorocinnamate.

To a suspension of 4.60 g (20.9 mmol) of 5-bromo-2-chlorobenzaldehyde and 11.47 g (82.9 mmol) of $K_2CO_3$ in 100 ml of anhydrous THF under Ar, 14.0 ml (70.6 mmol) of triethyl phosphonoacetate was added. The reaction mixture was stirred at room temperature for 4 days at which time the reaction was complete. The mixture was extracted with EtOAc, washed with brine and water, dried ($MgSO_4$), filtered, and concentrated. Flash column chromatography (10% EtOAc/hexane) yielded a white solid (5.62 g, 93%): m.p. 42–44° C.; $R_f$0.68 (20% EtOAc/hexane). $^1$H NMR (400 MHz, $CDCl_3$) δ 1.34 (t, J=6.8 Hz, 3, $CH_3$), 4.28 (q, J=7.2 Hz, 2, $CH_2$), 6.42 (d, J=16.0 Hz, 1, HC=CCO), 7.28 (d, J=8.4 Hz, 1, ArH), 7.42 (dd, J=8.4, 2.4 Hz, 1, ArH), 7.74 (d, J=2.8 Hz, 1, ArH), 7.98 ppm (d, J=16.0 Hz, 1, C=CHCO).

Step 3: Ethyl (E)-5-[3-(1-adamantyl)-4-benzyloxyphenyl]-2-chlorocinnamate.

To a stirred suspension of 0.86 g (2.97 mmol) of ethyl (E)-5-bromo-2-chlorocinnamate, 1.08 g (2.98 mmol) of 3-(1-adamantyl)-4-benzyloxyphenylboronic acid [$^1$H NMR (300 MHz, $CDCl_3$) δ 1.77, 2.26 (2 s, 12, $AdCH_2$), 2.07 (s, 3, AdCH), 5.21 (s, 2, $CH_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P($C_6H_5$)$_3$]$_4$ and 0.30 g (7.1 mmol) of LiCl in 20 ml of DME was added under Ar 3.5 ml of 2.0 M aq. $Na_2CO_3$. The reaction mixture was heated at reflux (80–85° C.) overnight, at which time the reaction was complete. The mixture was extracted with EtOAc. The extract was washed with brine and water, dried ($MgSO_4$), filtered, and concentrated. Flash column chromatography (10% EtOAc/hexane) yielded a oil (1.44 g, 92%): $R_f$0.63 (20% EtOAc/hexane); $^1$H NMR (400 MHz, $CDCl_3$) δ 1.74, 2.20 (2 s, 12, $AdCH_2$), 2.07 (s, 3, AdCH), 1.36 (t, J=7.2 Hz, 3 $CH_3$), 4.30 (q, J=6.8 Hz, 2, $CH_2$), 5.17 (s, 2, $CH_2$), 6.50 (d, J=16.0 Hz, 1, HC=CCO), 7.01 (d, J=8.4 Hz, 1, ArH), 7.29–7.52 (m, 9, ArH), 7.76 (d, J=2.4 Hz, 1, ArH), 8.12 ppm (d, J=16.4 Hz, 1, C=CHCO).

Step 4: Ethyl (E)-5-[3-(1-adamantyl)-4-hydroxyphenyl]-2-chlorocinnamate.

A mixture of 1.40 g (2.66 mmol) of ethyl (E)-5-[3-(1-adamantyl)-4-benzyloxyphenyl]-2-chlorocinnamate was stirred in 20 ml of $CH_2Cl_2$ at −78° C. under Ar while 9.0 ml of 1.0 M $BBr_3$ in $CH_2Cl_2$ was added slowly over a period of 0.5 hour. The reaction mixture was stirred for 2 hours more, at which time the reaction was complete. The mixture was extracted with EtOAc, washed with brine and water, dried ($MgSO_4$), filtered, and concentrated. Flash column chromatography (20% EtOAc/hexane) yielded a white solid (0.77 g, 66%): m.p. 139–141° C.; $R_f$0.35 (20% EtOAc/hexane); $^1$H NMR (400 Hz, $CDCl_3$) δ 1.80, 2.17 (2 s, 12, $AdCH_2$), 2.12 (s, 3, AdCH), 1.36 (t, J=7.6 Hz, 3 $CH_3$), 4.30 (q, J=7.6 Hz, 2, $CH_2$), 4.91 (s, 1, OH), 6.50 (d, J=16.0 Hz, 1, HC=CCO), 6.73 (d, J=8.0 Hz, 1, ArH), 7.25 (dd, J=8.0, 2.8 Hz, 1, ArH), 7.39 (d, J=2.4 Hz, 1, ArH), 7.43 (d, J=8.0 Hz, 1, ArH), 7.47 (d, J=8.4, 1.6 Hz, 1, ArH), 7.74 (d, J=1.6 Hz, 1, ArH), 8.12 ppm (d, J=16.0 Hz, 1, C=CHCO).

Step 5: (E)-5-[3-(1-Adamantyl)-4-hydroxyphenyl]-2-chlorocinnamic acid.

To a solution of 0.75 g (1.72 mmol) of ethyl (E)-5-[3-(1-adamantyl)-4-hydroxyphenyl]-2-chlorocinnamate in 20 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried ($MgSO_4$), filtered, and concentrated to afford a white solid (0.54 g, 77%): m.p. 214–215° C.; $R_f$0.44 (60% EtOAc/hexane); $^1$H NMR (400 MHz, DMSO-$d_6$) δ 1.74, 2.14 (2 s, 12, $AdCH_2$), 2.05 (s, 3, AdCH), 6.79 (d, J=16.0 Hz, 1, HC=CCO), 6.86 (d, J=8.0 Hz, 1, ArH), 7.35 (d, J=2.4 Hz, 1, ArH), 7.41 (dd, J=8.0, 2.4 Hz, 1, ArH), 7.54 (d, J=8.0 Hz, 1, ArH), 7.62 (dd, J=8.8, 2.0 Hz, 1, ArH), 7.89 (d, J=16.0 Hz, 1, C=CHCO), 8.02 (d, J=2.4 Hz, 1, ArH), 9.55 (s, 1, OH), 12.67 ppm (s, 1, $CO_2$H); MS (FABHR): calcd. for $C_{25}H_{25}ClO_3$, 408.1492. found, 408.1497.

EXAMPLE 13

(E)-3-[3-(1-Adamantyl)-4-hydroxphenyl]-4-methoxycinnamic acid

Step 1: Ethyl (E)-3-bromo-4-methoxycinnamate.

To a suspension of 5.34 g (24.8 mmol) of 3-bromo-p-anisaldehyde and 11.97 g (86.6 mmol) of $K_2CO_3$ in 100 ml of anhydrous THF under Ar, 13.0 ml (65.5 mmol) of triethyl phosphonoacetate was added. The reaction mixture was stirred at room temperature for 4 days at which time the reaction was complete. The mixture was extracted with EtOAc, washed with brine and water, dried ($MgSO_4$), filtered, and concentrated. Flash colunm chromatography (20% EtOAc/hexane) yielded a white solid (5.85 g, 83%): m.p. 69–70° C.; $R_f$0.38 (20% EtOAc/hexane). $^1$H NMR (400

MHz, CDCl₃) δ 1.33 (t, J=7.6 Hz, 3, CH₃), 3.93 (s, 3, OCH₃), 4.25 (q, J=7.6 Hz, 2, CH₂), 6.31 (d, J=16.0 Hz, 1, HC=CCO), 6.90 (d, J=8.8 Hz, 1, ArH), 7.44 (dd, J=2.4, 8.8 Hz, 1, ArH), 7.75 (d, J=2.0 Hz, 1, ArH), 7.57 ppm (d, J=16.0 Hz, 1, C=CHCO).

Step 2: Ethyl (E)-3-[3-(1-adamantyl)-4-benzyloxyphenyl]-4-methoxycinnamate.

To a stirred suspension of 0.90 g (3.16 mmol) of ethyl (E)-3-bromo-4-methoxycinnamate, 1.17 g (3.23 mmol) of 3-(1-adamantyl)-4-benzyloxy-phenylboronic acid [$^1$H NMR (300 MHz, CDCl₃) δ 1.77, 2.26 (2 s, 12, AdCH₂), 2.07 (s, 3, AdCH), 5.21 (s, 2, CH₂), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C₆H₅)₃]₄ and 0.30 g (7.1 mmol) of LiCl in 20 ml of DME was added under Ar 3.5 ml of 2.0 M aq. Na₂CO₃. The reaction mixture was heated at reflux (80–85° C.) overnight, at which time the reaction was complete. The mixture was extracted with EtOAc. The extract was washed with brine and water, dried (MgSO₄), filtered, and concentrated. Flash column chromatography (10% EtOAc/hexane) yielded a white solid (1.20 g, 73%): m.p. 143–145° C.; R$_f$ 0.43 (20% EtOAc/hexane); $^1$H NMR (400 MHz, CDCl₃) δ 1.72, 2.17 (2 s, 12, AdCH₂), 2.04 (s, 3, AdCH), 1.32 (t, J=7.2 Hz, 3 CH₃), 3.85 (s, 3, OCH₃), 4.25 (q, J=7.6 Hz, 2, CH₂), 5.16 (s, 2, CH₂), 6.34 (d, J=15.6 Hz, 1, HC=CCO), 6.96 (d, J=8.4 Hz, 1, ArH), 6.98 (d, J=8.4 Hz, 1, ArH), 7.31–7.54 (m, 9, ArH), 7.67 ppm (d, J=16.0 Hz, 1, C=CHCO).

Step 3: Ethyl (E)-3-[3-(1-adamantyl)-4-hydroxphenyl]-4-methoxycinnamate.

A mixture of 1.20 g (2.29 mmol) of ethyl (E)-3-[3-(1-adamantyl)-4-benzyloxyphenyl]-4-methoxycinnamate was stirred in 20 ml of CH₂Cl₂ at –78° C. under Ar while 9.0 ml of 1.0 M BBr₃ in CH₂Cl₂ was added slowly over a period of 0.5 hour. The reaction mixture was stirred for 2 hours more, at which time the reaction was complete. The mixture was extracted with EtOAc, washed with brine and water, dried (MgSO₄), filtered, and concentrated. Flash column chromatography (20% EtOAc/hexane) yielded a white solid (0.48 g, 48%): m.p. 196–198° C.; R$_f$ 0.23 (20% EtOAc/hexane); $^1$H NMR (400 MHz, CDCl₃) δ 1.78, 2.15 (2 s, 12, AdCH₂), 2.08 (s, 3, AdCH), 1.33 (t, J=7.6 Hz, 3 CH₃), 3.85 (s, 3, OCH₃), 4.25 (q, J=7.6 Hz, 2, CH₂), 4.84 (s, 1, OH), 6.34 (d, J=15.6 Hz, 1, HC=CCO), 6.69 (d, J=8.0 Hz, 1, ArH), 6.95 (d, J=8.4 Hz, 1, ArH), 7.23 (dd, J=8.0, 1.6 Hz, 1, ArH), 7.34 (d, J=2.8 Hz, 1, ArH), 7.44 (dd, J=8.0, 2.0 Hz, 1, ArH), 7.47 (d, J=2.4 Hz, 1, ArH), 7.67 ppm (d, J=16.0 Hz, 1, C=CHCO).

Step 4: (E)-3-[3-(1-Adamantyl)-4-hydroxphenyl]-4-methoxycinnamic acid.

To a solution of 0.45 g (1.04 mmol) of ethyl (E)-3-[3-(1-adamantyl)-4-hydroxyphenyl]-4-methoxycinnamate in 20 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO₄), filtered, and concentrated to afford a off-white solid (0.37 g, 88%): m.p. 257–258° C.; R$_f$ 0.39 (EtOAc); $^1$H NMR (400 MHz, DMSO-d₆) δ 1.73, 2.11 (2 s, 12, AdCH₂), 2.04 (s, 3, AdCH), 3.79 (s, 3, OCH₃), 6.43 (d, J=15.6 Hz, 1, HC=CCO), 6.78 (d, J=8.4 Hz, 1, ArH), 7.09 (d, J=8.8 Hz, 1, ArH), 7.15 (dd, J=8.0, 2.4 Hz, 1, ArH), 7.18 (d, J=2.4 Hz, 1, ArH), 7.54 (d, J=2.0 Hz, 1, ArH), 7.59 (d, J=16.0 Hz, 1, C=CHCO), 7.62 (dd, J=8.0, 2.4 Hz, 1, ArH), 9.37 (s, 1, OH), 12.21 ppm(s, 1, CO₂H); MS (FABHR): calcd. for C₂₆H₂₈O₄, 404.1988. found, 404.1987.

EXAMPLE 14

(E)-5-[3-(1-Adamantyl)-4-hydroxphenyl]-3-chloro-6-methoxycinnamic acid

Step 1: 5-Bromo-3-chloro-6-methoxybenzaldehyde.

To a suspension of 3.13 g (13.3 mmol) of 3-bromo-5-chlorosalicylaldehyde in 50 ml of acetone at room temperature, 3.0 ml (48.2 mmol) of methyl iodide was added. The reaction mixture was stirred at room temperature for 4 hours at which time the reaction was complete. The mixture was filtered, washed with EtOAc, dried (MgSO₄), filtered, and concentrated. Flash column chromatography (10% EtOAc/hexane) yielded a pale white solid (1.45 g, 44%): m.p. 69–71° C.; R$_f$ 0.48 (20% EtOAc/hexane). $^1$H NMR (400 MHz, CDCl₃) δ 3.98 (s, 3, OCH₃), 7.76 (d, J=2.4 Hz, 1, ArH), 7.78 (d, J=2.4 Hz, 1, ArH), 10.30 ppm (s, 1, CHO).

Step 2: Ethyl (E)-5-bromo-3-chloro-6-methoxycinnamate.

To a suspension of 1.40 g (5.61 mmol) of 5-bromo-3-chloro-6-methoxybenzaldehyde and 6.03 g (43.6 mmol) of K₂CO₃ in 100 ml of anhydrous THF under Ar, 5.0 ml (25.2 mmol) of triethyl phosphonoacetate was added. The reaction mixture was stirred at room temperature for 4 days at which time the reaction was complete. The mixture was extracted with EtOAc, washed with brine and water, dried (MgSO₄), filtered, and concentrated. Flash column chromatography (10% EtOAc/hexane) yielded a white solid (1.65 g, 92%): m.p. 54–55° C.; R$_f$ 0.42 (10% EtOAc/hexane). $^1$H NMR (400 MHz, CDCl₃) δ 1.35 (t, J=7.6 Hz, 3, CH₃), 3.83 (s, 3, OCH₃), 4.28 (q, J=7.6 Hz, 2, CH₂), 6.4 (d, J=16.0 Hz, 1, HC=CCO), 7.48 (d, J=2.4 Hz, 1, ArH), 7.57 (d, J=2.4 Hz, 1, ArH), 7.83 ppm (d, J=16.0 Hz, 1, C=CHCO).

Step 3: Ethyl (E)-5-[3-(1-adamantyl)-4-benzyloxyphenyl]-3-chloro-6-methoxycinnamate.

To a stirred suspension of 0.90 g (2.82 mmol) of ethyl (E)-5-bromo-3-chloro-6-methoxycinnamate, 1.03 g (2.84 mmol) of 3-(1-adamantyl)-4-benzyloxyphenylboronic acid [$^1$H NMR (300 MHz, CDCl₃) δ 1.77, 2.26 (2 s, 12, AdCH₂), 2.07 (s, 3, AdCH), 5.21 (s, 2, CH₂), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C₆H₅)₃]₄ and 0.30 g (7.1 mmol) of LiCl in 20 ml of DME was added under Ar 3.5 ml of 2.0 M aq. Na₂CO₃. The reaction mixture was heated at reflux (80–85° C.) overnight, at which time the reaction was complete. The mixture was extracted with EtOAc. The extract was washed with brine and water, dried (MgSO₄), filtered, and concentrated. Flash column chromatography (10% EtOAc/hexane) yielded a white solid (1.37 g, 87%): m.p. 115–117° C.; R$_f$ 0.63 (20% EtOAc/hexane); $^1$H NMR (400 MHz, CDCl₃) δ 1.72, 2.16 (2 s, 12, AdCH₂), 2.04 (s, 3, AdCH), 1.34 (t, J=7.2 Hz, 3 CH₃), 3.39 (s, 3, OCH₃), 4.26 (q, J=7.2 Hz, 2, CH₂), 5.15 (s, 2, CH₂), 6.48 (d, J=15.6 Hz, 1, HC=CCO), 6.99 (d, J=8.8 Hz, 1, ArH), 7.32–7.54 (m, 9, ArH), 7.96 ppm (d, J=15.6 Hz, 1, C=CHCO).

Step 4: Ethyl (E)-5-[3-(1-adamantyl)-4-hydroxphenyl]-3-chloro-6-methoxycinnamate.

A mixture of 1.35 g (2.42 mmol) of ethyl (E)-5-[3-(1-adamantyl)-4-benzyloxyphenyl]-3-chloro-6-methoxycinnamate was stirred in 20 ml of CH₂Cl₂ at –78° C. under Ar while 9.0 ml of 1.0 M BBr₃ in CH₂Cl₂ was added slowly over a period of 0.5 hour. The reaction mixture was stirred for 2 hours more, at which time the reaction was complete. The mixture was extracted with EtOAc, washed with brine and water, dried (MgSO₄), filtered, and concentrated. Flash column chromatography (20% EtOAc/hexane) yielded a white solid (0.85 g, 75%): m.p. 227–229° C.; $R_f$ 0.50 (20% EtOAc/hexane); $^1$H NMR (400 Hz, CDCl$_3$) δ 1.78, 2.13 (2 s, 12, AdCH$_2$), 2.08 (s, 3, AdCH), 1.33 (t, J=7.6 Hz, 3 CH$_3$), 3.38 (s, 3, OCH$_3$), 4.26 (q, J=7.6 Hz, 2, CH$_2$), 4.91 (s, 1, OH), 6.48 (d, J=15.6 Hz, 1, HC=CCO), 6.70 (d, J=8.0 Hz, 1, ArH), 7.24 (dd, J=8.0, 2.8 Hz, 1, ArH), 7.30 (d, J=2.4 Hz, 1, ArH), 7.41 (d, J=2.4 Hz, 1, ArH), 7.45 (d, J=2.4 Hz, 1, ArH), 7.96 ppm (d, J=16.0 Hz, 1, C=CHCO).

Step 5: (E)-5-[3-(1-Adamantyl)-4-hydroxphenyl]-3-chloro-6-methoxycinnamic acid.

To a solution of 0.83 g (1.78 mmol) of ethyl (E)-5-[3-(1-adamantyl)-4-hydroxyphenyl]-3-chloro-6-methoxycinnamate in 20 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a white solid (0.41 g, 53%): m.p. 245–246° C.; $R_f$ 0.39 (60% EtOAc/hexane); $^1$H NMR (400 MHz, DMSO-d$_6$) δ 1.72, 2.14 (2 s, 12, AdCH$_2$), 2.02 (s, 3, AdCH), 3.84 (s, 3, OCH$_3$), 6.65 (d, J=15.6 Hz, 1, HC=CCO), 6.83 (d, J=8.8 Hz, 1, ArH), 7.21 (dd, J=8.0, 2.4 Hz, 1, ArH), 7.30 (d, J=2.8 Hz, 1, ArH), 7.38 (d, J=2.8 Hz, 1, ArH), 7.75 (d, J=16.0 Hz, 1, C=CHCO), 7.79 (d, J=2.4 Hz, 1, ArH), 9.56 (s, 1, OH), 12.54 ppm(s, 1, CO$_2$H); MS (FABHR): calcd. for C$_{26}$H$_{27}$ClO$_4$, 438.1598. found, 438.1593.

EXAMPLE 15

(E)-5-[3-(1-Adamantyl)-4-hydroxphenyl]-3-chloro-6-ethoxycinnamic acid

Step 1: 5-Bromo-3-chloro-6-ethoxybenzaldehyde.

To a suspension of 3.02 g (12.8 mmol) of 3-bromo-5-chloro-salicylaldehyde in 50 ml of acetone at room temperature, 3.0 ml (37.5 mmol) of ethyl iodide was added. The reaction mixture was stirred at room temperature for 4 hours at which time the reaction was complete. The mixture was filtered, washed with EtOAc, dried (MgSO$_4$), filtered, and concentrated. Flash column chromatography (10% EtOAc/hexane) yielded a white solid (0.77 g, 23%): m.p. 60–62° C.; $R_f$ 0.58 (20% EtOAc/hexane). $^1$H NMR (400 MHz, CDCl$_3$) δ 1.50 (t, J=7.6 Hz, 3, CH$_3$), 4.14 (q, J=7.6 Hz, 2, CH$_2$), 7.76 (d, J=2.4 Hz, 1, ArH), 7.78 (d, J=2.4 Hz, 1, ArH), 10.29 ppm (s, 1, CHO).

Step 2 Ethyl (E)-5-bromo-3-chloro-6-ethoxycinnamate.

To a suspension of 0.75 g (2.85 mmol) of 5-bromo-3-chloro-6-ethoxybenzaldehyde and 3.63 g (26.3 mmol) of K$_2$CO$_3$ in 100 ml of anhydrous THF under Ar, 3.0 ml (15.1 mmol) of triethyl phosphonoacetate was added. The reaction mixture was stirred at room temperature for 4 days at which time the reaction was complete. The mixture was extracted with EtOAc, washed with brine and water, dried (MgSO$_4$), filtered, and concentrated. Flash column chromatography (10% EtOAc/hexane) yielded a white solid (0.88 g, 92%): m.p. 43–44° C.; $R_f$ 0.45 (10% EtOAc/hexane). $^1$H NMR (400 MHz, CDCl$_3$) δ 1.34 (t, J= 7.6 Hz, 3, CH$_3$), 1.46 (t, J=7.6 Hz, 3, CH$_3$), 3.98 (q, J=7.6 Hz, 2, CH$_2$), 4.27 (q, J=7.6 Hz, 2, CH$_2$), 6.45 (d, J=16.0 Hz, 1, HC=CCO), 7.48 (d, J=2.4 Hz, 1, ArH), 7.57 (d, J=2.4 Hz, 1, ArH), 7.85 ppm (d, J=16.0 Hz, 1, C=CHCO).

Step 3 Ethyl (E)-5-[3-(1-adamantyl)-4-benzyloxyphenyl]-3-chloro-6-ethoxycinnamate.

To a stirred suspension of 0.88 g (2.64 mmol) of ethyl (E)-5-bromo-3-chloro-6-ethoxycinnamate, 0.96 g (2.65 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.35 g (0.30 mmol) of Pd[P(C$_6$H$_5$)$_3$]$_4$ and 0.30 g (7.1 mmol) of LiCl in 20 ml of DME was added under Ar 3.5 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a oil (1.45 g, 96%): $R_f$ 0.67 (20% EtOAc/hexane); $^1$H NMR (400 MHz, CDCl$_3$) δ 1.72, 2.16 (2 s, 12, AdCH$_2$), 2.04 (s, 3, AdCH), 1.13 (t, J=7.6 Hz, 3, CH$_3$), 1.46 (t, J=7.6 Hz, 3, CH$_3$), 3.49 (q, J=7.6 Hz, 2, CH$_2$), 4.26 (q, J=7.6 Hz, 2, CH$_2$), 5.15 (s, 2, CH$_2$), 6.47 (d, J=15.6 Hz, 1, HC=CCO), 6.99 (d, J=8.8 Hz, 1, ArH), 7.30–7.56 (m, 9, ArH), 7.99 ppm (d, J=15.6 Hz, 1, C=CHCO).

Step 4: Ethyl (E)-5-[3-(1-adamantyl)-4-hydroxphenyl]-3-chloro-6-ethoxycinnamate.

A mixture of 1.40 g (2.45 mmol) of ethyl (E)-5-[3-(1-adamantyl)-4-benzyloxyphenyl]-3-chloro-6-ethoxycinnamate was stirred in 20 ml of CH$_2$Cl$_2$ at −78° C. under Ar while 9.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a white solid (0.48 g, 41%): m.p. 192–194° C.; $R_f$ 0.48 (20% EtOAc/hexane); $^1$H NMR (400 Hz, CDCl$_3$) δ 1.78, 2.13 (2 s, 12, AdCH$_2$), 2.08 (s, 3, AdCH), 1.13 (t, J=7.6 Hz, 3, CH$_3$), 1.46 (t, J=7.6 Hz, 3, CH$_3$), 3.46 (q, J=7.6 Hz, 2, CH$_2$), 4.27 (q, J=7.6 Hz, 2, CH$_2$), 4.90 (s, 1, OH), 6.45 (d, J=15.6 Hz, 1, HC=CCO), 6.70 (d, J=8.0 Hz, 1, ArH), 7.24 (dd, J=8.0, 2.8 Hz, 1, ArH), 7.30 (d, J=2.4 Hz, 1, ArH), 7.41 (d, J=2.4 Hz, 1, ArH), 7.45 (d, J=2.4 Hz, 1, ArH), 7.96 ppm (d, J=16.0 Hz, 1, C=CHCO).

Step 5: (E)-5-[3-(1-Adamantyl)-4-hydroxphenyl]-3-chloro-6-ethoxycinnamic acid.

To a solution of 0.46 g (0.96 mmol) of ethyl (E)-5-[3-(1-adamantyl)-4-hydroxyphenyl]-3-chloro-6-ethoxycinnamate in 20 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a white solid (0.37 g, 86%): m.p. 201–202° C.; $R_f$ 0.41 (60% EtOAc/hexane); $^1$H NMR (400 MHz, DMSO-d$_6$) δ 1.72, 2.09 (2 s, 12, AdCH$_2$), 2.03 (s, 3, AdCH), 1.06 (t, J=7.6 Hz, 3, CH$_3$), 3.41 (q, J=7.6 Hz, 2, CH$_2$), 6.65 (d, J=15.6 Hz, 1, HC=CCO), 6.83 (d, J=8.4 Hz, 1, ArH), 7.20 (dd, J=8.0, 2.4 Hz, 1, ArH), 7.35 (d, J=2.4 Hz, 1, ArH), 7.37 (d, J=2.4 Hz, 1, ArH), 7.78 (d, J=16.0 Hz, 1, C=CHCO), 7.79 (d, J=2.4 Hz, 1, ArH), 9.56 (s, 1, OH), 12.54 ppm(s, 1, CO$_2$H); MS (FABHR): calcd. for C$_{27}$H$_{29}$ClO$_4$, 452.1754. found, 452.1751.

EXAMPLE 16

(E)-4-[3-(1-Adamantyl)-4-hydroxphenyl]-3,5-dichlorocinnamic acid

Step 1: Methyl 3,5-dichloro-4-hydroxybenzate.

To a suspension of 5.00 g (24.2 mmol) of 3,5-dichloro-4-hydroxybenzoic acid in 50 ml of MeOH was stirred in a 0° C. ice bath under Ar, 5.0 ml (68.5 mmol) of thionyl chloride was added over a period of 20 min. The reaction mixture was stirred for 1.5 hours more, then warmed to room temperature overnight. The mixture was extracted with EtOAc, washed with brine, and water, dried ($MgSO_4$), filtered, and concentrated to afford a white solid (5.26 g, 98% yield): m.p. 117–119° C.; $R_f$ 0.69 (40% EtOAc/hexane); $^1H$ NMR (400 MHz, $CDCl_3$) δ 3.91 (s, 3, $CH_3$), 6.28 (s, 1, OH), 7.97 ppm (s, 2, ArH).

Step 2: Methyl 3,5-dichloro-4-methoxybenzate.

To a suspension of 5.20 g (23.5 mmol) of methyl 3,5-dichloro-4-hydroxybenzoic ester in 40 ml of acetone at room temperature, 5.0 ml (80.3 mmol) of methyl iodide was added. The reaction mixture was stirred at room temperature for 4 hours at which time the reaction was complete. The mixture was filtered, washed with EtOAc, dried ($MgSO_4$), filtered, and concentrated. Flash column chromatography (10% EtOAc/hexane) yielded a pale-yellow solid (5.46 g, 98%): m.p. 68–70° C.; $R_f$ 0.77 (20% EtOAc/hexane); $^1H$ NMR (400 MHz, $CDCl_3$) δ 3.92 (s, 3, $CH_3$), 3.96 (s, 3, $OCH_3$), 7.98 ppm (s, 2, ArH).

Step 3: 3,5-Dichloro-4-methoxybenzyl alcohol.

To a suspension of 5.40 g (22.9 mmol) of methyl 3,5-dichloro-4-methoxybenzoic ester in 50 ml of THF was stirred in a 0° C. ice bath, 1.30 g (34.2 mmol) of lithium aluminum hydride was added. The reaction mixture was stirred for 4 hours at which time the reaction was complete, then quenched with minimum amount of water and dried ($MgSO_4$). The mixture was filtered, extracted with EtOAc, dried ($MgSO_4$), filtered, and concentrated. Flash column chromatography (10% EtOAc/hexane) yielded a oil (3.61 g, 76%): $R_f$ 0.24 (20% EtOAc/hexane); $^1H$ NMR (400 MHz, $CDCl_3$) δ 3.87 (s, 3, $OCH_3$), 4.60 (s, 2, $CH_2$), 7.28 ppm (s, 2, ArH).

Step 4: 3,5-Dichloro-4-methoxybenzaldehyde.

To a suspension of 3.60 g (17.3 mmol) of 3,5-Dichloro-4-methoxybenzyl alcohol in 40 ml of $CH_2Cl_2$ at 0° C., 5.00 g (23.1 mmol) of pyridinium chlorochromate was added. The reaction mixture was stirred at room temperature for 3 hours at which time the reaction was complete. The mixture was filtered, washed with EtOAc, dried ($MgSO_4$), filtered, and concentrated. Flash column chromatography (20% EtOAc/hexane) yielded a pale yellow solid (1.39 g, 39%): m.p. 44–46° C.; $R_f$ 0.63 (20% EtOAc/hexane). $^1H$ NMR (400 MHz, $CDCl_3$) δ 3.99 (s, 3, $OCH_3$), 7.83 (s, 2, ArH), 9.87 ppm (s, 1, CHO).

Step 5: Ethyl (E)-3,5-dichloro-4-methoxycinnamate.

To a suspension of 1.39 g (6.78 mmol) of 3,5-dichloro-4-methoxybenzaldehyde and 4.56 g (32.9 mmol) of $K_2CO_3$ in 50 ml of anhydrous THF under Ar, 5.0 ml (25.2 mmol) of triethyl phosphonoacetate was added. The reaction mixture was stirred at room temperature for 4 days at which time the reaction was complete. The mixture was extracted with EtOAc, washed with brine and water, dried ($MgSO_4$), filtered, and concentrated. Flash column chromatography (10% EtOAc/hexane) yielded a white solid (1.70 g, 91%): m.p. 85–87° C.; $R_f$ 0.73 (20% EtOAc/hexane); $^1H$ NMR (400 MHz, $CDCl_3$) δ 1.34 (t, J=7.2 Hz, 3, $CH_3$), 3.93 (s, 3, $OCH_3$), 4.26 (q, J=7.2 Hz, 2, $CH_2$), 6.3 d, J=16.0 Hz, 1, HC=CCO), 7.46 (s, 2, ArH), 7.50 ppm (d, J=16.0 Hz, 1, C=CHCO).

Step 6: Ethyl (E)-3,5-dichloro-4-hydroxycinnamate.

A mixture of 1.70 g (6.18 mmol) of ethyl (E)-3,5-dichloro-4-methoxycinnamate was stirred in 10 ml of $CH_2Cl_2$ at 0° C. under Ar while 9.0 ml of 1.0 M $BBr_3$ in $CH_2Cl_2$ was added slowly over a period of 0.5 hour. The reaction mixture was stirred for 4 hours more, at which time the reaction was complete. The mixture was extracted with EtOAc, washed with brine and water, dried ($MgSO_4$), filtered, and concentrated. Flash column chromatography (20% EtOAc/hexane) yielded a pale-yellow solid (1.29 g, 80%): m.p. 64–66° C.; $R_f$ 0.40 (20% EtOAc/hexane); 1H NMR (400 MHz, $CDCl_3$) δ 1.33 (t, J=7.6 Hz, 3, $CH_3$), 4.26 (q, J=7.6 Hz, 2, $CH_2$), 6.32 (d, J=16.0 Hz, 1, HC=CCO), 7.45 (s, 2, ArH), 7.49 ppm (d, J=16.0 Hz, 1, C=CHCO).

Step 7: Ethyl (E)-3,5-dichloro-4-(trifluoromethanesulfonyloxy)cinnamate.

To a solution of 1.25 g (4.78 mmol) of ethyl (E)-3,5-dichloro-4-hydroxycinnamate and 2.0 ml (24.8 mmol) of pyridine in 50 ml of $CH_2Cl_2$ in a 0° C. ice bath under Ar, 2.0 ml (11.8 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% $NaHCO_3$, brine, and water, dried ($MgSO_4$), filtered, and concentrated to afford a white solid (1.78 g, 95% yield): m.p. 88–89° C.; $R_f$ 0.54 (20% EtOAc/hexane); $^1H$ NMR (400 MHz, $CDCl_3$) δ 1.33 (t, J=8.0 Hz, 3, $CH_3$), 4.27 (q, J=7.6 Hz, 2, $CH_2$), 6.44 (d, J=16.0 Hz, 1, HC=CCO), 7.51 (d, J=16.0 Hz, 1, C=CHCO), 7.55 ppm (s, 2, ArH).

Step 8: Ethyl (E)-4-[3-(1-adamantyl)-4-benzyloxyphenyl]-3,5-dichlorocinnamate.

To a stirred suspension of 1.00 g (2.54 mmol) of ethyl (E)-3,5-dichloro-4-(trifluoromethanesulfonyloxy)cinnamate, 0.95 g (2.62 mmol) of 3-(1-adamantyl)-4-benzyloxyphenylboronic acid [$^1H$ NMR (300 MHz, $CDCl_3$) δ 1.77, 2.26 (2 s, 12, $AdCH_2$), 2.07 (s, 3, AdCH), 5.21 (s, 2, $CH_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of $Pd[P(C_6H_5)_3]_4$ and 0.26 g (6.1 mmol) of LiCl in 20 ml of DME was added under Ar 1.4 ml of 2.0 M aq. $Na_2CO_3$. The reaction mixture was heated at reflux (80–85° C.) overnight, at which time the reaction was complete. The mixture was extracted with EtOAc. The extract was washed with brine and water, dried ($MgSO_4$), filtered, and concentrated. Flash column chromatography (10% EtOAc/hexane) yielded a white solid (0.43 g, 30%): m.p. 154–156° C.; $R_f$ 0.61 (20% EtOAc/hexane); $^1H$ NMR (400 MHz, $CDCl_3$) δ 1.73, 2.14 (2 s, 12, $AdCH_2$), 2.02 (s, 3, AdCH), 1.34 (t, J=7.6 Hz, 3 $CH_3$), 4.276 (q, J=7.6 Hz, 2, $CH_2$), 5.11 (s, 2, $CH_2$), 6.45 (d, J=15.9 Hz, 1, HC=CCO), 6.97 (d, J=8.0 Hz, 1, ArH), 7.3–7.5 (m, 9, ArH), 7.56 ppm (d, J=15.4 Hz, 1, C=CHCO).

Step 9: Ethyl (E)-4-[3-(1-adamantyl)-4-hydroxphenyl]-3,5-dichlorocinnamate.

A mixture of 0.40 g (0.71 mmol) of ethyl (E)-4-[3-(1-adamantyl)-4-benzyloxyphenyl]-3,5-dichlorocinnamate was stirred in 10 ml of $CH_2Cl_2$ at −78° C. under Ar while 3.0 ml of 1.0 M $BBr_3$ in $CH_2Cl_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a pale-yellow solid (0.23 g, 68%): m.p. 215–217° C.; R$_f$0.42 (20% EtOAc/hexane); $^1$H NMR (400 MHz, CDCl$_3$) δ 1.78, 2.14 (2 s, 12, AdCH$_2$), 2.09 (s, 3, AdCH), 1.33 (t, J=7.6 Hz, 3, CH$_3$), 4.26 (q, J=7.6 Hz, 2, CH$_2$), 4.91 (s, 1, OH), 6.47 (d, J=15.6 Hz, 1, HC=CCO), 6.70 (d, J=8.0 Hz, 1, ArH), 7.21 (dd, J=8.0, 2.4 Hz, 1, ArH), 7.31 (d, J=2.4 Hz, 1, ArH), 7.46 (s, 2, ArH), 7.99 ppm (d, J=15.6 Hz, 1, C=CHCO).

Step 10: (E)-4-[3-(1-Adamantyl)-4-hydroxphenyl]-3,5-dichlorocinnamic acid.

To a solution of 0.21 g (0.45 mmol) of ethyl (E)-4-[3-(1-adamantyl)-4-hydroxyphenyl]-3,5-dichlorocinnamate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a brown solid (0.08 g, 40%): m.p. 224–225° C.; R$_f$0.29 (60% EtOAc/hexane); $^1$H NMR (400 MHz, DMSO-d$_6$) δ 1.71, 2.06 (2 s, 12, AdCH$_2$), 2.01 (s, 3, AdCH), 6.71 (d, J=16.4 Hz, 1, HC=CCO), 6.83 (d, J=8.4 Hz, 1, ArH), 6.90 (s, 1, ArH), 6.91 (d, J=2.4 Hz, 1, ArH), 7.55 (d, J=16.4 Hz, 1, C=CHCO), 7.92 (s, 2, ArH), 9.57 (s, 1, OH), 12.58 ppm(s, 1, CO$_2$H); MS (EIHR): calcd. for C$_{25}$H$_{24}$Cl$_2$O$_3$, 442.1102. found, 442.1096.

EXAMPLE 17

7-[3-(1-Adamantyl)-4-hydroxphenyl]coumarin-3-carboxylic acid

Step 1: Ethyl 7-hydroxycoumarin-3-carboxylate.

To a solution of 1.00 g (3.62 mmol) of ethyl 7-acetoxycoumarin-3-carboxylate in 30 ml of EtOH was added 3.00 g (21.7 mmol) of K$_2$CO$_3$. This mixture was stirred at room temperature for 4 hours, at which time the reaction was complete. The mixture was extracted with EtOAc, and the extract was washed with 10% HCl, brine, and water, dried (MgSO$_4$), filtered and concentrated to afford a pale-yellow solid (0.80 g, 94% yield): m.p. 162–164° C.; R$_f$0.43 (60% EtOAc/hexane); $^1$H NMR (400 MHz, CDCl$_3$) δ 1.40 (t, J=6.8 Hz, 3, CH$_3$), 4.49 (q, J=6.8 Hz, 2, CH$_2$), 6.28 (s, 1, OH), 6.85 (dd, J=8.0, 2.4 Hz, 1, ArH), 6.86 (s, 1, ArH), 7.49 (d, J=8.0 Hz, 1, ArH), 8.51 ppm (s, 1, ArH).

Step 2: Ethyl 7-(trifluoromethanesulfonyloxy)coumarin-3-carboxylate.

To a solution of 0.80 g (3.42 mmol) of ethyl 7-hydroxycoumarin-3-carboxylate and 1.5 ml (18.5 mmol) of pyridine in 30 ml of CH$_2$Cl$_2$ in a 0° C. ice bath under Ar, 1.5 ml (8.9 mmol) of trifluoromethanesulfonic anhydride was added slowly over a period of 0.5 hour. The reaction mixture was stirred for 4 hours, at which time reaction was complete. The mixture was warmed to room temperature and extracted with EtOAc. The extract was washed with 10% HCl, 5% NaHCO$_3$, brine, and water, dried (MgSO$_4$), filtered, and concentrated to afford a pale-yellow solid (1.20 g, 97% yield): m.p. 155–157° C.; R$_f$0.66 (60% EtOAc/hexane); $^1$H NMR (400 MHz, CDCl$_3$) δ 1.41 (t, J=6.8 Hz, 3, CH$_3$), 4.42 (q, J=6.8 Hz, 2, CH$_2$), 7.25 (s, 1, ArH), 7.28 (dd, J=8.0, 2.4 Hz, 1, ArH), 7.70 (d, J=8.0 Hz, 1, ArH), 8.50 ppm (s, 1, ArH).

Step 3: Ethyl 7-[3-(1-adamantyl)-4-benzyloxyphenyl]coumarin-3-carboxylate.

To a stirred suspension of 0.84 g (2.31 mmol) of 7-(trifluoromethane-sulfonyloxy)coumarin-3-carboxylate, 0.85 g (2.35 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of Pd[P(C$_6$H$_5$)$_3$]$_4$ and 0.26 g (6.1 mmol) of LiCl in 20 ml of DME was added under Ar 2.8 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (20% EtOAc/hexane) yielded a yellow solid (0.62 g, 50%): m.p. 161–163° C.; R$_f$0.64 (20% EtOAc/hexane); $^1$H NMR (400 MHz, CDCl$_3$) δ 1.75, 2.19 (2 s, 12, AdCH$_2$), 2.07 (s, 3, AdCH), 1.41 (t, J=7.6 Hz, 3 CH$_3$), 4.41 (q, J=7.6 Hz, 2, CH$_2$), 5.18 (s, 2, CH$_2$), 7.01 (d, J=7.6 Hz, 1, ArH), 7.3–7.5 (m, 9, ArH), 7.61 (d, J=7.6 Hz, 1, ArH), 8.55 ppm (s, 1, ArH).

Step 4: Ethyl 7-[3-(1-adamantyl)-4-hydroxyphenyltcoumarin-3-carboxylate.

A mixture of 0.60 g (1.12 mmol) of ethyl 7-[3-(1-adamantyl)-4-benzyloxyphenyl]coumarin-3-carboxylate was stirred in 30 ml of CH$_2$Cl$_2$ at –78° C. under Ar, and 3.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a yellow solid (0.22 g, 40%): m.p. 278–280° C.; R$_f$0.50 (40% EtOAc/hexane); $^1$H NMR (400 MHz, CDCl$_3$) δ 1.80, 2.17 (2 s, 12, AdCH$_2$), 2.12 (s, 3, AdCH), 1.43 (t, J=7.6 Hz, 3 CH$_3$), 4.43 (q, J=7.6 Hz, 2, CH$_2$), 5.02 (s, 1, OH), 6.77 (d, J=8.4 Hz, 1, ArH), 7.37 (dd, J=8.0, 2.4 Hz, 1, ArH), 7.52 (d, J=2.4 Hz, 1, ArH), 7.53 (s, 1, ArH), 7.55 (d, J=2.4 Hz, 1, ArH), 7.61 (d, J=8.4 Hz, 1, ArH), 8.56 ppm (s, 1, ArH).

Step 5: 7-[3-(1-Adamantyl)-4-hydroxyphenyl]coumarin-3-carboxylic acid.

To a solution of 0.20 g (0.45 mmol) of ethyl 7-[3-(1-adamantyl)-4-hydroxyphenyl]coumarin-3-carboxylate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a yellow solid (0.78 g, 97%): m.p. >320° C.; R$_f$0.10 (EtOAc); $^1$H NMR (400 MHz, DMSO-d$_6$) δ 1.74, 2.14 (2 s, 12, AdCH$_2$), 2.05 (s, 3, AdCH), 6.87 (d, J=8.0 Hz, 1, ArH), 7.41 (s, 1, ArH), 7.42 (dd, J=8.0, 2.4 Hz, 1, ArH), 7.49 (s, 1, ArH), 7.51 (d, J=8.4 Hz, 1, ArH), 7.68 (d, J=8.0 Hz, 1, ArH), 7.94 (s, 1, ArH), 9.68 (s, 1, OH), 12.61 ppm (s, 1, CO$_2$H); MS (FABHR): calcd. for C$_{26}$H$_{24}$O$_5$, 417.1702. found, 417.1703.

EXAMPLE 18

(E)-4-[3-(1-Adamantyl)-4-hydroxphenyl]-3-bromo-cinnamic acid

Step 1: Ethyl (E)-3-bromo-4-methoxycinnamate.

To a suspension of 5.34 g (24.8 mmol) of 3-bromo-p-anisaldehyde and 11.97 g (86.6 mmol) of K$_2$CO$_3$ in 100 ml of anhydrous THF under Ar, 13.0 ml (65.5 mmol) of triethyl phosphonoacetate was added. The reaction mixture was stirred at room temperature for 4 days at which time the reaction was complete. The mixture was extracted with EtOAc, washed with brine and water, dried (MgSO$_4$), filtered, and concentrated. Flash column chromatography (20% EtOAc/hexane) yielded a white solid (5.85 g, 83%): m.p. 69–70° C.; R$_f$0.38 (20% EtOAc/hexane). $^1$H NMR (400 MHz, CDCl$_3$) δ 1.33 (t, J=7.6 Hz, 3, CH$_3$), 3.93 (s, 3, OCH$_3$), 4.25 (q, J=7.6 Hz, 2, CH$_2$), 6.31 (d, J=16.0 Hz, 1, HC=CCO), 6.90 (d, J=8.8 Hz, 1, ArH), 7.44 (dd, J=2.4, 8.8 Hz, 1, ArH), 7.75 (d, J=2.0 Hz, 1, ArH), 7.57 ppm (d, J=16.0 Hz, 1, C=CHCO).

Step 2: Ethyl (E)-3-bromo-4-hydroxycinnamate.

A mixture of 2.61 g (9.15 mmol) of ethyl (E)-3-bromo-4-methoxycinnamate was stirred in 10 ml of CH$_2$Cl$_2$ at 0° C. under Ar while 15.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a pale-yellow solid (1.58 g, 63%): m.p. 101–103° C.; R$_f$0.25 (20% EtOAc/hexane); $^1$H NMR (400 MHz, CDCl$_3$) δ 1.33 (t, J=7.6 Hz, 3, CH$_3$), 4.25 (q, J=7.6 Hz, 2, CH$_2$), 5.72 (s, 1, OH), 6.31 (d, J=16.4 Hz, 1, HC=CCO), 7.02 (d, J=8.8 Hz, 1, ArH), 7.40 (dd, J=2.4, 8.8 Hz, 1, ArH), 7.55 (d, J=16.0 Hz, 1, C=CHCO), 7.65 ppm (d, J=2.0 Hz, 1, ArH).

Step 3: Ethyl (E)-3-bromo-4-(trifluoromethanesulfonyloxy) cinnamate.

To a solution of 1.55 g (5.71 mmol) of ethyl (E)-3-bromo-4-hydroxycinnamate and 1.0 ml (12.4 mmol) of pyridine in 50 ml of CH$_2$Cl$_2$ in a 0° C. ice bath under Ar, 1.60 ml (9.72 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% NaHCO$_3$, brine, and water, dried (MgSO$_4$), filtered, and concentrated to afford a white solid (2.19 g, 95% yield): m.p. 77–79° C.; R$_f$0.49 (20% EtOAc/hexane); $^1$H NMR (400 MHz, CDCl$_3$) δ 1.34 (t, J=7.6 Hz, 3, CH$_3$), 4.28 (q, J=7.6 Hz, 2, CH$_2$), 6.44 (d, J=16.4 Hz, 1, HC=CCO), 7.37 (d, J=8.4 Hz, 1, ArH), 7.52 (dd, J=2.4, 8.4 Hz, 1, ArH), 7.57 (d, J=16.4 Hz, 1, C=CHCO), 7.83 ppm (d, J=2.4 Hz, 1, ArH).

Step 4: Ethyl (E)-4-[3-(1-adamantyl)-4-benzyloxyphenyl]-3-bromocinnamate.

To a stirred suspension of 1.10 g (2.73 mmol) of ethyl (E)-3-bromo-4-(trifluoromethanesulfonyloxy)cinnamate, 1.00 g (2.76 mmol) of 3-(1-adamantyl)-4-benzyloxyphenyl-boronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of Pd[P(C$_6$H$_5$)$_3$]$_4$ and 0.26 g (6.1 mmol) of LiCl in 20 ml of DME was added under Ar 3 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (10% EtOAc/hexane) yielded a yellow solid (0.33 g, 21%): m.p. 141–143° C.; R$_f$0.58 (20% EtOAc/hexane); $^1$H NMR (400 MHz, CDCl$_3$) δ 1.73, 2.16 (2 s, 12, AdCH$_2$), 2.04 (s, 3, AdCH), 1.34 (t, J=7.6 Hz, 3 CH$_3$), 4.27 (q, J=7.6 Hz, 2, CH$_2$), 5.17 (s, 2, CH$_2$), 6.46 (d, J=16.0 Hz, 1, HC=CCO), 6.95 (d, J=8.4 Hz, 1, ArH), 7.13 (dd, J=8.0, 2.0 Hz, 1, ArH), 7.29 (d, J=2.8 Hz, 1, ArH), 7.3–7.5 (m, 7, ArH), 7.68 (d, J=16.0 Hz, 1, C=CHCO), 7.82 ppm (d, J=2.0 Hz, 1, ArH).

Step 5: Ethyl (E)-4-[3-(1-adamantyl)-4-hydroxphenyl]-3-bromocinnamate.

A mixture of 0.30 g (0.52 mmol) of ethyl (E)-4-[3-(1-adamantyl)-4-benzyloxyphenyl]-3-bromocinnamate was stirred in 10 ml of CH$_2$Cl$_2$ at −78° C. under Ar while 3.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a pale-yellow solid (0.16 g, 63%): m.p. 210–212° C.; R$_f$0.35 (20% EtOAc/hexane); $^1$H NMR (300 MHz, CDCl$_3$) δ 1.78, 2.15 (2 s, 12, AdCH$_2$), 2.09 (s, 3, AdCH), 1.34 (t, J=7.6 Hz, 3 CH$_3$), 4.27 (q, J=7.6 Hz, 2, CH$_2$), 4.87 (s, 1, OH), 6.45 (d, J=16.0 Hz, 1, HC=CCO), 6.71 (d, J=8.4 Hz, 1, ArH), 7.14 (dd, J=8.4, 2.4 Hz, 1, ArH), 7.29 (d, J=2.4 Hz, 1, ArH), 7.34 (d, J=8.0 Hz, 1, ArH), 7.47 (dd, J=8.4, 2.4 Hz, 1, ArH), 7.63 (d, J=16.0 Hz, 1, C=CHCO), 7.82 ppm (d, J=1.6 Hz, 1, ArH).

Step 6: (E)-4-[3-(1-Adamantyl)-4-hydroxphenyl]-3-bromocinnamic acid.

To a solution of 0.15 g (0.31 mmol) of ethyl (E)-4-[3-(1-adamantyl)-4-hydroxyphenyl]-3-bromocinnamate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a pale-brown solid (0.02 g, 14%): m.p. 250–252° C.; R$_f$0.38 (EtOAc); $^1$H NMR (400 MHz, DMSO-d$_6$) δ 1.73, 2.09 (2 s, 12, AdCH$_2$), 2.03 (s, 3, AdCH), 6.60 (d, J=16.0 Hz, 1, HC=CCO), 6.84 (dd, J=8.0, 2.4 Hz, 1, ArH), 7.10 (dd, J=8.0, 1.6 Hz, 1, ArH), 7.15 (d, J=2.0 Hz, 1, ArH), 7.37 (d, J=8.0 Hz, 1, ArH), 7.58 (d, J=16.0 Hz, 1, C=CHCO), 7.73 (dd, J=8.0, 2.0 Hz, 1, ArH), 8.03 (s, 1, ArH), 9.56 (s, 1, OH), 12.47 ppm (s, 1, CO$_2$H); MS (EIHR): calcd. for C$_{25}$H$_{25}$BrO$_3$, 452.0987. found, 452.0988.

EXAMPLE 19

(E)-3-[3-(1-Adamantyl)4-hydroxphenyl]-4-hydroxycinnamic acid

Step 1: Ethyl (E)-3-bromo-4-methoxycinnamate.

To a suspension of 5.34 g (24.8 mmol) of 3-bromo-p-anisaldehyde and 11.97 g (86.6 mmol) of K$_2$CO$_3$ in 100 ml of anhydrous THF under Ar, 13.0 ml (65.5 mmol) of triethyl phosphonoacetate was added. The reaction mixture was stirred at room temperature for 4 days at which time the reaction was complete. The mixture was extracted with EtOAc, washed with brine and water, dried (MgSO$_4$), filtered, and concentrated. Flash column chromatography (20% EtOAc/hexane) yielded a white solid (5.85 g, 83%): m.p. 69–70° C.; R$_f$0.38 (20% EtOAc/hexane). $^1$H NMR (400 MHz, CDCl$_3$) δ 1.33 (t, J=7.6 Hz, 3, CH$_3$), 3.93 (s, 3, OCH$_3$), 4.25 (q, J=7.6 Hz, 2, CH$_2$), 6.31 (d, J=16.0 Hz, 1, HC=CCO), 6.90 (d, J=8.8 Hz, 1, ArH), 7.44 (dd, J=2.4, 8.8 Hz, 1, ArH), 7.75 (d, J=2.0 Hz, 1, ArH), 7.57 ppm (d, J=16.0 Hz, 1, C=CHCO).

Step 2: Ethyl (E)-3-bromo-4-hydroxycinnamate.

A mixture of 2.61 g (9.15 mmol) of ethyl (E)-3-bromo-4-methoxycinnamate was stirred in 10 ml of $CH_2Cl_2$ at 0° C. under Ar while 15.0 ml of 1.0 M $BBr_3$ in $CH_2Cl_2$ was added slowly over a period of 0.5 hour. The reaction mixture was stirred for 2 hours more, at which time the reaction was complete. The mixture was extracted with EtOAc, washed with brine and water, dried ($MgSO_4$), filtered, and concentrated. Flash column chromatography (20% EtOAc/hexane) yielded a pale-yellow solid (1.58 g, 63%): m.p. 101–103° C.; $R_f$ 0.25 (20% EtOAc/hexane); $^1$H NMR (400 MHz, $CDCl_3$) δ 1.33 (t, J=7.6 Hz, 3, $CH_3$), 4.25 (q, J=7.6 Hz, 2, $CH_2$), 5.72 (s, 1, OH), 6.31 (d, J=16.4 Hz, 1, HC=CCO), 7.02 (d, J=8.8 Hz, 1, ArH), 7.40 (dd, J=2.4, 8.8 Hz, 1, ArH), 7.55 (d, J=16.0 Hz, 1, C=CHCO), 7.65 ppm (d, J=2.0 Hz, 1, ArH).

Step 3: Ethyl (E)-3-bromo-4-(trifluoromethanesulfonyloxy)cinnamate.

To a solution of 1.55 g (5.71 mmol) of ethyl (E)-3-bromo-4-hydroxycinnamate and 1.0 ml (12.4 mmol) of pyridine in 50 ml of $CH_2Cl_2$ in a 0° C. ice bath under Ar, 1.60 ml (9.72 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% $NaHCO_3$, brine, and water, dried ($MgSO_4$), filtered, and concentrated to afford a white solid (2.19 g, 95% yield): m.p. 77–79° C.; $R_f$ 0.49 (20% EtOAc/hexane); $^1$H NMR (400 MHz, $CDCl_3$) δ 1.34 (t, J=7.6 Hz, 3, $CH_3$), 4.28 (q, J=7.6 Hz, 2, $CH_2$), 6.44 (d, J=16.4 Hz, 1, HC=CCO), 7.37 (d, J=8.4 Hz, 1, ArH), 7.52 (dd, J=2.4, 8.4 Hz, 1, ArH), 7.57 (d, J=16.4 Hz, 1, C=CHCO), 7.83 ppm (d, J=2.4 Hz, 1, ArH).

Step 4: Ethyl (E)-3-[3-(1-adamantyl)-4-benzyloxyphenyl]-4-hydroxycinnamate.

To a stirred suspension of 1.10 g (2.73 mmol) of ethyl (E)-3-bromo-4-(trifluoromethanesulfonyloxy)cinnamate, 1.00 g (2.76 mmol) of 3-(1-adamantyl)-4-benzyloxyphenylboronic acid [$^1$H NMR (300 MHz, $CDCl_3$) δ 1.77, 2.26 (2 s, 12, $AdCH_2$), 2.07 (s, 3, AdCH), 5.21 (s, 2, $CH_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of Pd[P($C_6H_5$)$_3$]$_4$ and 0.26 g (6.1 mmol) of LiCl in 20 ml of DME was added under Ar 3 ml of 2.0 M aq. $Na_2CO_3$. The reaction mixture was heated at reflux (80–85° C.) overnight, at which time the reaction was complete. The mixture was extracted with EtOAc. The extract was washed with brine and water, dried ($MgSO_4$), filtered, and concentrated. Flash column chromatography (10% EtOAc/hexane) yielded a white oil (0.41 g, 29%): $R_f$ 0.54 (20% EtOAc/hexane); $^1$H NMR (400 MHz, $CDCl_3$) δ 1.73, 2.16 (2 s, 12, $AdCH_2$), 2.04 (s, 3, AdCH), 1.34 (t, J=7.6 Hz, 3 $CH_3$), 4.27 (q, J=7.6 Hz, 2, $CH_2$), 5.16 (s, 2, $CH_2$), 6.46 (d, J=16.0 Hz, 1, HC=CCO), 7.02 (d, J=8.0 Hz, 1, ArH), 7.3–7.6 (m, 10, ArH), 7.68 ppm (d, J=16.0 Hz, 1, C=CHCO).

Step 5: Ethyl (E)-3-[3-(1-adamantyl)-4-hydroxphenyl]-4-hydroxycinnamate.

A mixture of 0.40 g (0.79 mmol) of ethyl (E)-3-[3-(1-adamantyl)-4-benzyloxyphenyl]-4-hydroxycinnamate was stirred in 10 ml of $CH_2Cl_2$ at −78° C. under Ar while 3.0 ml of 1.0 M $BBr_3$ in $CH_2Cl_2$ was added slowly over a period of 0.5 hour. The reaction mixture was stirred for 2 hours more, at which time the reaction was complete. The mixture was extracted with EtOAc, washed with brine and water, dried ($MgSO_4$), filtered, and concentrated. Flash column chromatography (20% EtOAc/hexane) yielded a pale-yellow solid (0.18 g, 55%): m.p. 198–200° C.; $R_f$ 0.28 (20% EtOAc/hexane); $^1$H NMR (300 MHz, $CDCl_3$) δ 1.79, 2.14 (2 s, 12, $AdCH_2$), 2.10 (s, 3, AdCH), 1.34 (t, J=7.6 Hz, 3 $CH_3$), 4.28 (q, J=7.6 Hz, 2, $CH_2$), 4.92 (s, 1, OH), 6.46 (d, J=16.0 Hz, 1, HC=CCO), 6.74 (d, J=7.6 Hz, 1, ArH), 7.15 (dd, J=8.0, 2.0 Hz, 1, ArH), 7.30 (d, J=2.4 Hz, 1, ArH), 7.36 (d, J=8.4 Hz, 1, ArH), 7.51 (dd, J=8.0, 2.4 Hz, 1, ArH), 7.59 (d, J=1.6 Hz, 1, ArH), 7.68 ppm (d, J=16.0 Hz, 1, C=CHCO).

Step 6: (E)-3-[3-(1-Adamantyl)-4-hydroxyphenyl]-4-hydroxycinnamic acid.

To a solution of 0.16 g (0.38 mmol) of ethyl (E)-3-[3-(1-adamantyl)-4-hydroxyphenyl]-4-hydroxycinnamate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried ($MgSO_4$), filtered, and concentrated to afford a pale-brown solid (0.07 g, 38%): m.p. 125–127° C.; $R_f$ 0.47 (EtOAc); $^1$H NMR (400 MHz, DMSO-$d_6$) δ 1.73, 2.11 (2 s, 12, $AdCH_2$), 2.04 (s,3, AdCH), 6.33 (d, J=16.0 Hz, 1, HC=CCO), 6.78 (dd, J=8.0, 2.4 Hz, 1, ArH), 6.91 (dd, J=8.0, 2.0 Hz, 1, ArH), 7.20 (dd, J=8.4, 2.0 Hz, 1, ArH), 7.27 (d, J=2.0 Hz, 1, ArH), 7.44 (dd, J=8.0, 2.4 Hz, 1, ArH), 7.48 (d, J=2.0 Hz, 1, ArH), 7.54 (d, J=16.0 Hz, 1, C=CHCO), 9.30 (s, 1, OH), 9.91 (s, 1, OH), 12.27 ppm (s, 1, $CO_2H$); MS (EIHR): calcd. for $C_{25}H_{26}O_4$, 390.1831. found, 390.1830.

EXAMPLE 20

9-[3-(1-Adamantyl)-4-hydroxphenyl]-6-(2-carboxyphenyl)-xanthen-3-one.

Step 1: 9-(Trifluoromethanesulfonyloxy)-6-(2-carboxyphenyl)xanthen-3-one.

To a solution of 1.67 g (5.02 mmol) of fluorescein and 1.0 ml (12.4 mmol) of pyridine in 50 ml of $CH_2Cl_2$ in a 0° C. ice bath under Ar, 1.60 ml (9.72 mmol) of trifluoromethanesulfonic anhydride was added slowly over a period of 0.5 hour. The reaction mixture was stirred for 4 hours, at which time the reaction was complete. The mixture was warmed to room temperature and extracted with EtOAc. The extract was washed with 10% HCl, 5% $NaHCO_3$, brine, and water, dried ($MgSO_4$), filtered, and concentrated to afford a white solid (1.71 g, 73% yield): m.p. 65–67° C.; $R_f$ 0.25 (20% EtOAc/hexane); $^1$H NMR (400 MHz, $CDCl_3$) δ 6.96 (d, J=8.8 Hz, 2, ArH), 7.03 (dd, J=2.4, 8.4 Hz, 2, ArH), 7.18 (d, J=8.0 Hz, 1, ArH), 7.30 (d, J=2.4 Hz, 2, ArH), 7.67–7.76 (m, 2, ArH), 8.06 ppm (dd, J=8.0, 1.6 Hz, 1, ArH).

Step 2: 9-[3-(1-Adamantyl)-4-benzylphenyl]-6-(2-carboxyphenyl)xanthen- 3-one.

To a stirred suspension of 1.00 g (2.15 mmol) of 9-(trifluoromethane-sulfonyloxy)-6-(2-carboxyphenyl)xanthen-3-one, 0.80 g (2.20 mmol) of 3-(1-adamantyl)-4-benzyloxyphenylboronic acid [$^1$H NMR (300 MHz, $CDCl_3$) δ 1.77, 2.26 (2 s, 12, $AdCH_2$), 2.07 (s, 3, AdCH), 5.21 (s, 2, $CH_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of Pd[P($C_6H_5$)$_3$]$_4$ and 0.26 g (6.1 mmol) of LiCl in 20 ml of DME was added under Ar 3 ml of 2.0 M aq. $Na_2CO_3$. The reaction mixture was heated at reflux (80–85° C.) overnight, at which time the reaction was complete. The mixture was extracted with EtOAc. The extract was washed with brine and water, dried ($MgSO_4$), filtered, and concentrated. Flash column chromatography (10% EtOAc/hexane) yielded a pale red (0.60 g, 44%): R$_f$ 0.45 (40% EtOAc/hexane); $^1$H NMR (400 MHz, CDCl$_3$) δ 1.74, 2.19 (2 s, 12, AdCH$_2$), 2.06 (s, 3, AdCH), 5.17 (s, 2, CH$_2$), 6.55 (dd, J=8.0, 2.0 Hz, 1, ArH), 6.68 (d, J=8.0 Hz, 1, ArH), 6.8–7.7 (m, 16, ArH), 8.05 ppm (d, J=8.0 Hz, 1, ArH).

Step 3: 9-[3-(1-Adamantyl)-4-hydroxphenyl]-6-(2-carboxyphenyl)xanthen-3-one.

A mixture of 0.60 g (0.95 mmol) of 9-[3-(1-adamantyl)-4-benzylphenyl]-6-(2-carboxyphenyl)xanthen-3-one was stirred in 10 ml of CH$_2$Cl$_2$ at –78° C. under Ar while 3.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a red solid (0.19 g, 37%): m.p. 170–172° C.; R$_f$ 0.25 (40% EtOAc/hexane); $^1$H NMR (400 MHz, DMSO-d$_6$) δ 1.74, 2.13 (2 s, 12, AdCH$_2$), 2.05 (s, 3, AdCH), 6.58 (dd, J=8.0, 2.0 Hz, 1, ArH), 6.61 (d, J=8.0 Hz, 1, ArH), 6.73 (d, J=2.4 Hz, 1, ArH), 6.76 (d, J=8.0 Hz, 1, ArH), 6.86 (d, J=8.0 Hz, 1, ArH), 7.30–7.37 (m, 4, ArH), 7.52 (d, J=1.6 Hz, 1, ArH), 7.72–7.83 (m, 2, ArH), 8.03 ppm (dd, J=8.0, 1.6 Hz, 1, ArH), 9.61 (s, 1, OH), 10.27 ppm (s, 1, CO$_2$H); MS (FABHR): calcd. for C$_{36}$H$_{30}$O$_5$, 543.2171. found, 543.2165.

EXAMPLE 21

6-[3-(1-Adamantyl)-4-hydroxphenyl]-4-methoxynaphthalene-2-carboxylic acid

Step 1: Ethyl 4-acetoxy-6-bromonaphthalene-2-carboxylate.

A mixture of 24.60 g (132.9 mmol) of 4-bromobenzaldehyde 30.66 g (176.0 mmol) of diethyl succinate in 20 ml of THF was added 200.0 ml of potassium tert-butoxide in 1.0 M 2-methyl-2-propanol over a period of 20 minutes. The reaction mixture was reflux overnight, then cooled to room temperature. The mixture was extracted with EtOAc, washed with 10% HCl, brine, and water, dried (MgSO$_4$), filtered, and concentrated to afford a yellow-brown oil. The mixture in 150.0 ml of acetic anhydride was added 10.0 g of sodium acetate and was reflux overnight, then cooled to room temperature. The mixture was extracted with EtOAc, washed with 10% HCl, brine, and water, dried (MgSO$_4$), filtered, and concentrated. Flash column chromatography (20% EtOAc/hexane) yielded a brown oil. (5.10 g, 11% yield): R$_f$ 0.22 (10% EtOAc/hexane); $^1$H NMR (400 MHz, CDCl$_3$) δ 1.43 (t, J=7.2 Hz, 3, CH$_3$), 2.60 (s, 3, CH$_3$), 4.42 (q, J=7.2 Hz, 2, CH$_2$), 7.40 (d, J=2.4 Hz, 1, ArH), 7.65 (dd, J=7.6, 2.4 Hz, 1, ArH), 7.84 (d, J=8.0 Hz, 1, ArH), 8.05 (s, 1, ArH), 8.46 ppm (s, 1, ArH).

Step 2: Ethyl 6-bromo-4-hydroxynaphthalene-2-carboxylate.

To a solution of 5.00 g (14.8 mmol) of ethyl 4-acetoxy-6-bromonaphthalene-2-carboxylate in 30 ml of EtOH was added 4.00 g (28.9 mmol) of K$_2$CO$_3$. This mixture was stirred at room temperature for 4 hours, at which time the reaction was complete. The mixture was extracted with EtOAc, and the extract was washed with 10% HCl, brine, and water, dried (MgSO$_4$), filtered and concentrated to afford a white solid (1.85 g, 42% yield): m.p. 134–136° C.; R$_f$ 0.14 (10% EtOAc/hexane); $^1$H NMR (400 MHz, CDCl$_3$) δ 1.43 (t, J=7.2 Hz, 3, CH$_3$), 4.42 (q, J=7.2 Hz, 2, CH$_2$), 5.73 (s, 1, OH), 7.45 (d, J=2.4 Hz, 1, ArH), 7.62 (dd, J=8.0, 2.4 Hz, 1, ArH), 7.76 (d, J=8.4 Hz, 1, ArH), 8.16 (s, 1, ArH), 8.40 ppm (d, J=2.0 Hz, 1, ArH).

Step 3: Ethyl 6-bromo-4-methoxynaphthalene-2-carboxylate.

To a suspension of 1.83 g (6.2 mmol) of ethyl 6-bromo-4-hydroxynaphthalene-2-carboxylate and 3.00 g (21.7 mmol) of K$_2$CO$_3$ in 50 ml of acetone at room temperature, 2.0 ml (16.1 mmol) of methyl iodide was added. The reaction mixture was stirred at room temperature for 4 hours at which time the reaction was complete. The mixture was filtered, washed with EtOAc, dried (MgSO$_4$), filtered, and concentrated. Flash column chromatography (10% EtOAc/hexane) yielded a pale white solid (1.41 g, 73%): m.p. 98–100° C.; R$_f$ 0.42 (10% EtOAc/hexane). $^1$H NMR (400 MHz, CDCl$_3$) δ 1.45 (t, J=7.2 Hz, 3, CH$_3$), 4.06 (s, 3, OCH$_3$), 4.44 (q, J=7.6 Hz, 2, CH$_2$), 7.42 (d, J=1.6 Hz, 3, ArH), 7.62 (dd, J=8.0, 2.4 Hz, 1, ArH), 7.77 (d, J=8.4 Hz, 1, ArH), 8.17 (s, 1, ArH), 8.46 ppm (d, J=1.6 Hz, 1, ArH).

Step 4: Ethyl 6-[3-(1-adamantyl)-4-benzyloxyphenyl]-4-methoxynaphthalene-2-carboxylate.

To a stirred suspension of 1.00 g (3.23 mmol) of ethyl 6-bromo-4-methoxynaphthalene-2-carboxylate, 1.20 g (3.31 mmol) of 3-(1-adamantyl)-4-benzyloxyphenylboronic acid [$^1$H NMR (300 MHz, CDCl$_3$) δ 1.77, 2.26 (2 s, 12, AdCH$_2$), 2.07 (s, 3, AdCH), 5.21 (s, 2, CH$_2$), 7.06 (d, J=8.2 Hz, 1, ArH), 7.3–7.5 (m, 5, ArH), 8.03 (d, J=7.8 Hz, 1, ArH), 8.19 ppm (s, 1, ArH)], 0.32 g (0.28 mmol) of Pd[P(C$_6$H$_5$)$_3$]$_4$ and 0.26 g (6.1 mmol) of LiCl in 20 ml of DME was added under Ar 2.8 ml of 2.0 M aq. Na$_2$CO$_3$. The reaction mixture was heated at reflux (80–85° C.) overnight, at which time the reaction was complete. The mixture was extracted with EtOAc. The extract was washed with brine and water, dried (MgSO$_4$), filtered, and concentrated. Flash column chromatography (20% EtOAc/hexane) yielded a pale-yellow solid (1.10 g, 63%): m.p. 75–77° C.; R$_f$ 0.36 (10% EtOAc/hexane); $^1$H NMR (400 MHz, CDCl$_3$) δ 1.80, 2.19 (2 s, 12, AdCH$_2$), 2.10 (s, 3, AdCH), 1.45 (t, J=7.6 Hz, 3 CH$_3$), 4.09 (s, 3, OCH$_3$), 4.45 (q, J=7.6 Hz, 2, CH$_2$), 5.18 (s, 2, CH$_2$), 6.99 (d, J=8.0 Hz, 1, ArH), 7.3–7.45 (m, 5, ArH), 7.41 (d, J=1.6 Hz, 1, ArH), 7.56 (dd, J=8.0, 2.4 Hz, 1, ArH), 7.60 (d, J=2.8 Hz, 1, ArH), 7.79 (dd, J=8.0, 2.0 Hz, 1, ArH), 7.93 (d, J=8.4 Hz, 1, ArH), 8.22 (s, 1, ArH), 8.42 ppm (d, J=1.6 Hz, 1, ArH).

Step 5: Ethyl 6-[3-(1-adamantyl)-4-hydroxphenyl]-4-methoxynaphthalene- 2-carboxylate.

A mixture of 1.05 g (1.92 mmol) of ethyl 6-[3-(1-adamantyl)-4-benzyloxyphenyl]-4-methoxynaphthalene-2-carboxylate was stirred in 30 ml of CH$_2$Cl$_2$ at –78° C. under Ar, and 3.0 ml of 1.0 M BBr$_3$ in CH$_2$Cl$_2$ was added slowly over a period of 0.5 hour. The reaction mixture was stirred for 2 hours more, at which time the reaction was complete. The mixture was extracted with EtOAc, washed with brine and water, dried (MgSO$_4$), filtered, and concentrated. Flash column chromatography (20% EtOAc/hexane) yielded a pale-yellow solid (0.41 g, 47%): m.p. 110–112° C.; R$_f$ 0.39 (20% EtOAc/hexane); $^1$H NMR (400 MHz, CDCl$_3$) δ 1.81, 2.21 (2 s, 12, AdCH$_2$), 2.12 (s, 3, AdCH), 1.46 (t, J=7.6 Hz, 3 CH$_3$), 4.09 (s, 3, OCH$_3$), 4.44 (q, J=7.6 Hz, 2, CH$_2$), 4.89 (s, 1, OH), 6.77 (d, J=8.4 Hz, 1, ArH), 7.41 (d, J=1.6 Hz, 1, ArH), 7.45 (dd, J=8.0, 2.0 Hz, 1, ArH), 7.58 (d, J=2.0 Hz, 1, ArH), 7.77 (dd, J=8.0, 2.0 Hz, 1, ArH), 7.93 (d, J=8.4 Hz, 1, ArH), 8.22 (s, 1, ArH), 8.40 ppm (d, J=1.6 Hz, 1, ArH).

Step 6: 6-[3-(1-Adamantyl)-4-hydroxphenyl]-4-methoxynaphthalene-2-carboxylic acid.

To a solution of 0.40 g (0.87 mmol) of ethyl 6-[3-(1-adamantyl)-4-hydroxyphenyl]-4-methoxynaphthalene-2-carboxylate in 40 ml of 75% aq. EtOH, 1 pellet of NaOH was added. This mixture was stirred at 80–85° C. for 2 hours, at which time the reaction was complete, then was cooled to room temperature, acidified with 10% HCl, and extracted with EtOAc. The extract was washed with brine and water, dried (MgSO$_4$), filtered, and concentrated to afford a yellow solid (0.2 g, 53%): m.p. 293–295° C.; R$_f$ 0.35 (EtOAc); $^1$H NMR (400 MHz, DMSO-d$_6$) δ 1.76, 2.16 (2 s, 12, AdCH$_2$), 2.07 (s, 3, AdCH), 4.05 (s, 3, OCH$_3$), 6.92 (dd, J=8.4, 2.4 Hz, 1, ArH), 7.37 (d, J=1.6 Hz, 1, ArH), 7.45 (dd, J=8.0, 2.0 Hz, 1, ArH), 7.46 (s, 1, ArH), 7.86 (dd, J=8.0, 2.4 Hz, 1, ArH), 8.09 (d, J=8.4 Hz, 1, ArH), 8.20 (s, 1, ArH), 8.26 (s, 1, ArH), 9.58 (s, 1, OH), 13.02 ppm (s, 1, CO$_2$H); MS (FABHR): calcd. for C$_{28}$H$_{28}$O$_4$, 428.1988. found, 428.1982.

EXAMPLE 22

Synthesis of (E)-4-[3-(1-Adamantyl)-4-hydroxphenyl]3-(3-aminopropoxy)cinnamic Acid and (E)-4-[3-(1-Adamantyl)-4-hydroxphenyl]3-(3-acetamidopropoxy)cinnamic Acid The synthesis of (E)-4-[3-(1-Adamantyl)-4-hydroxyphenyl]3-(3-aminopropoxy)cinnamic Acid and (E)-4-[3-(1-Adamantyl)-4-hydroxyphenyl]3-(3-acetamidopropoxy)cinnamic Acid is described in the steps below and depicted in Scheme 6.

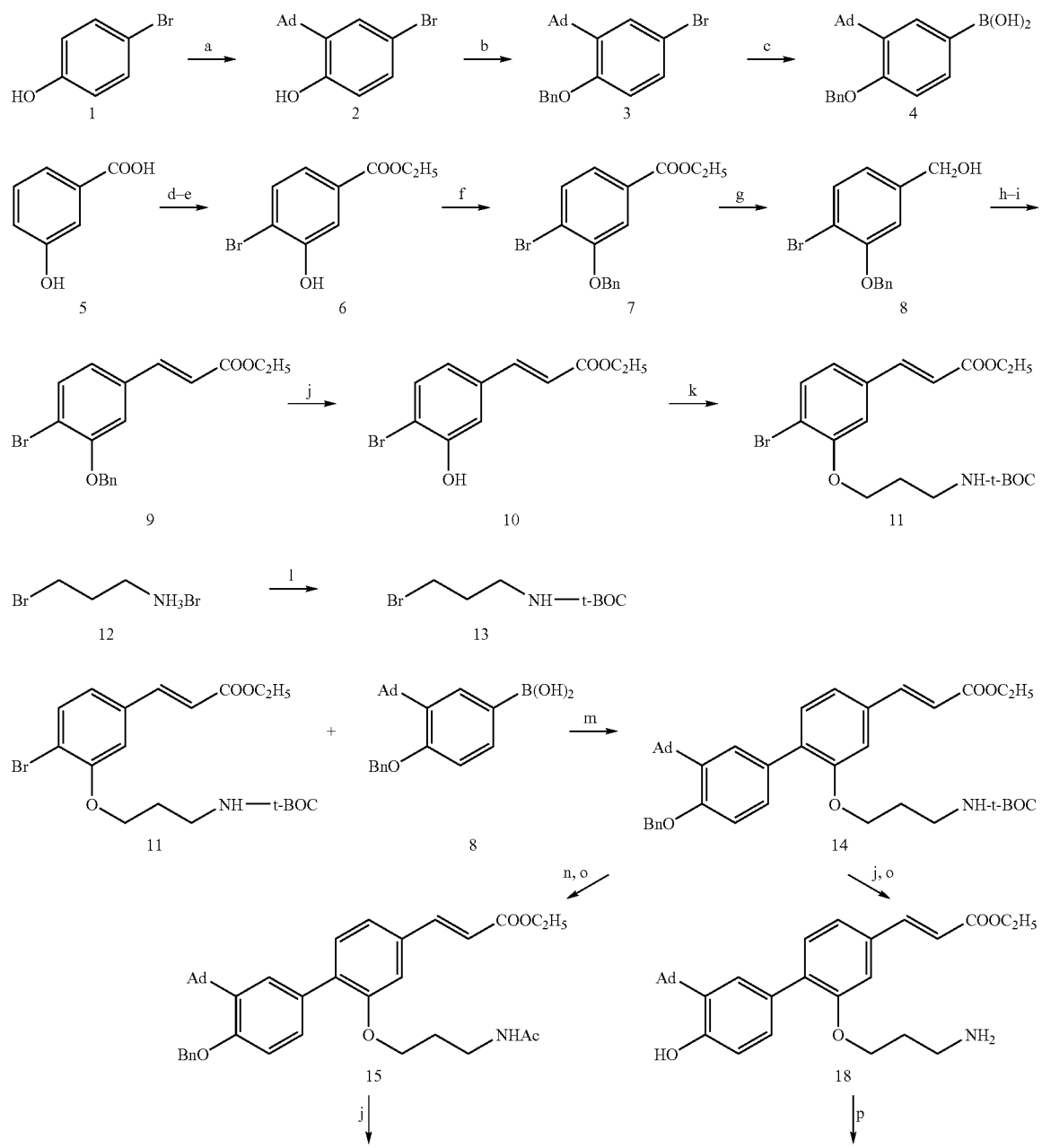

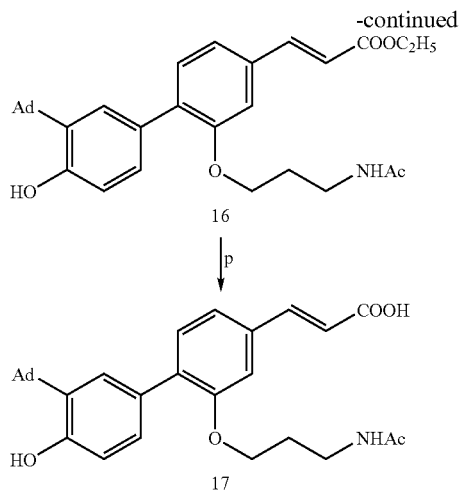

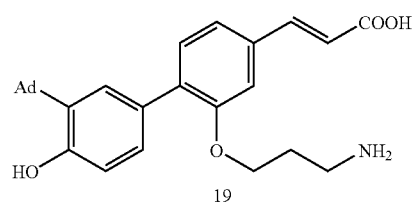

Step 1: Synthesis of ethyl 4-bromo-3-hydroxybenzoate (6).

To a solution of 3-hydroxybenzoic acid 5 (18.2 g, 0.132 mol) in 180 ml of glacial acetic acid cooled in a water bath was slowly added over a period of 2 h bromine (21.1 g, 0.132 mmol) in 70 ml of acetic acid. The solution was stirred overnight. After removing bromine and 160 ml of acetic acid under reduced pressure, the mixture was cooled to 0° C., filtered, washed (50 ml of cold water), and dried under vacuum to give a white solid. Crystallization ($H_2O$) gave 4-bromo-3-hydroxybenzoic acid as white crystals (5.5 g, 19%).

To a mixture containing 4-bromo-3-hydroxybenzoic acid (5.0 g, 0.023 mol) and 5 ml of EtOH in 150 ml of benzene was added 1 ml of $MeSO_3H$. The mixture was heated at reflux for 10 h using a Dean-Stark trap to collect water, then concentrated. The residue was dissolved in $CH_2Cl_2$, washed (water, 5% $NaHCO_3$, and brine), dried ($Na_2SO_4$), and concentrated. The crude product was chromatographed (EtOAc/hexane) to gave a white solid (5.1 g, 90%): $^1H$ NMR (300 MHz, $CDCl_3$) δ 1.39 (t, J=7.2 Hz, 3 H), 4.37 (q, J=7.2 Hz, 2 H), 5.75 (s, 1 H), 7.48 (d, J=8.1 Hz, 1 H), 7.55 (d, J=8.1 Hz, 1 H), 7.68 ppm (s, 1 H).

Step 2: Synthesis of ethyl 4-bromo-3-benzyloxybenzoate (7).

To a suspension of 4.5 g (18.4 mmol) of 6 and 4.1 g (30 mmol) of $K_2CO_3$ in 150 ml of acetone under Ar was added 3.4 g (20 mmol) of BnBr. The mixture was heated at reflux for 15 h, concentrated, then diluted with 100 ml of $CH_2Cl_2$, washed (water, 1 N HCl, and brine), and dried ($Na_2SO_4$). Concentration and chromatography (EtOAc/hexane) afforded 5.2 g (84%) of 7 (white solid): $^1H$ NMR (300 MHz, $CDCl_3$) δ 1.39 (t, J=7.2 Hz, 3 H), 4.37 (q, J=7.2 Hz, 2 H), 5.21 (s, 2 H), 7.39 (m, 3 H), 7.50 (in, 3 H), 7.63 ppm (m, 2 H).

Step 3: Synthesis of 4-bromo-3-benzyloxybenzyl alcohol (8).

To 3.35 g (10 mmol) of 7 in 25 ml of $CH_2Cl_2$ under Ar in a dry ice-acetone bath was slowly added 20 ml 1.0 M DIBAL with stirring. After stirring for 2 h, 20 ml of 1 N HCl and 50 ml of $CH_2Cl_2$ were added, and the mixture was stirred for 0.5 h, then washed (water and brine), and dried ($Na_2SO_4$). Concentration and chromatography (EtOAc/hexane) afforded 2.78 g (91%) of 8 (white solid): $^1H$ NMR (300 MHz, $CDCl_3$) δ 4.63 (d, J=5.7 Hz, 2 H), 6.83 (d, J=8.1 Hz, 1 H), 7.00 (s, 1 H), 7.40–7.33 (m, 3 H), 7.5–7.42 ppm (m, 3 H).

Step 4: Synthesis of ethyl (E)-4-bromide-3-benzyloxycinnamate (9).

To a stirred solution of 8 (2.77 g, 10 mmol) in 30 ml of $CH_2Cl_2$ cooled in an ice bath was slowly added 1.5 mmol of PCC. This mixture was stirred for 5 h at room temperature. $Et_2O$ (50 ml) was added. Filtration and concentration gave the related aldehyde as a white solid), which was used in the next step without further purification.

To 0.33 g (1.5 mmol) of triethyl phosphonoacetate in 10 ml of anhydrous $Et_2O$ under Ar in a dry ice-acetone bath was added to 1.5 ml of 0.91 M $KN(SiMe_3)_2$ in THF. After stirring for 0.5 h, 0.33 g (1.5 mmol) of aldehyde in 10 ml of $Et_2O$ was slowly added to the solution cooled in the dry ice-acetone bath. After stirring for 1 h more, the mixture was allowed to warm to room temperature, stirred overnight, poured into 50 ml of water and 1 ml of HOAc, extracted into 20 ml of $Et_2O$, washed (water and brine), and dried ($Na_2SO_4$). Concentration and chromatography (EtOAc/hexane) afforded 0.28 g (91%) of 9 as a white solid: $^1H$ NMR (300 MHz, $CDCl_3$) δ 1.33 (t, J=7.2 Hz, 3 H), 4.26 (q, J=6.9 Hz, 2 H), 5.18 (s, 2 H), 6.39 (d, J=15.9 Hz, 1 H), 7.01 (d, J=8.4 Hz, 1 H), 7.06 (s, 1 H), 7.40–7.33 (m, 3 H), 7.48 (s, 1 H), 7.50 (d, J=6.6 Hz, 1 H), 7.57 (d, J=8.4 Hz, 1 H), 7.58 ppm (d, J=15.9 Hz, 1 H).

Step 5: Synthesis of ethyl (E)-4-bromide-3-hydroxycinnamate (10).

A solution of 9 (260 mg, 0.72 mmol), 1.5 ml of 1 M $BBr_3$ in $CH_2Cl_2$ and 5 ml of $CH_2Cl_2$ was stirred at −78° C. under Ar for 2 h, then diluted with 10 ml of water and 20 ml of $CH_2Cl_2$. The solution was washed (water and brine), dried ($Na_2SO_4$), and concentrated. Flash chromatography gave a white solid (180 mg, 92%): $^1H$ NMR (300 MHz, $CDCl_3$) δ 1.34 (t, J=6.9 Hz, 3 H), 4.27 (q, J=7.2 Hz, 2 H), 5.62 (s, 1 H), 6.42 (d, J=15.9 Hz, 1 H), 6.98 (d, J=8.4 Hz, 1 H), 7.18 (s, 1 H), 7.48 (d, J=8.4 Hz, 1 H), 7.58 ppm (d, J=15.9 Hz, 1 H).

Step 6: Synthesis of ethyl (E)-4-bromide-3-(3-t-butoxycarboxy-amidocarbonate-3-aminopropoxy)cinnamate (11).

To a suspension of 320 mg (1.18 mmol) of 10 and 500 mg (3.62 mmol) of $K_2CO_3$ in 50 ml of acetone under Ar was added 480 mg (1.98 mmol) 3-bromo-N-(t-butylcarbonate)propylamine (13). The mixture was heated at reflux for 20 h. After removal the solvent, the residue was extracted ($CH_2Cl_2$), washed (water, 1 N HCl, and brine), and dried ($Na_2SO_4$). Concentration and chromatography (EtOAc/hexane) afforded 410 mg (81%) of 11 as a white solid: mp 65–67° C.; $^1$H NMR (300 MHz, $CDCl_3$) δ 1.34 (t, J=7.2 Hz, 3 H), 1.44 (s, 9 H), 2.07 (t, J=6.0 Hz, 2 H), 3.40(q, J=5.7 Hz, 2 H), 4.13 (t, J=5.7 Hz, 2 H), 4.26 (q, J=7.2 Hz, 2 H), 5.22 (s, 1 H), 6.47 (d, J=15.9 Hz, 1 H), 7.00(s, 1 H), 7.01 (d, J=6.3 Hz, 1 H), 7.54 (d, J=8.7 Hz, 1 H), 7.60 ppm (d, J=15.9 Hz, 1 H); IR (film) 3425, 2980, 1706, 1642, 1516, 1486, 1247, 1178 $cm^{-1}$. MALDI FAB calc. $C_{19}H_{26}BrNO_5$ 428.3. found 428.1.

Step 7: Synthesis of 3-bromo-N-(t-butoxycarbonyl)propylamine (13).

To a suspension of 3-bromopropylamine hydrobromide (4.4 g, 20 mmol) and 3 ml of $Et_3N$ cooled in an ice bath was slowly added di-(t-butyl)dicarbonate (5.5 g, 25 mmol) in 20 ml of $CH_2Cl_2$. The mixture was stirred at 0° C. for 1 h, then at room temperature overnight, filtered, and extracted ($CH_2Cl_2$). The organic phase was washed (water and brine), and dried ($Na_2SO_4$). Concentration and chromatography (EtOAc/hexane) afforded 3.95 g (83%) of 11 as a colorless liquid; $^1$H NMR (300 MHz, $CDCl_3$) δ 1.45 (s, 9 H), 2.05 (m, 2 H), 3.28 (q, J=6.3 Hz, 2 H), 3.45 (t, J=6.3 Hz, 2 H), 4.66 ppm (s, 1 H).

Step 8: Synthesis of ethyl (E)-4-[3-(1-adamantyl)-4-benzyloxyphenyl]-3-(3-t-butoxycarboxamidopropoxy)cinnamate (14).

To 321 mg (0.75 mmol) of 11, 362 mg (1 mmol) of 3-(1-adamantyl)-4-benzyloxyphenylboronic acid, and 60 mg (0.052 mmol) of $Pd(PPh_3)_4$ in 5 ml of DME was added under Ar 1 ml of 2 M aq. $Na_2CO_3$. The mixture was heated at reflux for 20 h, then extracted (EtOAc). The extracts were washed (water and brine), dried ($MgSO_4$), filtered, and concentrated. Flash chromatography gave a yellow solid (410 mg, 83%): mp 73–75° C.; $^1$H NMR (300 MHz, $CDCl_3$) δ 1.35 (t, J=6.9 Hz, 3 H), 1.43 (s, 9 H), 1.72 (s, 6 H), 1.95 (m, 2 H), 2.04 (s, 3 H), 2.17 (s, 6 H), 3.24 (d, J=5.4 Hz, 2 H), 4.03 (t, J=5.7 Hz, 2 H), 4.28 (q, J=6.6 Hz, 2 H), 4.55 (s, 1 H), 5.16 (s, 2 H), 6.45 (d, J=15.9 Hz, 1 H), 7.00 (d, J=8.7 Hz, 1 H), 7.11 (s, 1 H), 7.20 (d, J=7.8 Hz, 1 H), 7.45–7.34 (m, 6 H), 7.51 (s, 1 H), 7.53 (d, J=7.2 Hz, 1 H), 7.68 ppm (d, J=15.9 Hz, 1 H); IR (KBr) 3366, 2907, 2853, 1711, 1637, 1491, 1237, 1173 $cm^{-1}$. MALDI FAB calc. $C_{42}H_{51}N)_6$ 665.9. found 688.1 ($M^+$+Na).

Step 9: Synthesis of ethyl (E)-4-[3-(1-adamantyl)-4-benzyloxyphenyl]-3-(3-acetamidopropoxy)cinnamate (15).

To 14 (400 mg, 0.6 mmol) in 10 ml of EtOH was added 1 ml of conc. HCl. The mixture was heated at reflux for 1 h. The residue obtained on concentration was treated with 20 ml of $CH_2Cl_2$, 1 ml of pyridine, and 1 ml of $Ac_2O$ with stirring overnight at room temperature. The solution was washed (water and brine), dried ($MgSO_4$), filtered, and concentrated. Flash chromatography gave a white solid (280 mg, 77%): mp 80–82° C.; $^1$H NMR (300 MHz, $CDCl_3$) δ 1.35 (t, J=7.2 Hz, 3 H), 1.45 (s, 2 H), 1.72 (s, 3 H), 2.04 (s, 6 H), 2.15 (s, 6 H), 3.37 (q, J=5.4 Hz, 2H), 4.12 (t, J=5.1 Hz, 2 H), 4.28 (q, J=7.2 Hz, 2 H), 5.15 (s, 2 H), 5.67 (s, 1 H), 6.45 (d, J=16.2 Hz, 1 H), 7.00 (d, J=7.8 Hz, 1 H), 7.09 (s, 1 H), 7.22 (d, J=7.8 Hz, 1 H), 7.42–7.26 (m, 6 H), 7.49 (s, 1 H), 7.50 (d, J=8.1 Hz, 1 H), 7.69 ppm (d, J=16.2); IR (KBr) 3293, 2912, 2853, 1716, 1642, 1491, 1237, 1178 $cm^{-1}$. MALDI FAB calc. $C_{39}H_{45}NO_5$ 607.8. found 607.3

Step 10: Synthesis of ethyl (E)-4-[3-(1-adamantyl)-4-hydroxphenyl]-3-(3-acetamidopropoxy)cinnamate (16).

A solution of 15 (303 mg, 0.5 mmol) and 1.5 ml of 1 M $BBr_3$ in $CH_2Cl_2$ and 5 ml of $CH_2Cl_2$ was stirred at −78° C. under Ar for 2 h then 10 ml of water and 20ml of $CH_2Cl_2$ ere added. The organic phase was washed (water and brine), dried ($Na_2SO_4$), filtered, and concentrated. Flash chromatography gave a white solid (226 mg, 77%): mp 110–113° C.; $^1$H NMR (300 MHz, $CDCl_3$) δ 1.35 (t, J=6.9 Hz, 3 H), 1.44 (s, 2 H), 1.77 (s, 6 H), 2.04 (s, 3 H). 2.08 (s, 3 H), 2.14 (s, 6 H), 3.38 (q, J=5.4 Hz, 2 H), 4.13 (t, J=6.3 Hz, 2 H), 4.27 (q, J=7.2 Hz, 2 H), 5.81 (s, 1 H), 6.30 (s, 1 H), 6.44 (d, J=15.9 Hz, 1 H), 6.75 (d, J=8.1 Hz, 1 H), 7.09 (s, 1 H), 7.20 (d, J=6.5 Hz, 1 H), 7.26 (d, J=8.1 Hz, 1 H), 7.33 (d, J=8.1 Hz, 1 H), 7.40 (s, 1 H), 7.68 ppm (d, J=15.9 Hz, 1 H); IR (KBr) 3408, 2907, 2853, 1706, 1637, 1496, 1266, 1178 $cm^{-1}$. MALDI FAB calc. $C_{32}H_{39}NO_5$ 517.7. found 517.3

Step 11: Synthesis of (E)-4-[3-(1-adamantyl)-4-hydroxphenyl]-3-(3-acetamidopropoxy)cinnamate (17).

To a suspension of 16 (190 mg, 0.387 mmol) in 10 ml of MeOH was added NaOH (100 mg, 2.5 mmol). The mixture was stirred at reflux under Ar for 1 h, cooled to room temperature, acidified (1 N HCl), and extracted (EtOAc). The extracts were washed (water and brine), dried ($MgSO_4$), and concentrated to afford a white solid (170 mg, 94%): mp 195–19° C.; $^1$H NMR (300 MHz, DMSO) δ 1.73 (s, 6 H), 1.77 (s, 3 H), 1.78 (m, 2 H), 2.03(s, 3 H), 2.10 (s, 6 H), 3.17(d, J=5.4 Hz, 2 H), 4.06 (b, s, 2 H), 6.63 (d, J=15.9 Hz, 1 H), 6.80 (d, J=8.1 Hz, 1H), 7.21 (d, J=8.7 Hz, 1 H), 7.29 (s, 2 H), 7.37 (s, 1 H), 7.61 (d, J=15.9 Hz, 1 H), 7.86 (s, 1 H), 9.41 ppm (s, 1 H). MALDI FAB calc. $C_{30}H_{35}NO_5$, 489.6. found 489.2

Step 12: Synthesis of ethyl (E)-4-t3-(1-adamantyl)-4-hydroxphenyl]-3-(aminopropoxy)cinnamate (18).

A solution of 14 (500 mg, 0.75 mmol) and 1.5 ml of 1 M $BBr_3$ in $CH_2Cl_2$ and 20 ml of $CH_2Cl_2$ was stirred at 78° C. under Ar for 2 h, then diluted with 10 ml of water and 20 ml of $CH_2Cl_2$. The organic phase was washed (water and brine), dried ($Na_2SO_4$), and concentrated to give a pale-yellow solid. The solid dissolved in 20 ml of EtOH and 1.5 ml of conc. HCl was heated at reflux for 2 h under Ar then concentrated. Before 20 ml of MeOH and 200 mg $NaHCO_3$ were added. This mixture was stirred for 1 h under Ar and concentrated. Flash chromatography gave a white solid (278 mg, 78%): mp 181–183° C.; $^1$H NMR (300 MHz, $CDCl_3$) δ 1.34 (t, J=7.2 Hz, 3 H), 1.76 (s, 6 H), 1.94 (m, 2 H), 2.05 (s, 3 H), 2.15 (s, 6 H), 2.85 (m, 2H), 3.74 (s, 2 H), 4.09 (s, 2 H), 4.28 (q, J=7.5 Hz, 2 H), 5.71 (s, 1 H), 6.43 (d, J=15.9 Hz, 1 H), 6.62 (d, J=7.8 Hz, 1 H), 7.08 (s, 1 H), 7.17 (d, J=7.2 Hz, 1 H), 7.20 (d, J=8.4 Hz, 1 H), 7.30 (s, 1 H), 7.32 (d, J=7.5 Hz, 1 H), 7.68 ppm (d, J=15.9 Hz, 1 H); IR (KBr) 3244, 2902, 2853, 1706, 1632, 1398, 1256, 1173 $cm^1$. MALDI FAB calc. $C_{30}H_{37}NO_4$, 475.6. found 476.3.

Step 13: Synthesis of (E)-4-[3-(1-adamantyl)-4-hydroxphenyl]-3-(aminopropoxy)cinnamate (19).

To a suspension of 18 (260 mg, 0.547 mmol) in 10 ml MeOH was added NaOH (100 mg, 2.5 mmol) in 1 ml water. This mixture was stirred at reflux under Ar for 1 h, cooled (room temperature), acidified (1 N HCl), then concentrated. The resultant solid was diluted with 5 ml of water and 10 ml of $Et_2O$. This mixture was stirred for 1 h, filtered, and dried under vacuum to give a white solid (236 mg, 89%): mp 238–240° C.; $^1$H NMR (300 MHz, $CD_3OD$) δ 1.87 (s, 6 H), 2.11 (s, 3 H), 2.24 (s, 6 H), 3.08 (t, J=7.5 Hz, 2 H), 4.20 (t, J=6.0 Hz, 2 H), 6.56 (d, J=16.2 Hz, 1 H), 6.81 (d, J=8.4 Hz, 1 H), 7.23 (d, J=8.4 Hz, 1 H), 7.30 (d, J=8.4 Hz, 2 H), 7.33 (s, 2 H), 7.73 ppm (d, J=16.2 Hz, 1 H)

Pharmacology

The following materials were used: Recombinant interleukin 3 (IL-3), granulocyte growth stimulating factor (G-CSF), granulocyte/macrophage stimulating factor (GM-CSF), stem cell antibodies factor (SCF), and JNK, phospho-JNK, p38, phospho-p38, ERK and phospho-ERK Poly-(ADP) ribose. 3-Cl-AHPC was synthesized as recently described (See Zhang, Y, et al., *Blood* 100: 2917–2925 (2002).)

Cell Growth: IL-3-transfected M07e cells have been described by Thacker, D. J., et al., *Leukemia* 8: 871–877 (1994). Cells were grown in RPMI supplemented with 5 percent heat-inactivated fetal bovine serum (FBS) and 25 µg/ml gentamycin in a 95% $O_2$, 5% $CO_2$, and 100% humidity environment. Leukemic cells were obtained from patients who met the criteria for the diagnosis of AML or CML in blast crisis (see Table 1). Studies were approved by the Wayne State University Institutional Review Board. Informed consent was obtained from all patients. Leukemic blasts from patients were isolated using Ficoll hypaque. Cells at the interface between plasma and red blood cells were diluted with sterile PBS, then layered over Ficoll hypaque (1.077 density), and the leukemic cells collected at the interface. The sample to be studied represented greater than 90% blasts. The patient leukemia samples were grown in RPMI medium supplemented with 10% FBS, gentamycin (25 µg/ml), IL-3 (20 ng/ml), SCF (25 ng/ml), GM-CSF (20 ng/ml) and G-CSF (20 ng/ml). Cell growth was assessed using a cell proliferation kit.

Western Blots: Western blots were performed according to the protocol of Sheikh, M. S., et al., (*Oncogene*, 9: 3407–3415 (1994)). Logarithmically growing cells were treated with 3-Cl-AHPC for various times and cells were harvested and lysed in Laemmli lysis buffer (0.5 M Tris-HCl, pH 6.8, 0.002M EDTA, 10% glycerol, 10% sodium dodecyl sulfate (SDS), and 5% β-mercaptoethanol). Protein lysates (50 µg/lane) were electrophoresed on 12% SDS-polyacrylamide gels and transferred to nitrocellulose membranes. Membranes were blocked with 5% nonfat dried milk in PBS/0.5% Tween 20 and then incubated with the appropriate antibodies. Horseradish peroxidase-conjugated rabbit anti-mouse IgG was used as the secondary antibody, and bands were developed using the Amersham ECL non-radioactive method.

Apoptosis Quantification: Staining of apoptotic cells was performed as described by Gavreli, Y., et al., (J. Cell Biol. 119: 493–501 (1992)) and Whitacre, C. M., et al., (Cancer Res. 55: 3697–3701 (1995)). After 3-Cl-AHPC treatment, cells were harvested, washed with PBS and resuspended at $1 \times 10^6$ cells/ml. Cell suspensions (50 µl) were stained with 5 ml of acridine orange solution (100 mg/ml) in PBS in the dark. Cells displaying fragmented DNA were detected using a fluorescent microscope. Apoptotic cells were also detected using a kit. Cells that incorporated fluorescein labeled deoxyuridine triphosphate were detected using flow cytometry.

Flow Cytometry: Flow cytometry was performed on a flow cytometer equipped with an argon ion laser tuned to 15 mW at 488 nM for fluorescence excitation and light scattering. Fluorescein isothiocyanate (FITC) fluorescence was detected using a 530/30 nm band pass filter and propidium iodide (PI) fluorescence was reflected with a 560-nm short pass dichroic filter using a 585/42-nm band pass filter. The doublet discrimination module was used to identify cell aggregates (Sharpless, T., et al., Acta Cytologica 19: 577–581 (1975)). Typically, 20,000 events of list mode data were saved and analyzed.

Activation of caspases-1, -2, -3, -6, -8 and -9 was assessed using a caspase activation kit.

Leukemia Colony Formation: Leukemic blasts ($1 \times 10^5$ cells) from patient 1 (Table 1) were isolated as described above and cultured in methylcellulose supplemented with 20% FCS, SCF, and IL-3, GM-CSF and G-CSF at a final concentration of 10 ng per ml, cells were incubated for 14 days at 37° C. in a 5% $CO_2$ humidified atmosphere in the presence and absence of 3-Cl-AHPC after which time colonies (>40 cells) were counted.

CFU-GM Colony Formation: The CFU-GM colony assay was performed as described in Parchment et al., (J. Natl. Cancer Inst. 86: 273–280 (1994)).

Tumor Maintenance: Murine AML1498 cells were maintained in the mouse strain of origin (C57BL/6) and transplanted into this same inbred strain for chemotherapy trials. Individual mouse body weights for each experiment were within five grams, and all mice were more than 20 grams (mean) at the start of therapy. Mice were supplied food and water ad libitum.

3-Cl-AHPC in vivo therapy: Mice were randomly pooled into groups of five and implanted intravenously with varying numbers of AML 1498 cells ($5 \times 10^6$, $5 \times 10^4$, $5 \times 10^2$) prepared from mouse spleens demonstrating approximately 80% replacement of the spleen with leukemic cells. Treatment was started the day after implantation of AML cells.

End Points for Assessing Antitumor Activity: The following quantitative endpoints were used to assess antitumor activity a) Percent Increase in Lifespan (% ILS): For leukemic mice:

% ILS=(T−C)/C×100; in which C=median day of death of control group and T=median day of death of treated group. Survival was the endpoint; with moribund mice sacrificed. Cause of death was verified by necropsy.

b) Calculation of Tumor Cell Kill: For leukemic survival trials, the $\log_{10}$ cell kill was calculated from the following formula:

$$\text{Log}_{10}\text{Cell Kill Total (gross)} = \frac{T - C}{(3.32)(Td)};$$

where T is median day of death for treated group and C is median day of death for control group (Corbett, T. H., et al., Invest. New Drugs, 17: 17–27 (1999) and Teicher, B. A., In vivo tumor response end points, In *Tumor Models in Cancer Research*, B. Teicher, editor, Humana Press Inc./Totowa, N.J., pp. 593–616 (2001)). Td is determined from differences in the median days of death of the titered control groups.

Activity Rating for AML1498: For comparison of activity with standard agents the $\log_{10}$ kill values were converted to an arbitrary activity rating (Corbett, T., et al., Int. J. Pharmacognosy (Suppl.) 33: 102–122 (1995)).

| Duration of Treatment: 5 to 20 days | | |
|---|---|---|
| Antitumor Activity | | Gross $\text{Log}_{10}$ Tumor Cell Kill |
| Highly Active | ++++ | >2.8 |
| | +++ | 2.0–2.8 |
| | ++ | 1.3–1.9 |
| | + | 0.7–1.2 |
| Inactive | − | <0.7 |

Results

Figure 2A:
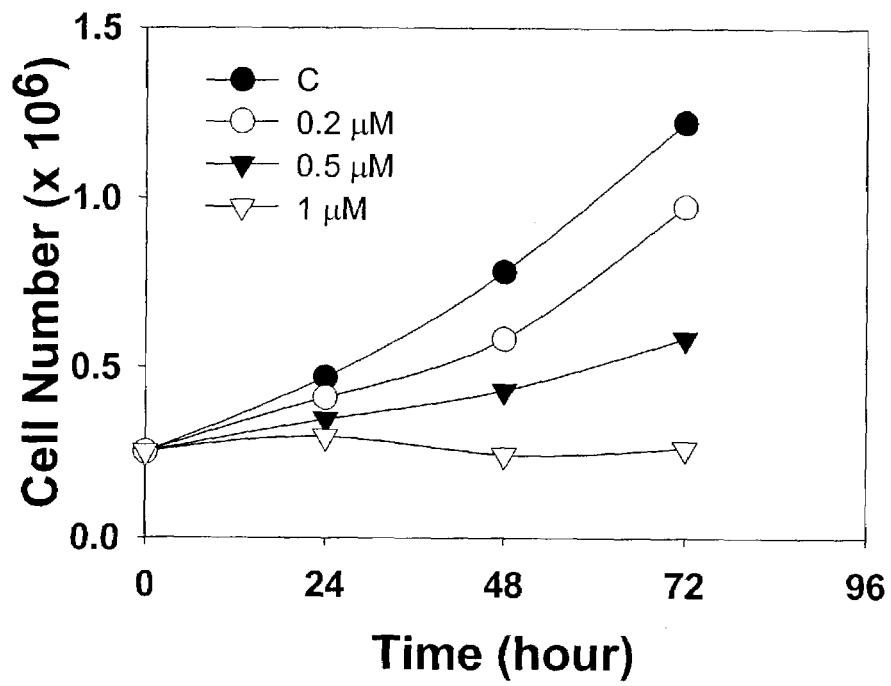
(FIG. 2A) 3-Cl-AHPC inhibition of proliferation.
Figure 2B:
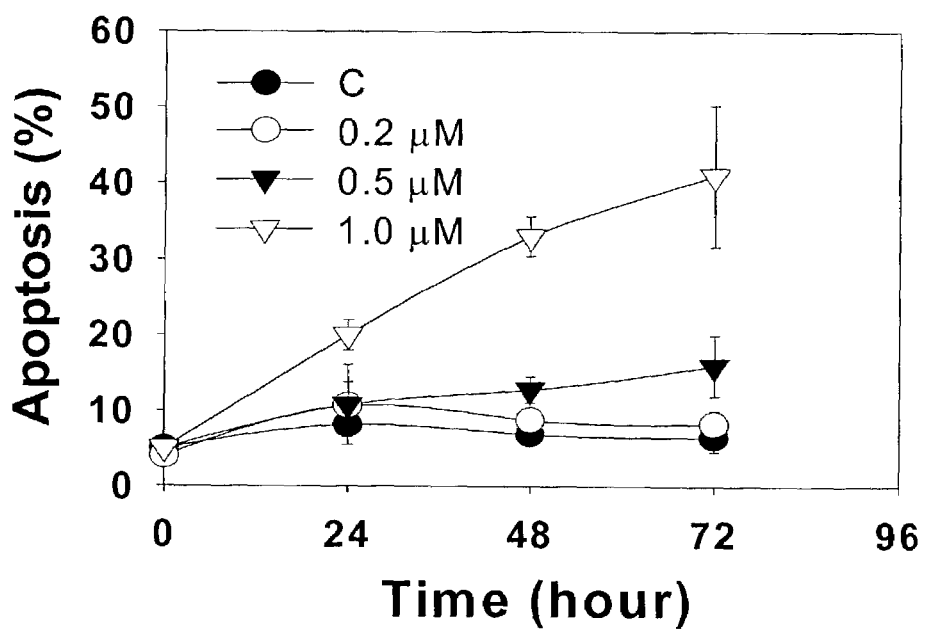
(FIG. 2B) 3-Cl-AHPC induction of apoptosis.
Figure 2C:
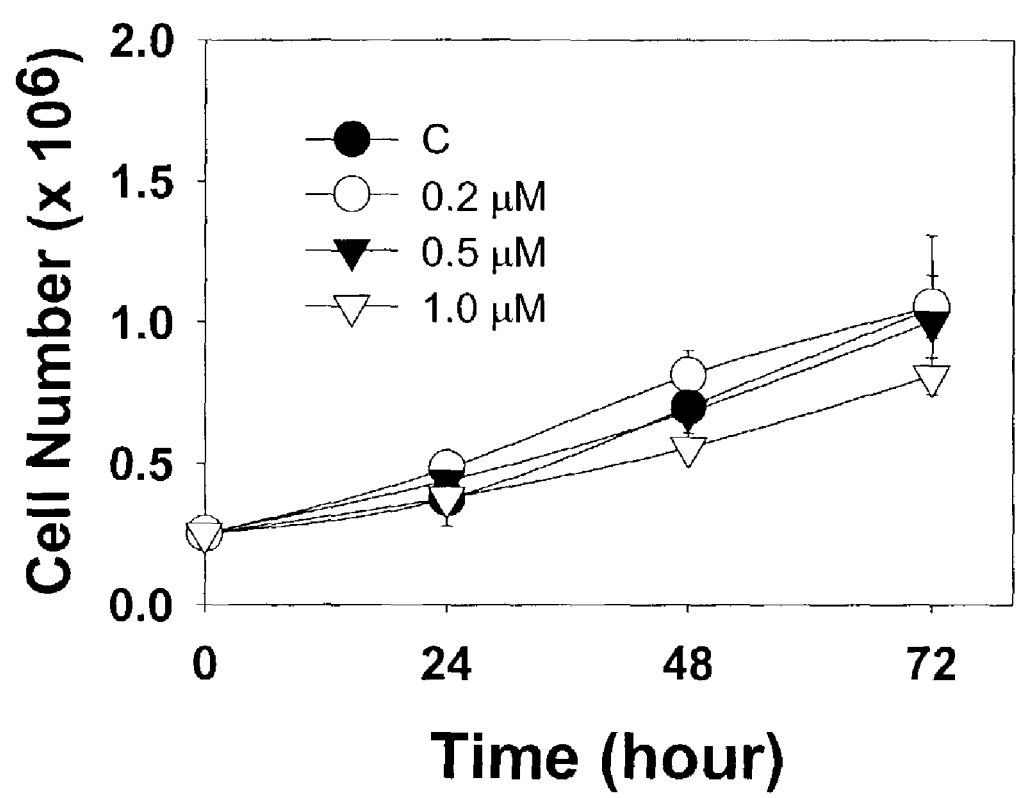
(FIG. 2C) tRA inhibition of M07e proliferation.

3-Cl-AHPC inhibition of leukemic cell growth. The ability of 3-Cl-AHPC to inhibit the growth of human myeloid leukemia cells was assessed using the human acute megakaryocytic leukemia cell line M07e. Exposure of these cells to varying concentrations of 3-Cl-AHPC over time resulted in the progressive increase in the inhibition of proliferation (FIG. 2A). This progressive increase in growth inhibition was accompanied by the onset of apoptosis when 3-Cl-AHPC concentrations of 0.5 and 1.0 μM were used (FIG. 2B); while exposure to 0.2 μM 3-Cl-AHPC resulted in inhibition of growth, no significant increase in apoptosis was noted (FIG. 2B). In contrast, tRA a potent activator of the RARs, did not significantly inhibit M07e proliferation (FIG. 2C) or induce apoptosis in these cells.

Figure 3A:
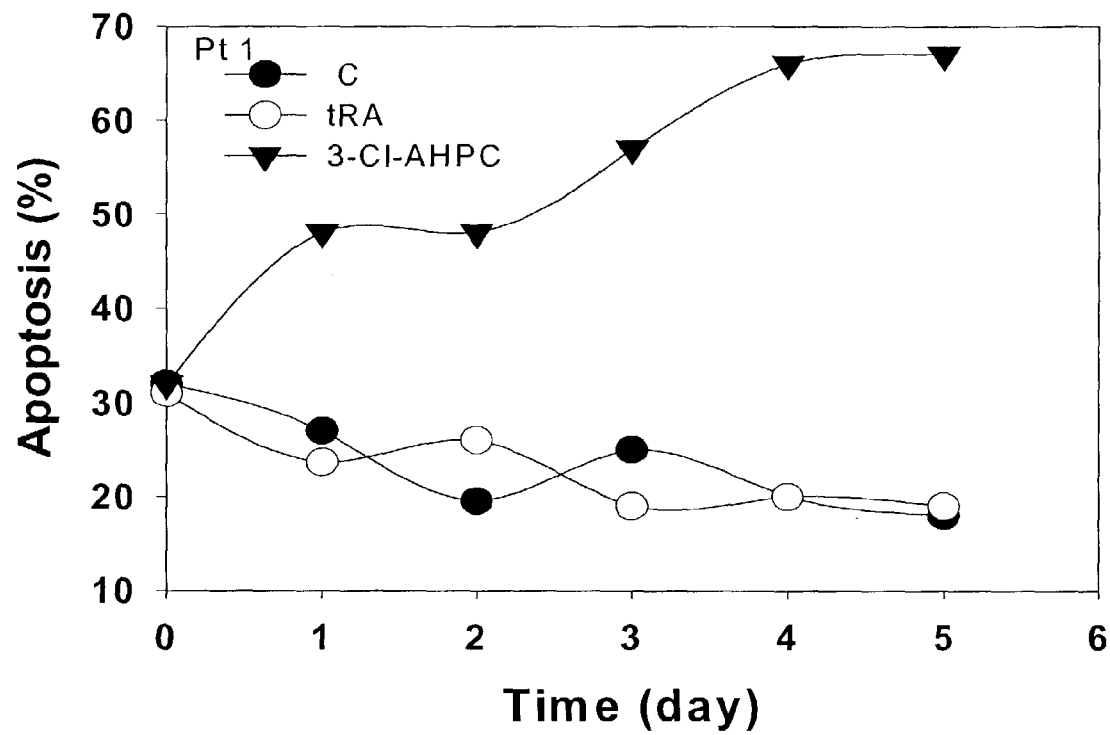
(FIGS. 3A, B, C, D, E, F, G, H, and I) 3-Cl-AHPC or tRA induction of apoptosis.
Figure 3B:
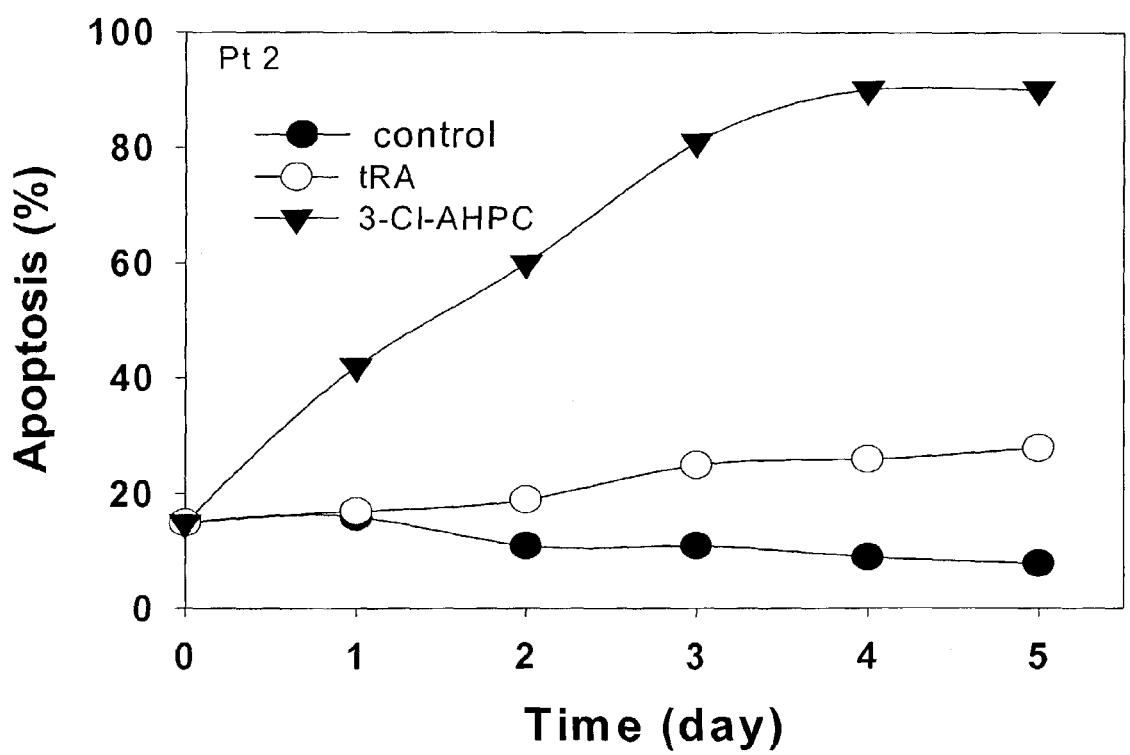
FIG. 3 illustrates the 3-Cl-AHPC and tRA inhibition of growth and induction of apoptosis of leukemic blasts. Leukemia cells obtained from patients were cultured as described herein. AHPN, 3-Cl-AHPC and tRA were added to a final concentration of 1 µM. The cells were harvested at various times and cell numbers and the percent apoptotic cells assessed as described in Materials and Methods.
(FIGS. 3J, K, L, M, and N) 3-Cl-AHPC and tRA inhibition of proliferation.
(FIG. 3O) Patient 1 leukemic cells exposed to various concentrations of 3-Cl-AHPC for up to 120 hours. The results represent the mean of three independent determinations with the variation between the determinations being less than 10% if error flags are not shown.
Figure 3C:
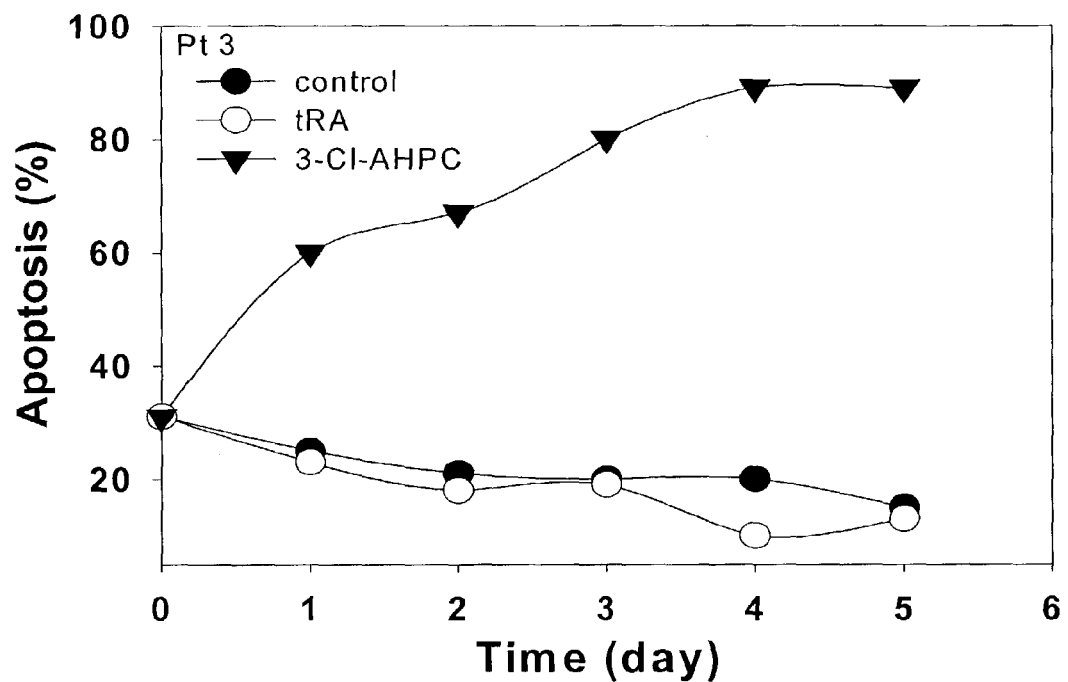
Figure 3D:
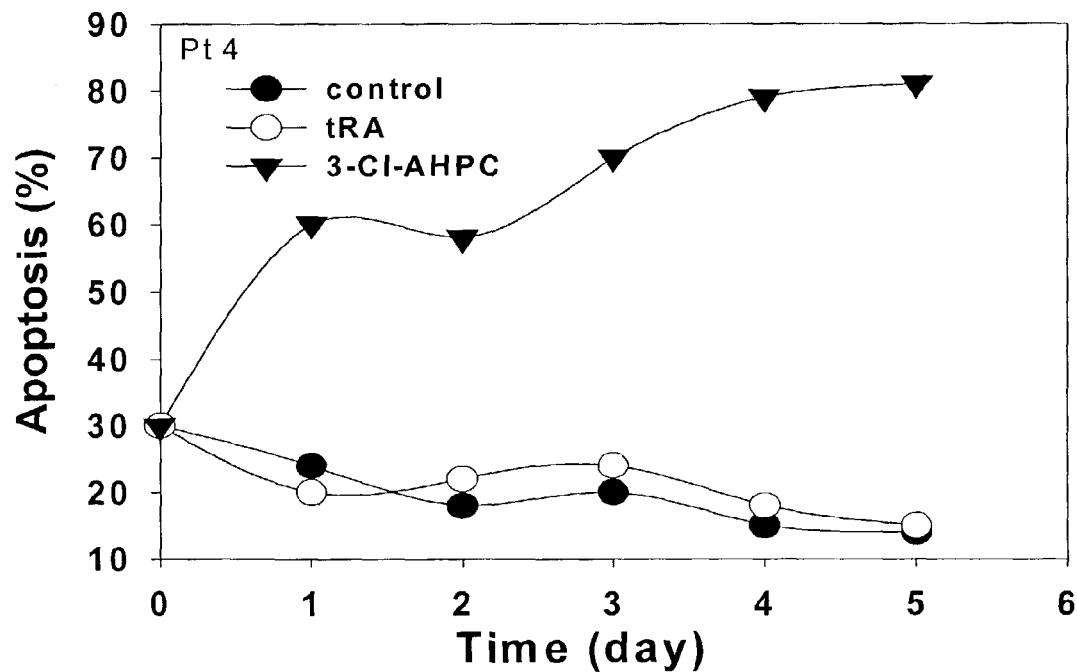
Figure 3E:
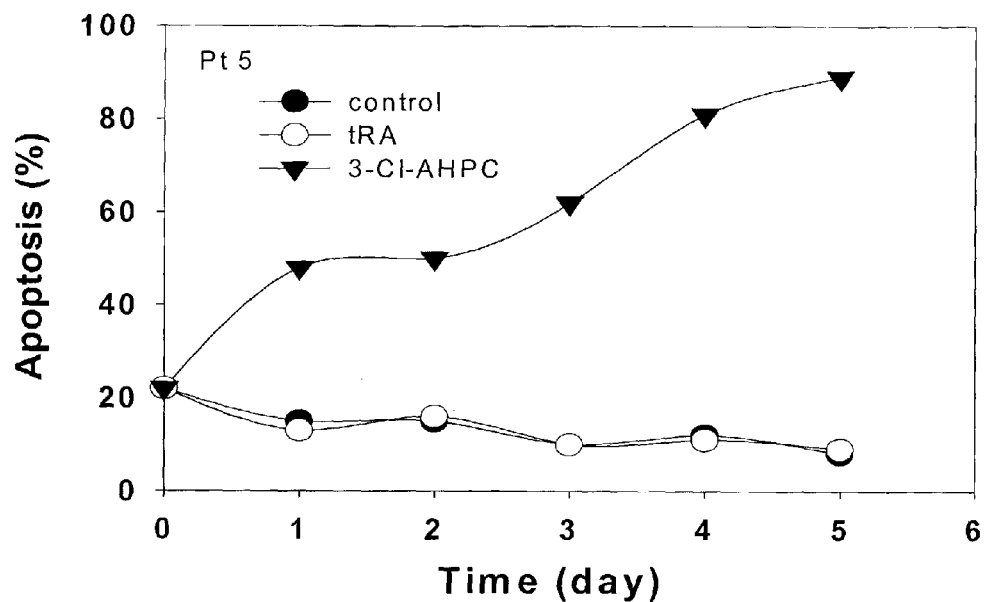
Figure 3F:
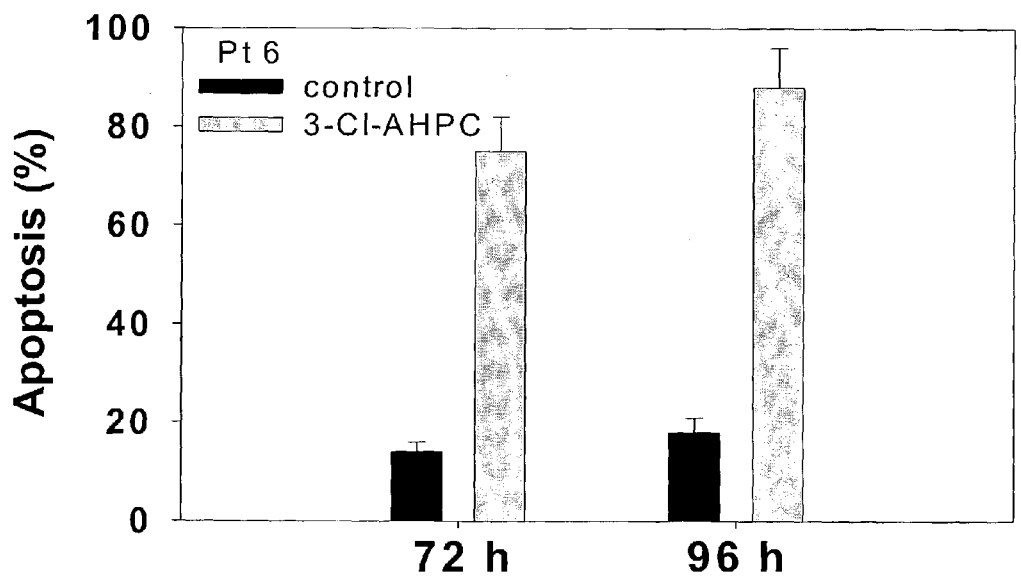
Figure 3G:
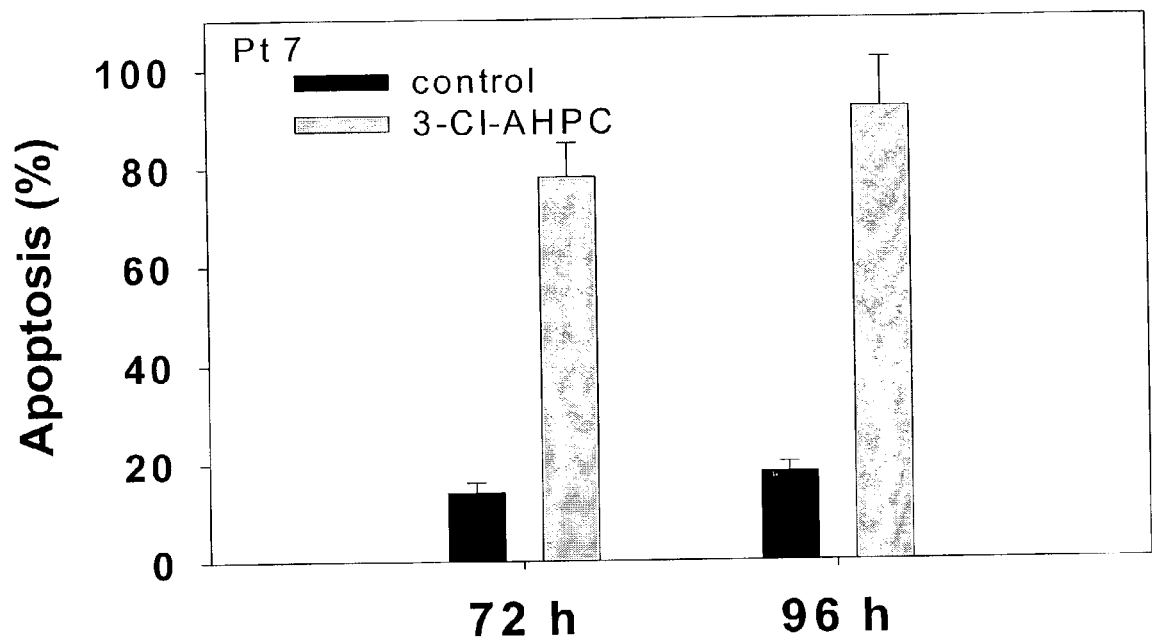
Figure 3H:
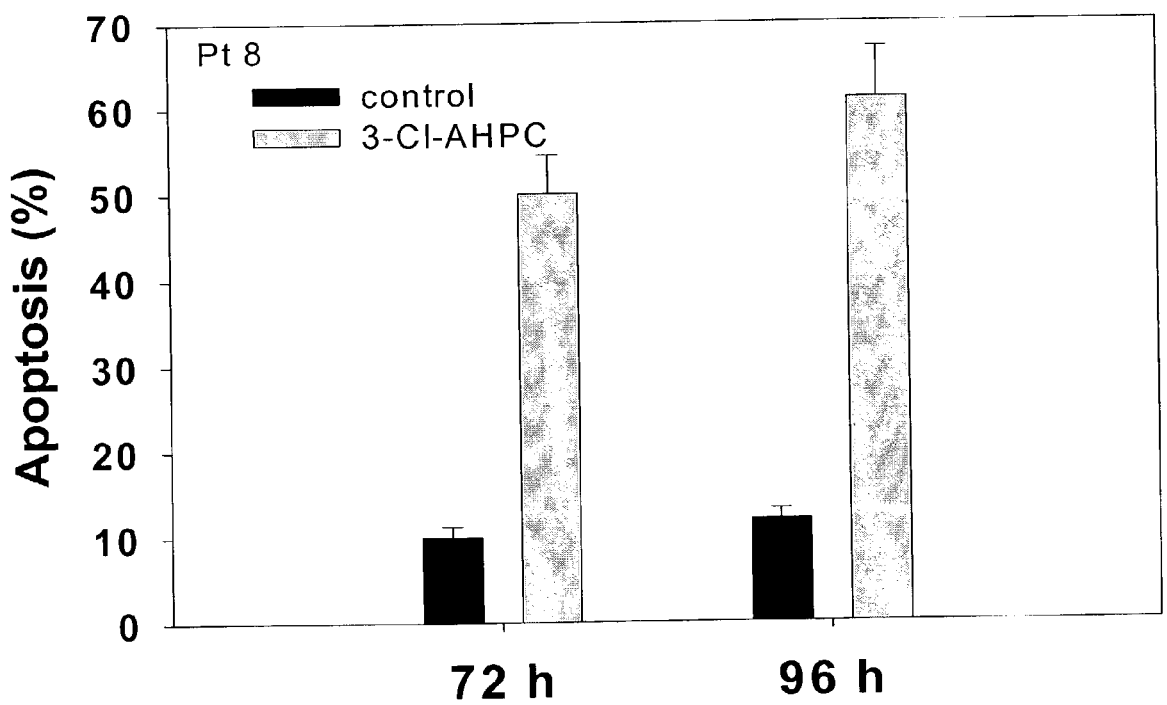
Figure 3I:
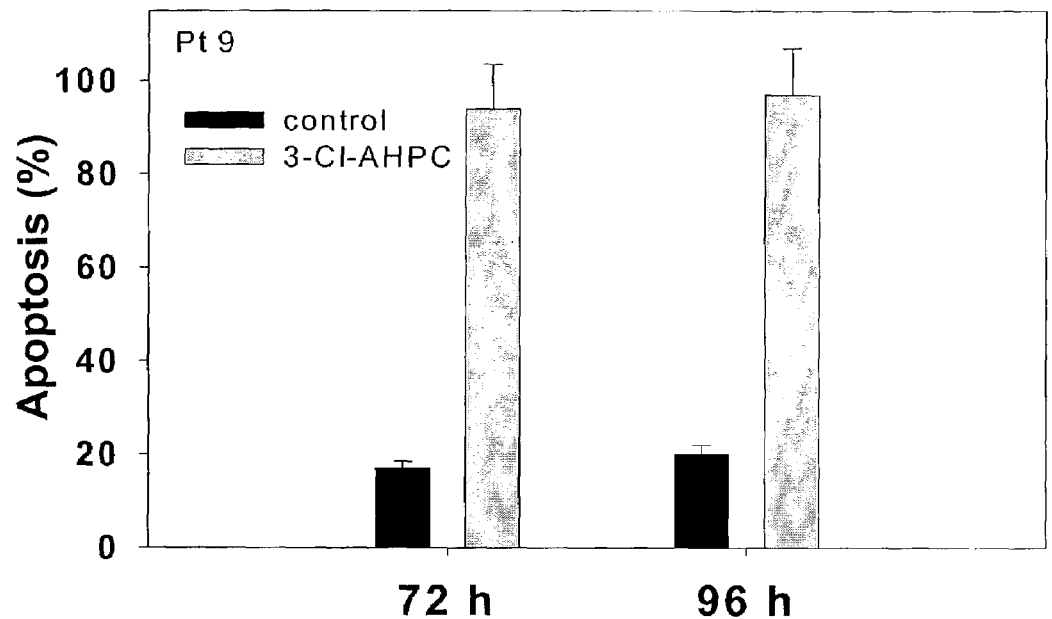
Figure 3J:
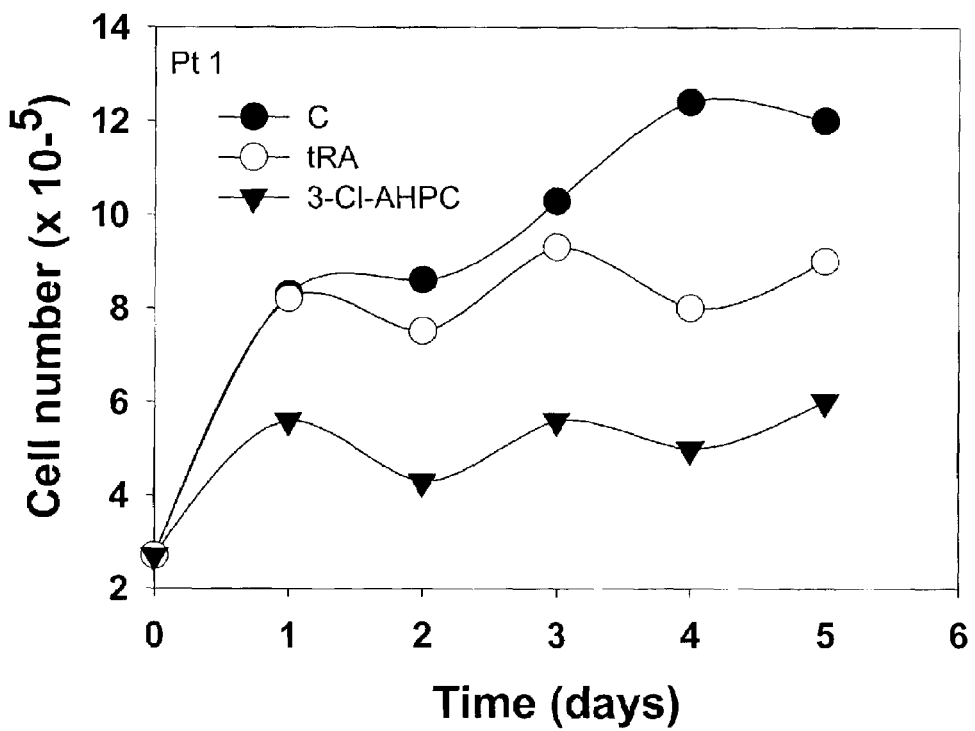
Figure 3K:
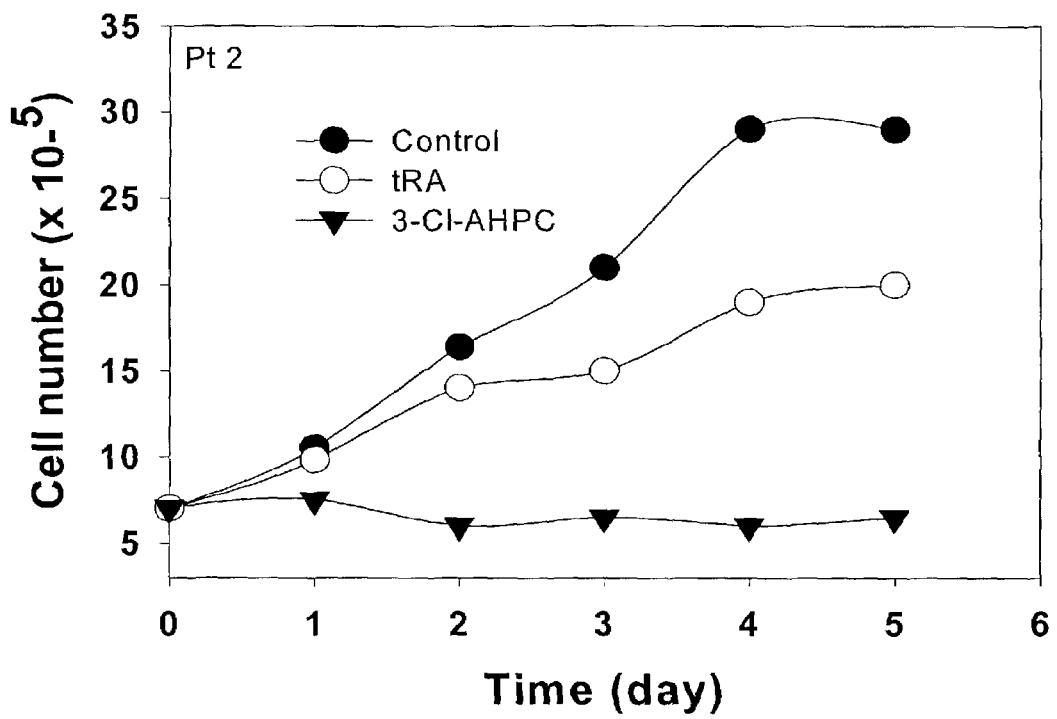
Figure 3L:
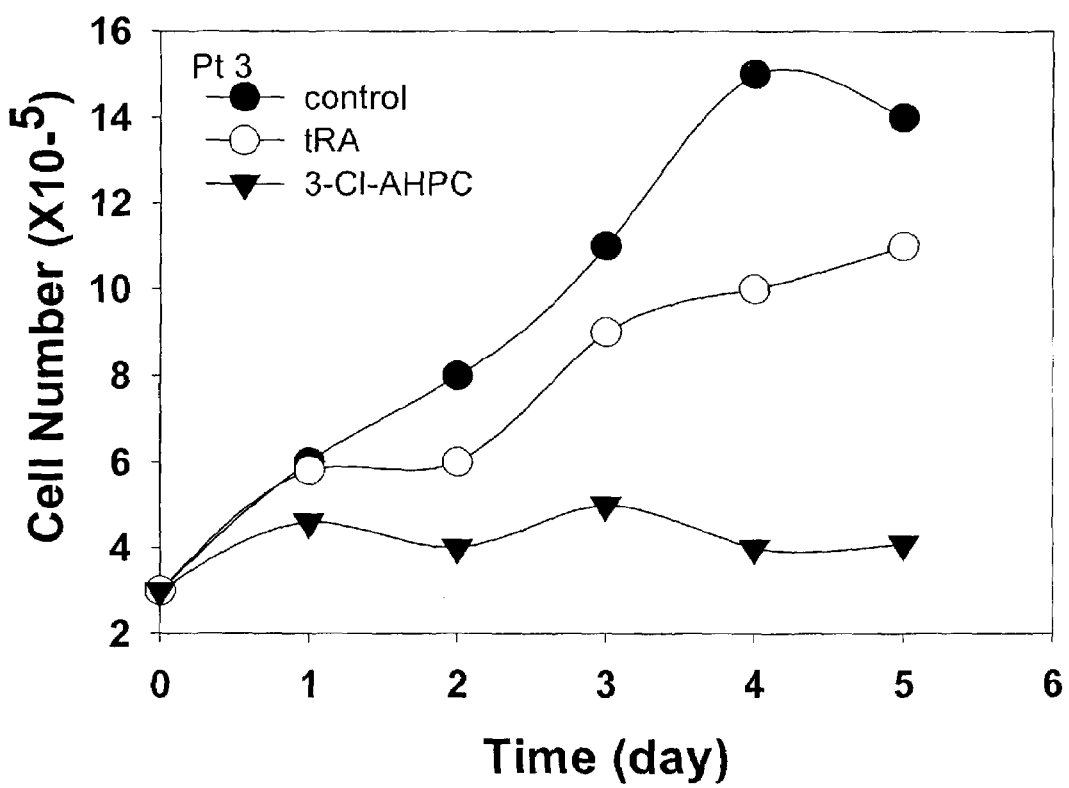
Figure 3M:
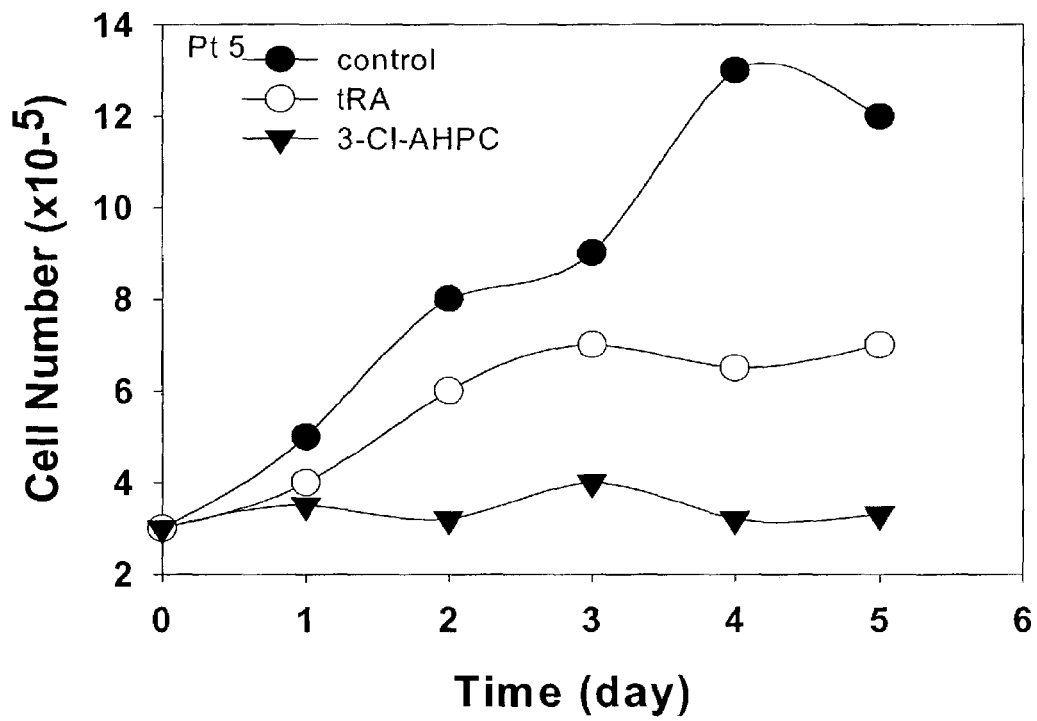
Figure 3N:
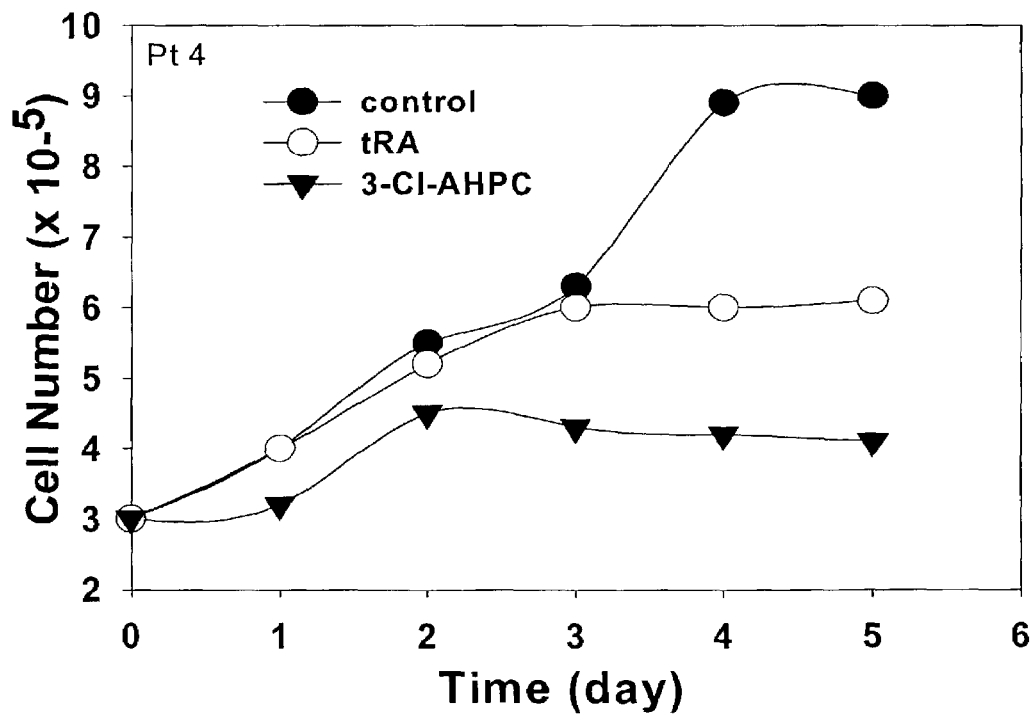
Figure 3O:
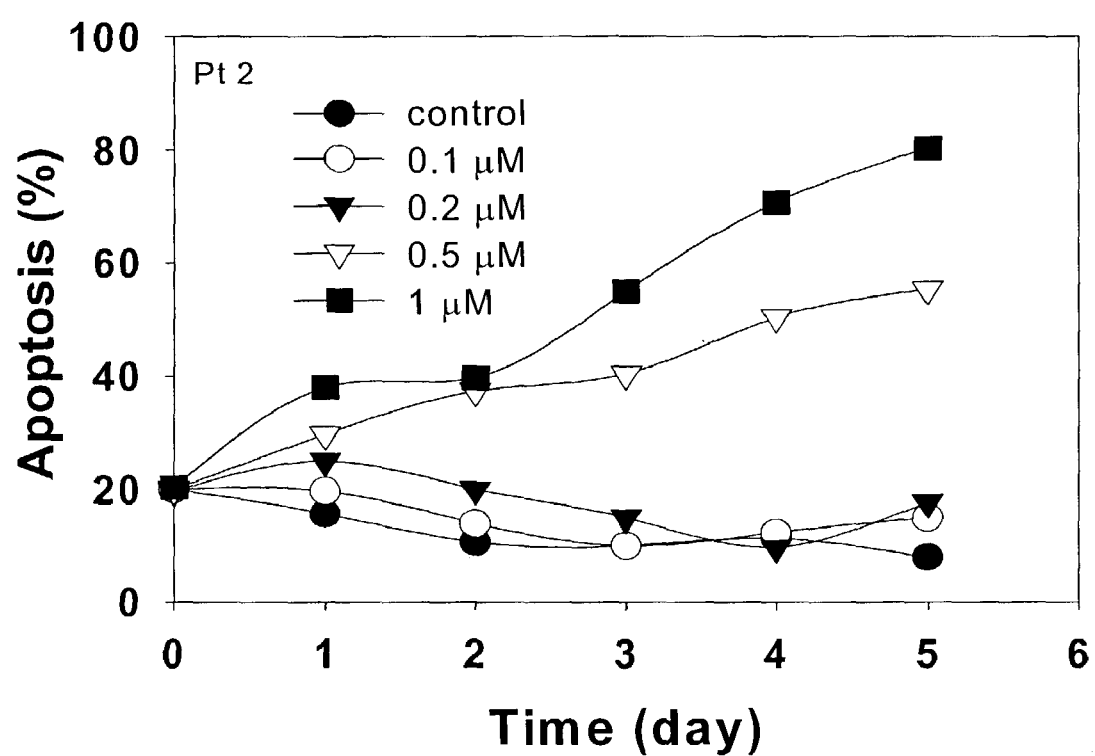
Figure 4A:
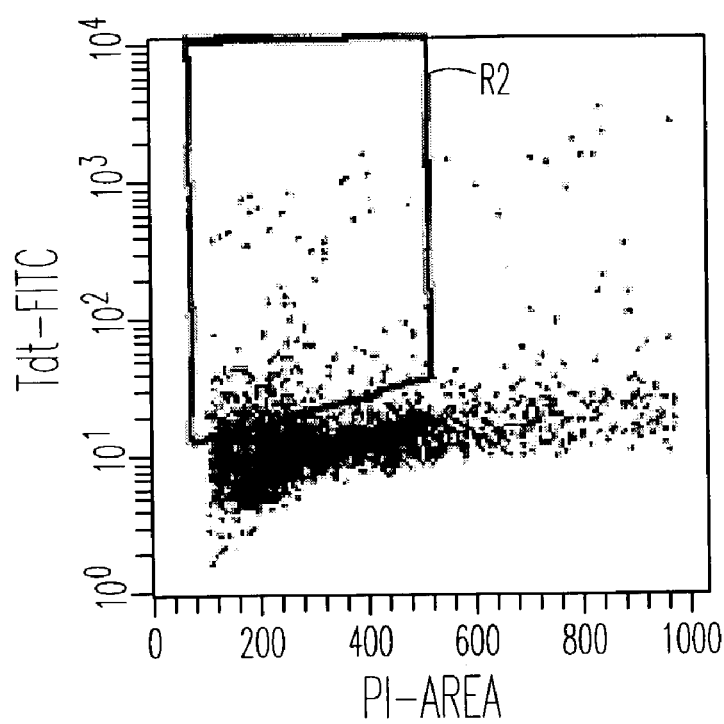
FIG. 4 illustrates 3-Cl-AHPC-mediated apoptosis in leukemic cells assessed by flow cytometry. Leukemia cells (FIGS. 4A and B: Patient 1, and FIGS. 4C and D: Patient 10) were treated with 1 µM 3-Cl-AHPC or vehicle alone for 24 hours, then harvested and the percent apoptotic cells determined using an Apo Direct Kit. The percentage of apoptotic cells was as follows 4A: 4%; 4B: 67%; 4C: 9%; and 4D: 80% in the vehicle-treated cells (FIGS. 4A and C) and 3-Cl-AHPC-treated cells (FIGS. 4B and D).
Figure 4B:
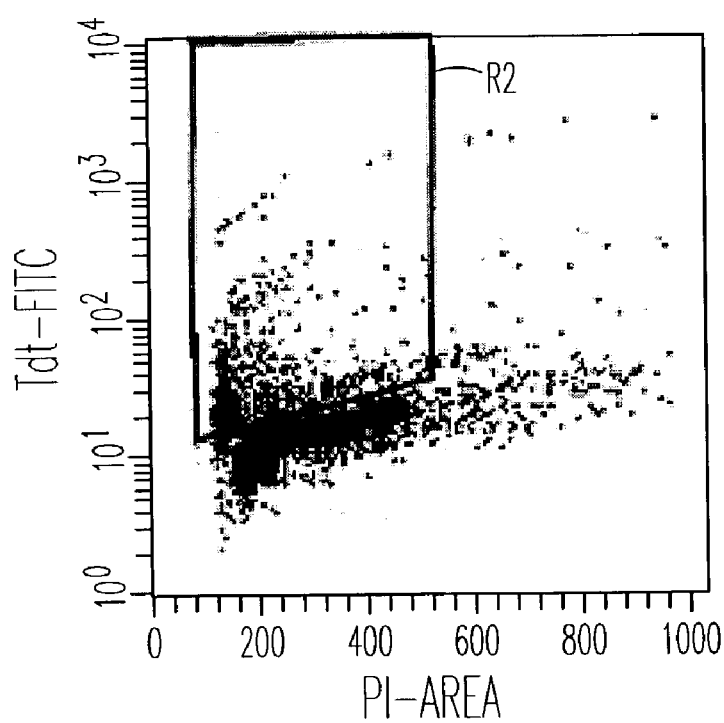
Figure 4C:
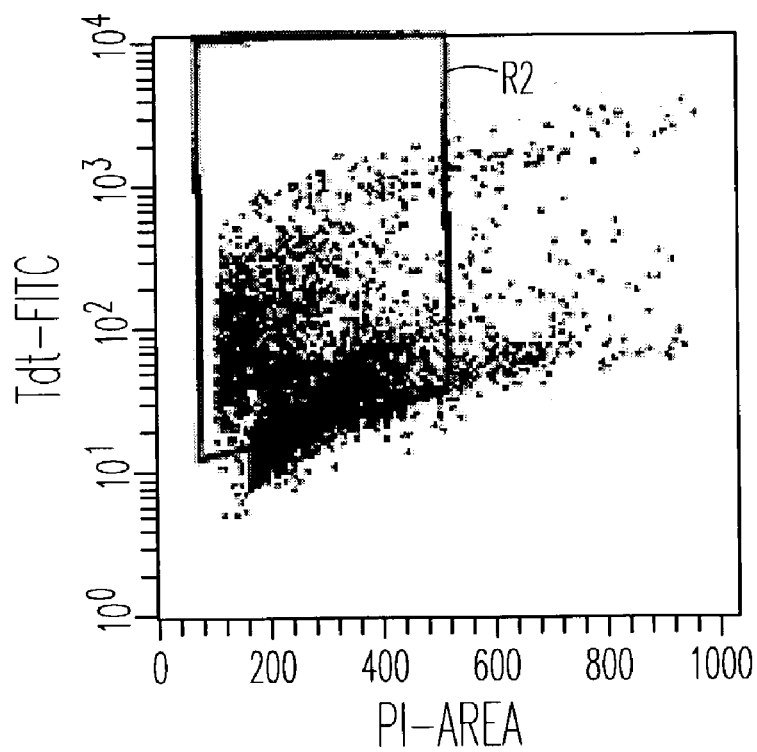
Figure 4D:
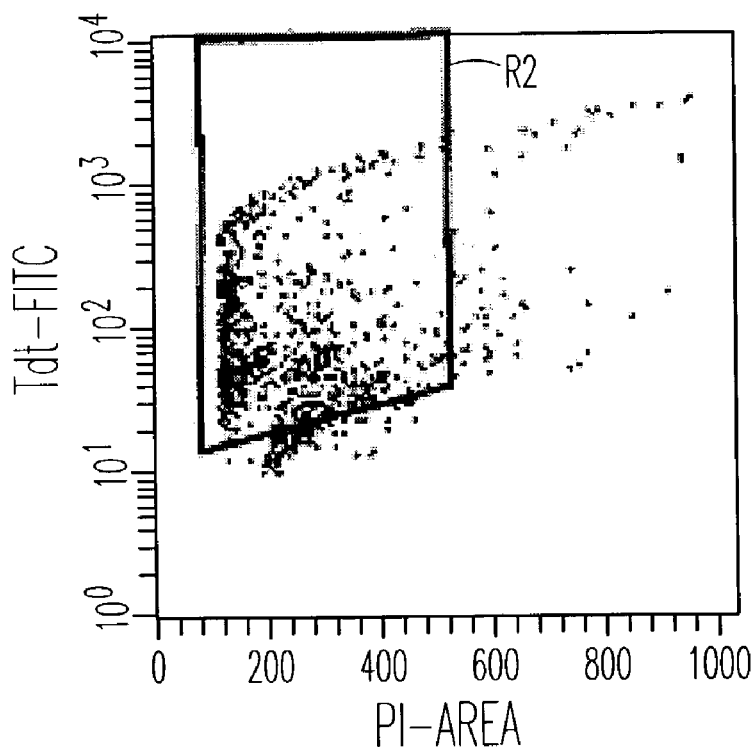

Breitman et al. (Blood, 57, 1000–1004 (1981)) demonstrated that the addition of tRA to primary AML cultures resulted in the differentiation of the APL (M3) cells but had no effect on the other AML subtypes which were classified by the French, American and British (FAB) classification system (Bennett J. B. et al., Ann. Intern. Med. 103: 620–625 (1985)). Therefore, we examined whether 3-Cl-AHPC induced apoptosis in myeloid blasts of differing FAB classifications (Table 1). Exposure of these cells to 1 μM 3-Cl-AHPC resulted in the induction of apoptosis (>80%) in all of 11 primary cultures examined. Representative results are presented in FIGS. 3A and 3B. However, exposure to tRA did not induce apoptosis in these cells (FIGS. 3A, B, C, D, E, F, G, H, and I). The effect of 3-Cl-AHPC on cell proliferation was examined (FIGS. 3J, K, L, M, and N). 3-Cl-AHPC inhibited proliferation of these cells from 60 to 90 percent while tRA inhibited growth by approximately 20 to 30 percent (FIGS. 3J, K, L, M, and N). The ability of 3-Cl-AHPC to induce apoptosis in the patient leukemic blasts was also examined (FIG. 3O). At 0.5 μM 3-Cl-AHPC induced apoptosis in 60% of leukemic blasts whereas minimal apoptosis was noted at 0.2 and 0.1 μM (FIGS. 3J, K, L, M, and N). 3-Cl-AHPC-mediated apoptosis in the myeloid blasts was further assessed by tunnel assay and flow cytometry. Treatment with 1 μM 3-Cl-AHPC for 24 hours resulted in 67% and 80% apoptotic cells in the leukemic cells from patient 1 (FIG. 4B) and patient 10 (FIG. 4D) respectively whereas exposure to vehicle alone resulted in less than 10% apoptosis (FIGS. 4A and C). The percentage apoptotic cells was as follows 4A: 4%; 4B: 67%; 4C: 9%; 4D: 80% in the vehicle-treated cells (FIGS. 4A and C) and 3-Cl-AHPC-treated cells (FIGS. 4B and D).

TABLE 1

Patient Characteristics

| Patient No. | Leukemia Type[1] | Karyotype |
|---|---|---|
| 1 | CML-Blast Crisis | 46, XY, t(9;22) (q34;q11.2) [20] |
| 2 | AML-M1 | No metaphases |
| 3 | AML-M0 | 47, XY, +8[15]/46XY[5] |
| 4 | AML-M2, | 46, XY, del(9)(q21.2q32) [8]/46XY[12] |
| 5 | AML-M4 | 46, Y, add(X)(p22), add(2)(q12), del(3)(q22), add(10)(q21)[20] |
| 6 | AML-M5 | 46, XY, inv (16)(p13 q22) [5]/47, idem, +81 [8] |
| 7 | AML-M4 | 46, XX, inv(16)(p13q22) [9]/46, XX[11] |
| 8 | AML-M1 | 46 XX[20] |
| 9 | AML-M3 | 46, XY, t(15:17) (Q22;21) [20] |
| 10 | M0 | 46, XX[20] |
| 11 | M2 | 56–57, XX, +1, +2, del(4) (q31), del (5)(q13, q33)x2, +6, +9, +11, +13, +14, +15, +22 [CP20] |

[1]Patient leukemia cell types were classified according to the FAB classification system (Corbett, T., et al., Int. J. Pharmacognosy (Suppl.) 33:102–122 (1995)).

3-Cl-AHPC Inhibition of Leukemic Cell Colony Formation

Figure 5A:
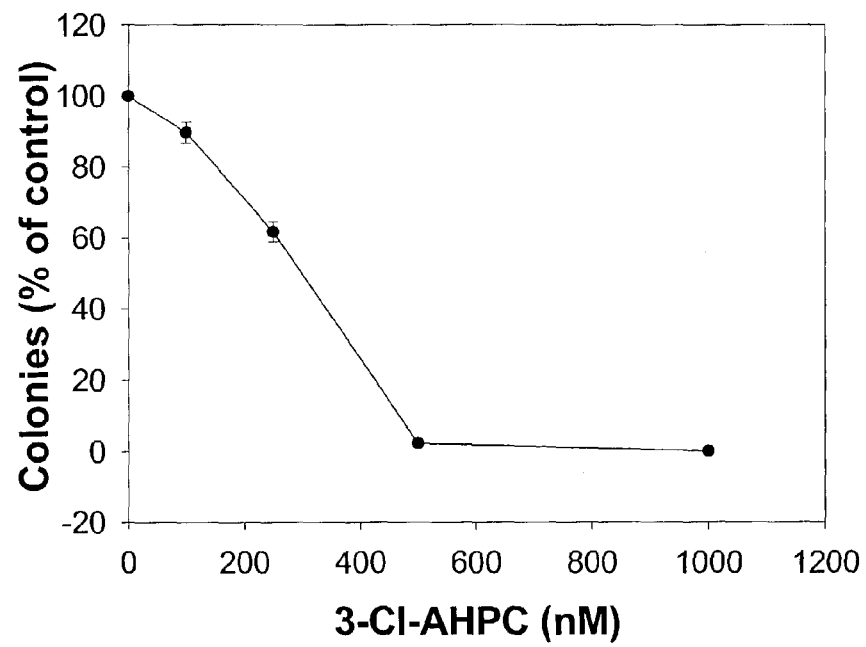
(FIG. 5A) Leukemic cell and (FIG. 5B) CFU-GM colonies were grown in the presence and absence of various concentrations of 3-Cl-AHPC and their formation was assessed as described in Material and Methods.

Leukemic cells obtained from patient 1 were seeded in methylcellulose as described hereinabove, in the presence and absence of of 3-Cl-AHPC. Colony formation was assessed after 14 days of growth (FIG. 5A). 3-Cl-AHPC inhibited leukemia colony formation with an $ED_{50}$ of 375 nM and the complete inhibition of leukemia colony formation at 600 nM (FIG. 4A).

3-Cl-AHPC Inhibition of CFU-GM Colony Formation

Figure 5B:
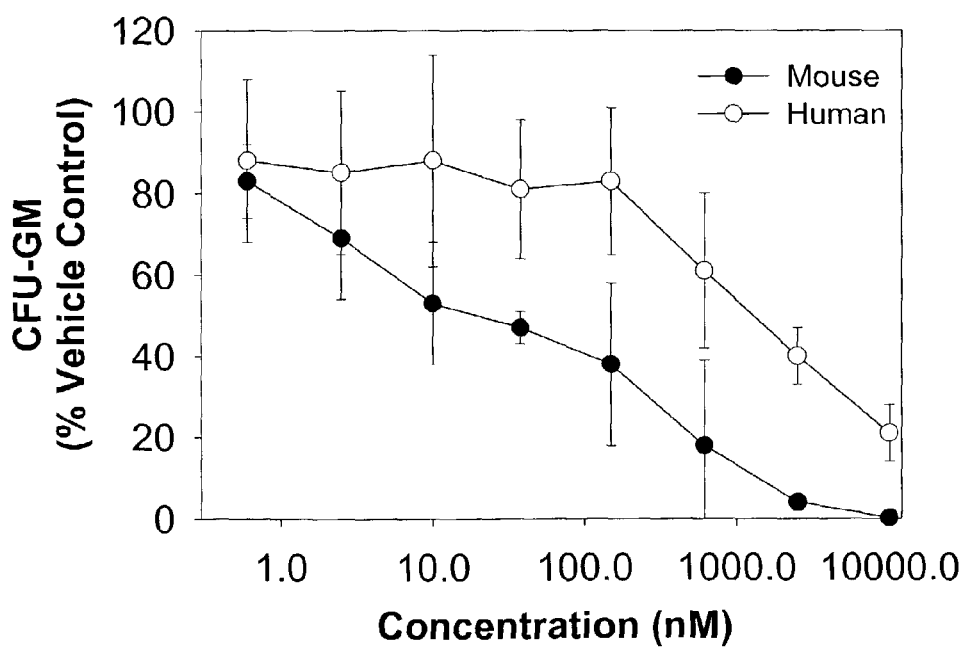
FIG. 5 illustrates the 3-C1-AHPC inhibition of leukemia and CFU-GM colony formation.

The effect of 3-Cl-AHPC on the proliferation of committed marrow stem cells was examined on CFU-GM colony formation. 3-Cl-AHPC concentrations, which completely inhibited leukemic colony formation, only resulted in a 30% inhibition of CFU-GM colony formation (FIG. 5B).

3-Cl-AHPC Induction of Caspase Activity

Figure 6A:
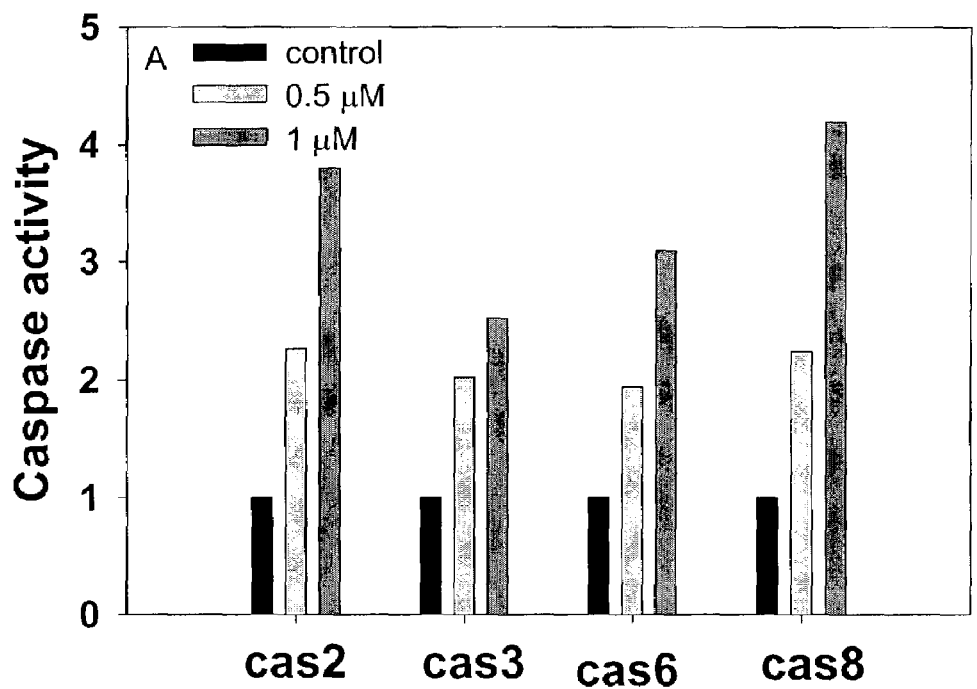
(FIG. 6A) M07e cells treated with vehicle alone or 0.5 µM 3-Cl-AHPC and harvested at various times.

Apoptosis is associated with the activation of specific cysteine proteases referred to as caspases (Woo, M., et al., Genes Devel. 12: 806–819 (1998), and Wolf, B. B., et al., J. Biol. Chem. 274: 20049–20052 (1999)). Treatment of M07e with 1 μM 3-Cl-AHPC resulted in approximately 4-fold increases in the activity of caspase-2 and -8 and 3-fold and 2.5-fold increase in caspase-6 and -3 activities respectively (FIG. 6A). Reduction in the 3-Cl-AHPC concentration to 0.5 μM resulted in lower caspase activation, namely an approximately 2-fold increase in activity of caspases-2, 3, 6 and 8 (FIG. 6A).

Figure 6B:
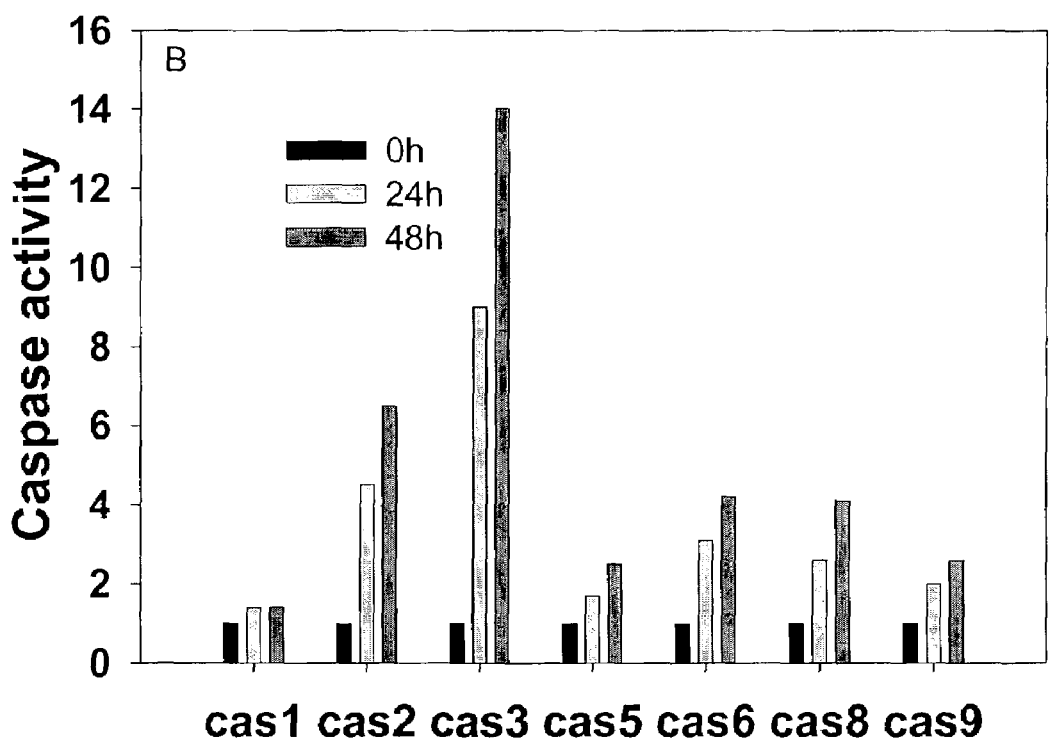
(FIG. 6B) Leukemic cells treated with 1 µM 3-Cl-AHPC and harvested at various times.
Figure 6C:
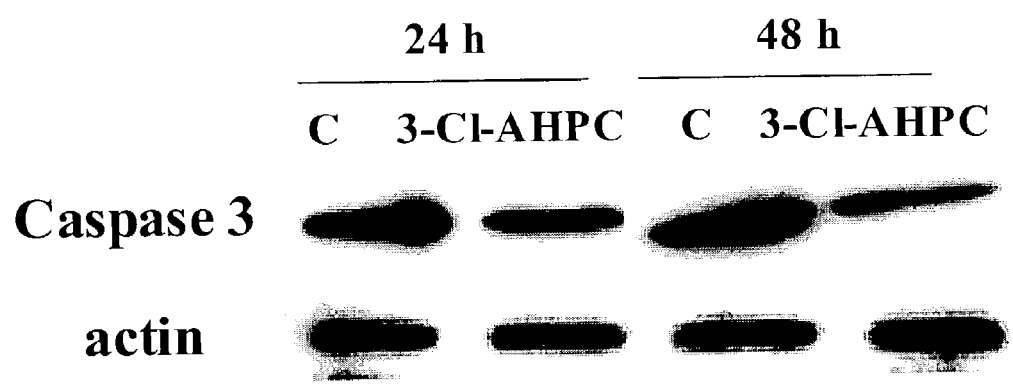
(FIG. 6C) 3-Cl-AHPC activation of caspase-3. Leukemic cells obtained from patient 1 were treated with 1 µM 3-Cl-AHPC or vehicle alone and the cells harvested at 24 or 48 hours. Caspase-3 proenzyme levels were determined utilizing Western blot as described in Materials and Methods. Actin levels were utilized to assess loading. The results are representative of two independent experiments.

When patient leukemic cells were incubated with 1 μM 3-Cl-AHPC, activation of caspases was also noted (FIG. 6B). Caspase-3 had the greatest activation with 8-fold and 14-fold increases at 24 hours and 48 hours, respectively. Activation of caspase-3 was also documented by Western blot that revealed a 3- to 4-fold decrease in inactive caspase-3 proenzyme level following 24 and 48 hours, (FIG. 6C) that coincided with the associated activation of caspase-3 (FIG. 6B). As noted with M07e cells, exposure of the patient leukemic blasts to 3-Cl-AHPC resulted in activation of caspase-2 (6-fold), caspase-6 (4-fold) and caspase-8 (4-fold) (FIG. 6B); two-fold activation of caspase-5 and -9 was also observed (FIG. 6B).

Figure 7A:
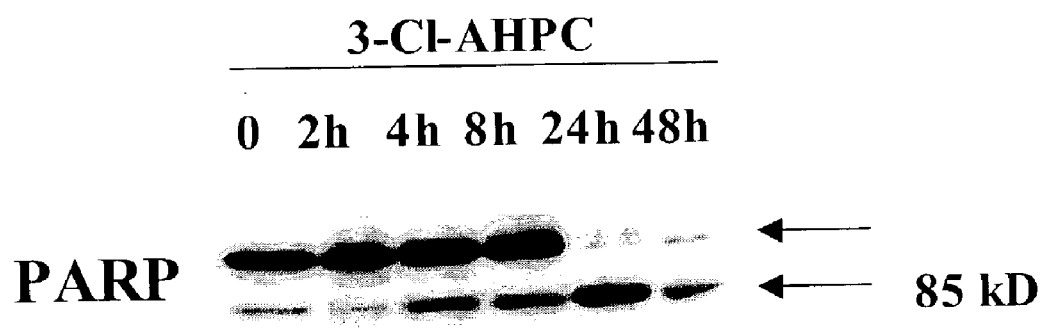
(FIG. 7A) M07e and (FIG. 7B) leukemic cells obtained from patient 10 were exposed to 1 µM 3-Cl-AHPC for up to 24 hours. The cells were then harvested and Western blots performed as described in Materials and Methods.
Figure 7B:
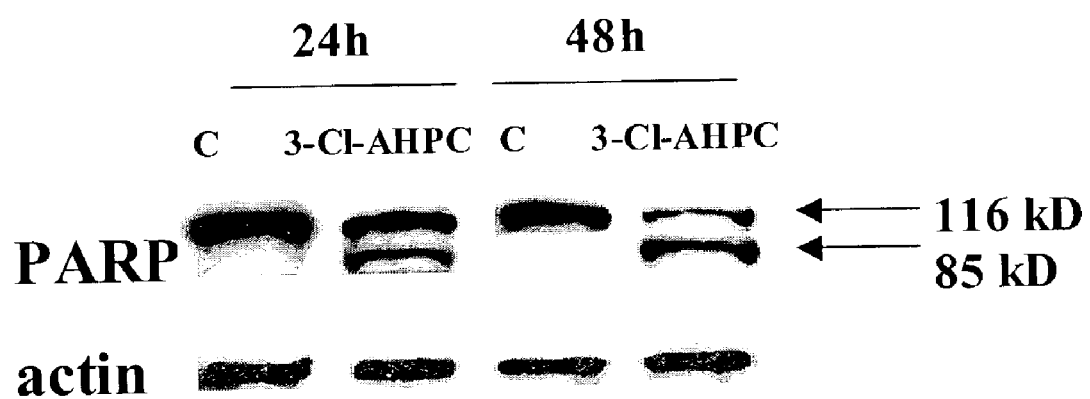
FIG. 7 illustrates PARP cleavage during 3-Cl-AHPC-mediated apoptosis.

Caspase-mediated cleavage of proteins can result in either their activation or inactivation (Widmann, C. et al., J. Biol. Chem., 273: 7141–7147 (1998)). PARP, which plays an important role in both DNA synthesis and repair, is cleaved early in the apoptotic process (Wolf, B. B., et al., J. Biol. Chem., 274: 20049–20052 (1999); Widmann, C. et al., J. Biol. Chem., 273: 7141–7147 (1998); and Vaux, D. L. et al., Proc. Natl. Acad. Sci. USA, 93: 2239–2244 (1996)). 3-Cl- AHPC treatment of both M07e cells and patient leukemic blasts resulted in the rapid cleavage of 116-Kd PARP with the enhanced generation of a 85-kD fragment by 24 hours (FIGS. 7A and B).

Apoptosis is a complex process, which is regulated at multiple levels by numerous mediators (Lazebnik, Y. A. et al., Nature, 371: 346–347 (1994); Hsu, C. A. et al., Blood, 89:4470–4479 (1997); and Aravind, L. et al., Science, 291: 1279–1284 (2001)). The Bcl-2 family can exert either pro-apoptotic or anti-apoptotic effects depending upon which member has a dominant role (Gross, A. et al., Genes Dev. 13:1899–1911 (1999)). Anti-apoptotic Bcl-2 and Mcl-1 are expressed in malignant hematopoietic cells and have been shown to play important roles in cell survival (Thomas, A., et al., Oncogene, 12: 1055–1062 (1996); Hanada, M., et al., Blood, 82:1820–1828 (1993); and Zhou, P., et al., Blood, 89: 630–643 (1997)).

Figure 8A:
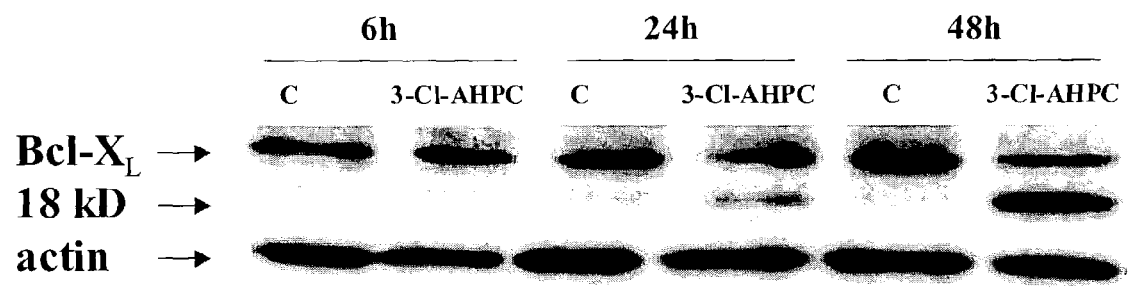
FIG. 8 illustrates the 3-Cl-AHPC-mediated Bcl-$X_L$ cleavage. Leukemic cells obtained from patient 11 were (FIG. 8A) incubated in the presence and absence of 1 µM 3-Cl-AHPC for various times or (FIG. 8B) in the presence of 1 µM 3-Cl-AHPC and in the presence and absence of 50 µM caspase inhibitor zVAD-fmk for 24 hours. Western blots were performed utilizing anti-Bcl-$X_L$ antibody as described in Methods. Actin levels were utilized to assess loading.
Figure 8B:
Figure 9A:
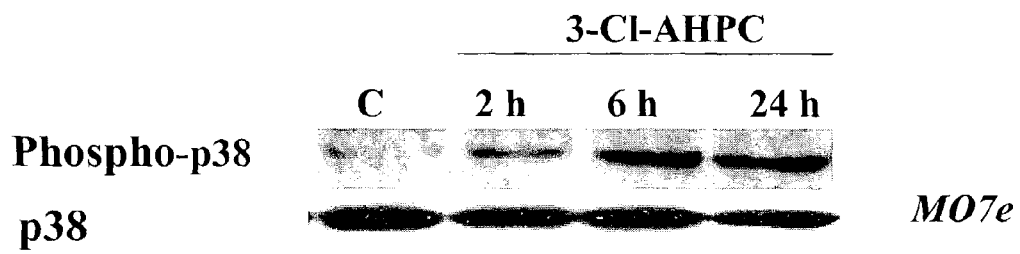
(FIGS. 9A, B, and C) Phospho-p38.
Figure 9B:
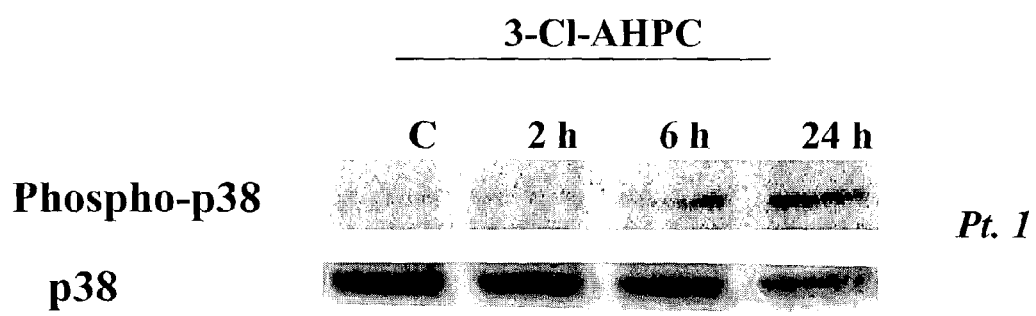
FIG. 9 illustrates 3-Cl-AHPC activation of p38, ERK and JNK. M07e and leukemic cells were exposed to 1 µM 3-Cl-AHPC, 1 µM tRA or vehicle alone in the presence and absence of the capsase inhibitor 50 µM ZVAD-fmk. Phospho-p38, phospho-ERK and phospho-JNK levels were assessed using Western blots as described in Materials and Methods.
(FIGS. 9D, E, and F) Phospho-ERK.
(FIGS. 9G, H, I, and J) Phospho-JNK.
Figure 9C:
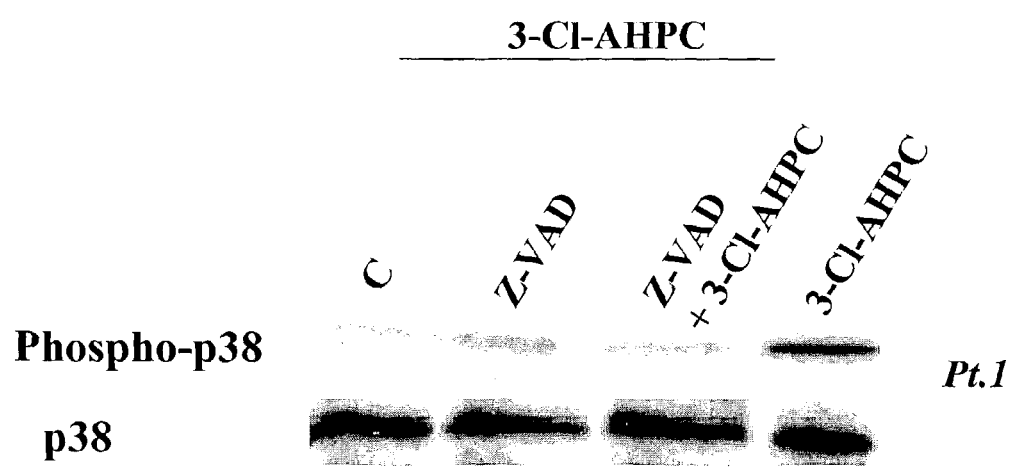
Figure 9D:
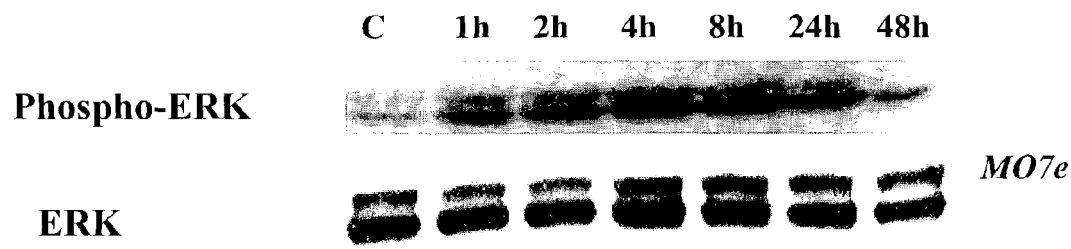
Figure 9E:
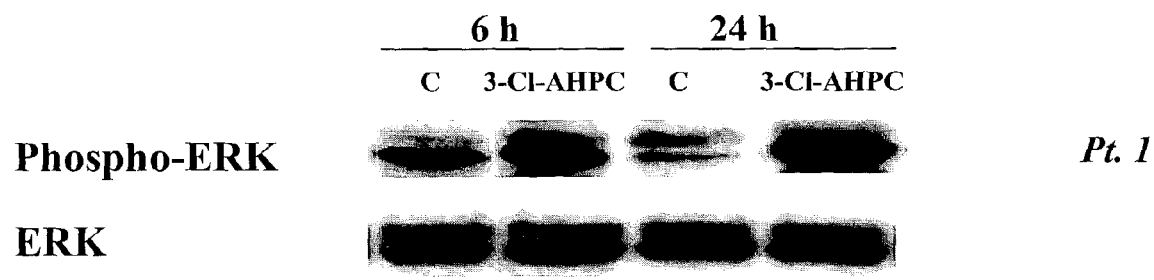
Figure 9F:
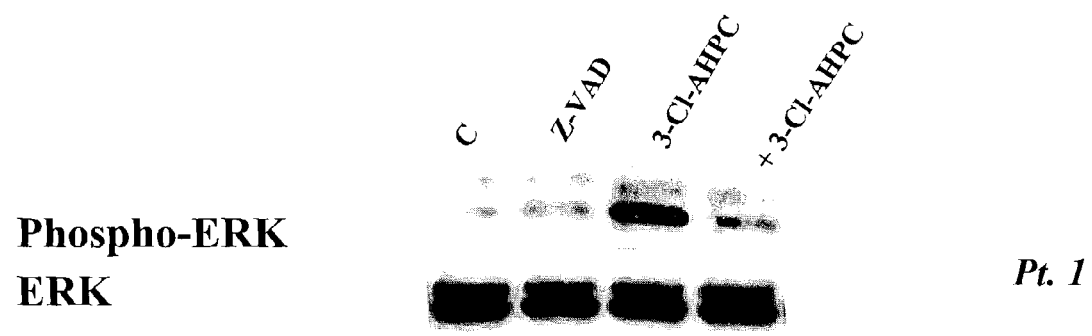
Figure 9G:
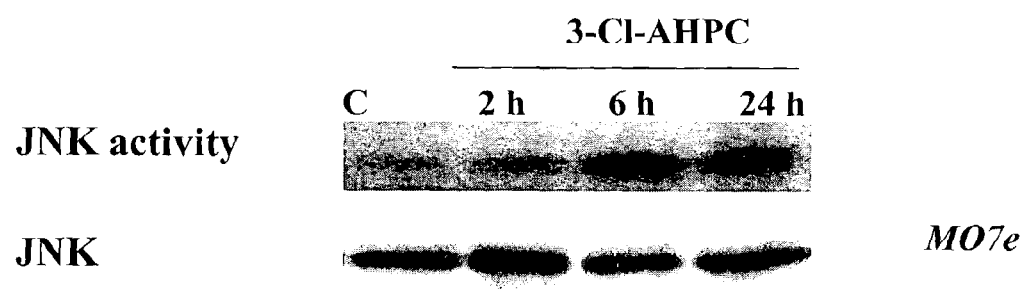
Figure 9H:
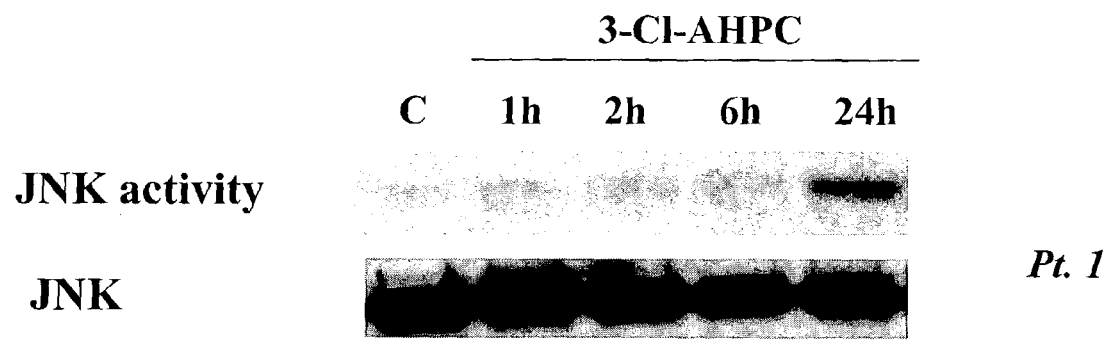
Figure 9I:
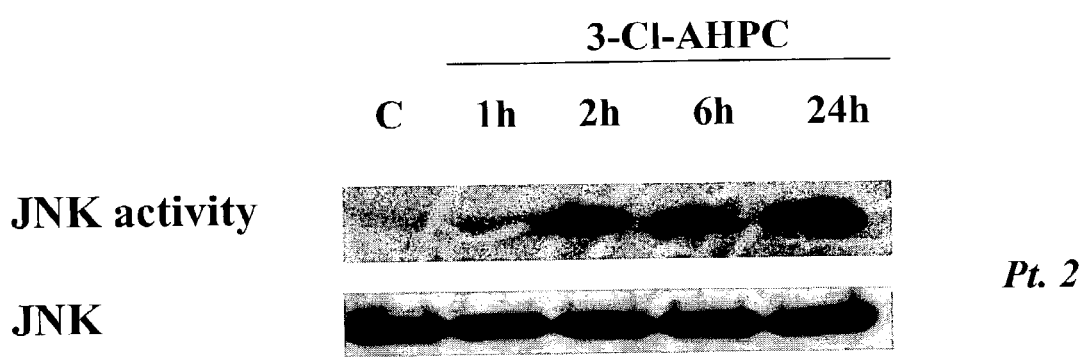
Figure 9J:
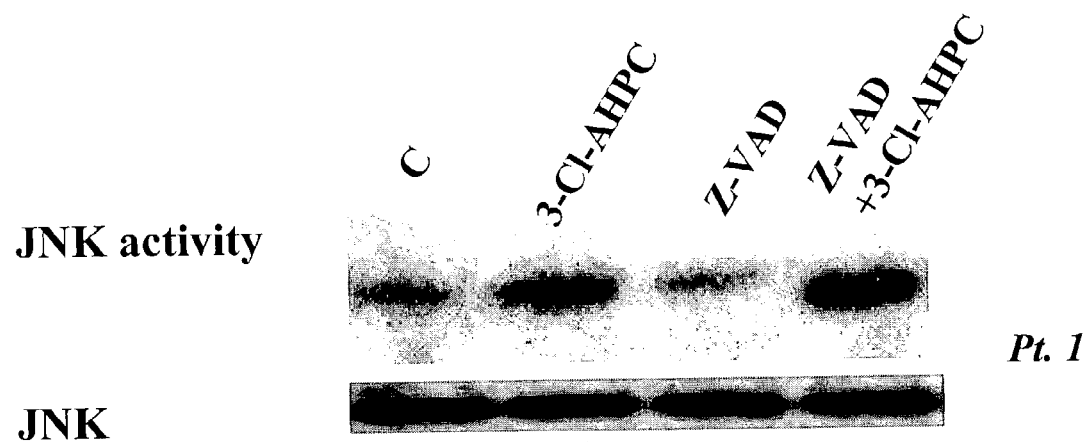

While both patient leukemic cells and M07e cells express Bcl-2 and Mcl-1, there was no modulation of their expression during 3-Cl-AHPC-mediated apoptosis. Bcl-X is a genetic homolog of Bcl-2. The Bcl-X gene encodes for two proteins termed $Bcl-X_L$ and $Bcl-X_S$ through alternative splicing (See Boise, L. H. et al., Cell, 74: 597–608 (1993)). While $Bcl-X_S$ is a potent inducer of apoptosis, $Bcl-X_L$ inhibits apoptotosis (Boise, L. H. et al., Cell, 74: 597–608 (1993)). Western blots of M07e cells and patient leukemic cells demonstrated expression of $Bcl-X_L$ but not $Bcl-X_S$ (FIG. 8). Treatment of the cells with 1 μM 3-Cl-AHPC resulted in the cleavage of $Bcl-X_L$ to a 18-kD product (FIG. 8A). Previous studies found that cleavage of $Bcl-X_L$ and the subsequent generation of the 18-kD product was the result of caspase-3 activation (Fujita, N. et al., Oncogene 17: 1293–1307 (1998)). Inhibition of caspase-3 activity by the caspase-3 inhibitor ZVAD-fmk inhibited $Bcl-X_L$ cleavage (FIG. 8B).

Activation of MAPK Pathways During 3-Cl-AHPC-Mediated Apoptosis

Figure 10A:
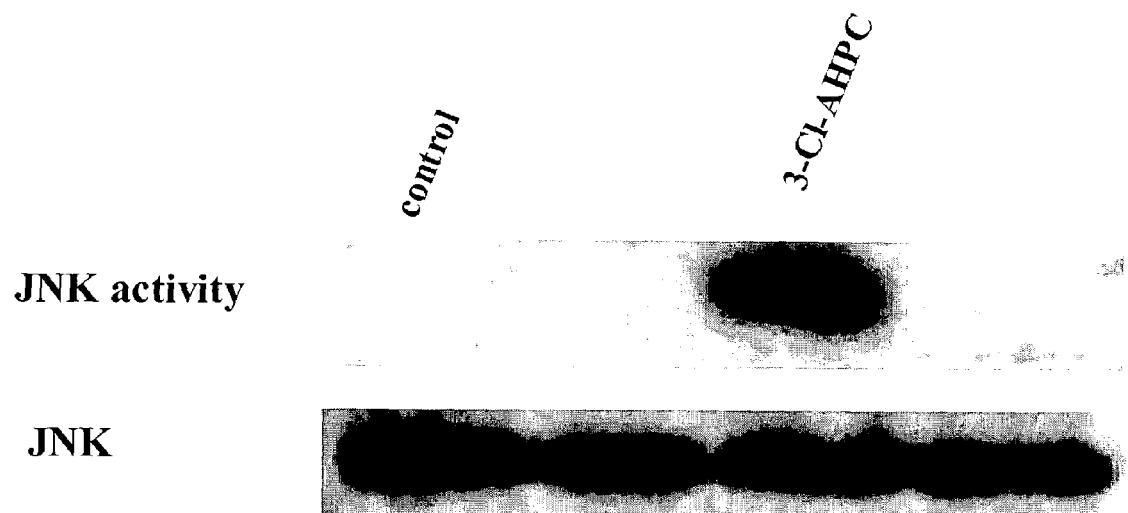
FIG. 10A illustrates the inhibition of 3-Cl-AHPC-mediated JNK activation. Leukemic (patient 1) were exposed to 1 µM 3-Cl-AHPC, 20 µM, PD 169316 or the combination and (FIG. 10A) JNK activation.
Figure 10B:
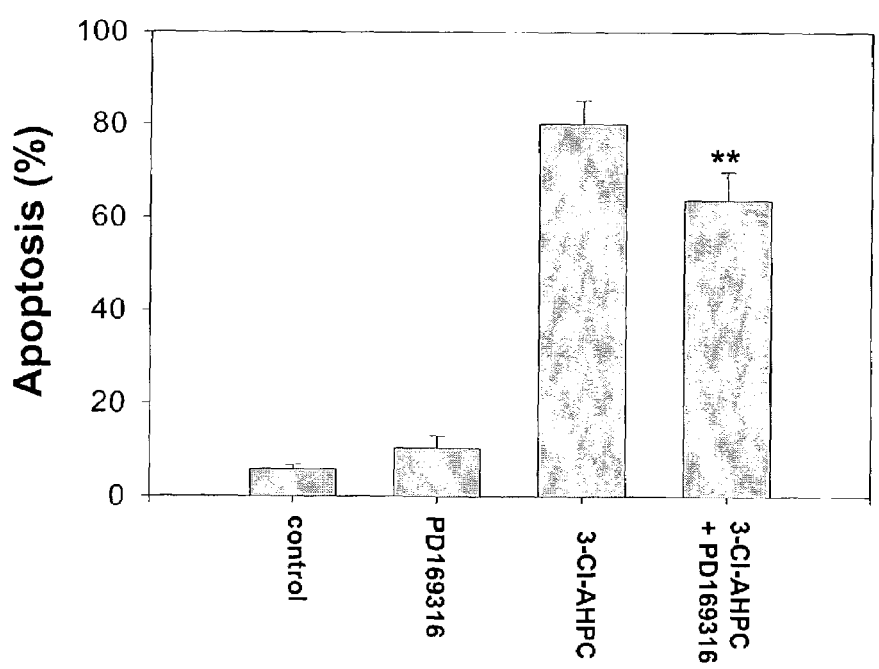
FIG. 10B illustrates the levels of apoptotic cells that were assessed as described in the Methods. **Significantly less apoptosis than that mediated by 3-Cl-AHPC alone (p<0.01). Error bars represent standard deviations.

Activation of the mitogen-activated protein kinase (MAPK) pathways is associated with the induction of apoptosis in many cell types (Franklin, R. A. et al., Leukemia, 14: 2019–2034 (2000); and Jarpe, M. B. et al., Oncogene, 17: 1475–1482 (1998)). ERK, p38, and JNK activations have been observed but their roles in apoptosis remains unclear (Wang, X. et al., J. Biol. Chem., 275: 39435–39443 (2000); Tournier, C. et al., Science, 288: 870–874 (2000); and Davis, R. J., Cell, 103: 239–252 (2000)). Treatment of the HL-60R human leukemia cell line with AHPN resulted in p38 and JNK activation (Hsu, C. A. et al., Blood, 89:4470–4479 (1997)). Therefore, whether 3-Cl-AHPC activated any or all of these three MAPK pathways in the M07e cells and the patient leukemic cells and their roles in 3-Cl-AHPC-mediated apoptosis were examined. 3-Cl-AHPC treatment resulted in activation of ERK, p38 and JNK kinases (FIGS. 9A–J). Activation of p38 and ERK required caspase activation as evidenced by the ability of the pan-caspase inhibitor ZVAD-fmk to prevent their activation by 3-Cl-AHPC (FIGS. 10A, and B). JNK activation was not inhibited by ZVAD-fmk suggesting that its activation was caspase independent. The potential role of these kinases in 3-Cl-AHPC-mediated apoptosis was investigated. Inhibition of 3-Cl-AHPC-mediated p38 and ERK activation by the p38 inhibitor PD169316 and ERK inhibitor PD98059, respectively, did not inhibit or enhance 3-Cl-AHPC-mediated apoptosis of either M07e or patient leukemia cells. However, high of PD169316 ($\geq 20$ μM), which inhibited both p38 and JNK activation, inhibited 3-Cl-AHPC-mediated apoptosis by 20 percent to suggest that JNK activation may be required for optimal 3-Cl-AHPC-mediated apoptosis (FIGS. 10A and B).

Murine AML 1498 cells intravenously implanted in C57BI/6 mice were utilized to evaluate 3-Cl-AHPC inhibition of the in vivo growth of AML cells. The murine AML 1498/C57BI6 syngeneic model has been validated for assessing the activity of therapeutic potential against AML (Bradner, W. T. et al., Cancer Res. 26: 375–390 (1966)). Treatment of mice with 3-Cl-AHPC at total dosage of 140 or 115 mg resulted in a 3.3 log cell kill with a doubling in the survival duration (Table 2). Treating mice with a 140 mg/kg total dose of 3-Cl-AHPC over a period of four days resulted in a 17% weight loss and no animal deaths (Table 2), whereas the equally effective 115-mg total dose led to a weight loss of 6%. The results are summarized in Table 2.

TABLE 2

3-Cl-AHPC treatment of AML bearing mice

| Treatment | Cells Implanted | Schedule | Total Dose mg/kg | Mean Body Wt. Loss (g/mouse) | Body Wt. Loss (%) | Median Day of Tumor Death (range) | ILS (%) | Log Cell Kill |
|---|---|---|---|---|---|---|---|---|
| None | $5 \times 10^6$ | | | +0.0 | +0.0 | 6 (6,6,6,6,8) | | |
| None | $5 \times 10^4$ | | | +1.2 | +5.7 | 9 (9,9,9,9,9) | | |
| None | $5 \times 10^2$ | | | +0.0 | +0.0 | 12 (12,12,12,12,12) | | |
| 3-Cl-AHPC | $5 \times 10^6$ | qd 1–4 | 140 | −3.6 | −17.3 | 11 (10,11,11,11,11) | 83 | 3.3 |
| 3-Cl-AHPC | $5 \times 10^6$ | qd 1–5 | 115 | −1.2 | −5.8 | 11 (10,10,11,11,11) | 83 | 3.3 |
| 3-Cl-AHPC | $5 \times 10^6$ | qd 1–5 | 80 | +0.0 | +0.0 | 9 (8,9,9,9,10) | 50 | 2.0 | a) Percent Increase in Lifespan (% ILS) for leukemic mice $(T - C)/C \times 100$; in which C = the median day of death of the control group and T = The median day of death of the treated group.

AML cells from patients with a variety of FAB subtypes displayed sensitivity to 3-Cl-AHPC. Concentrations of 0.2 μM were required for 3-Cl-AHPC to inhibit growth of M07e cells while 0.5 μM were required to induce apoptosis. Similarly, 0.5 μM 3-Cl-AHPC was required to induce apoptosis in patient leukemic cells. In addition, 3-Cl-AHPC inhibited leukemia colony formation with a $IC_{50}$ of 375 nM. Complete inhibition of colony formation occurred at 600 nM. The ability of 3-Cl-AHPC to inhibit normal hematopoietic colony-forming cells from the neutrophil/monocyte linage (CFU-GM) in human and mouse bone marrow was also assessed. 3-Cl-AHPC had 30-fold greater toxicity to mouse than human CFU-GM. The $IC_{90}$ values in the mouse ranged from 315–794 nM, whereas the human tolerated much higher levels of 3-Cl-AHPC ($IC_{90} > 15$ μM).

Exposure of M07e and patient leukemic cells to 3-Cl-AHPC resulted in apoptosis, as documented by a number of parameters. Staining of the cells with acridine orange following incubation with 3-Cl-AHPC revealed intact plasma membrane but nuclear fragmentation characteristics associated with apoptosis. Apoptosis was further documented by end-labeling of DNA fragments. Flow cytometry demonstrated that over 80 percent of patient leukemic cells underwent apoptosis.

3-Cl-AHPC Induction of Apoptosis of Cancer Cells.

Figure 11:
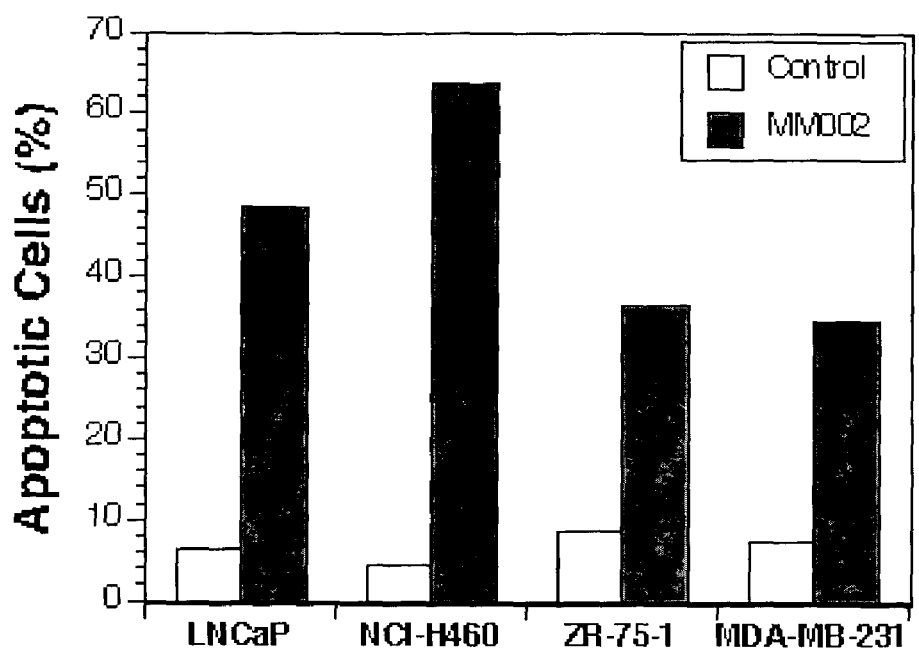
FIGS. 11 and 12 illustrate the induction of apoptosis of various cancer cells after treatment with 3-Cl-AHPC.
Figure 12:
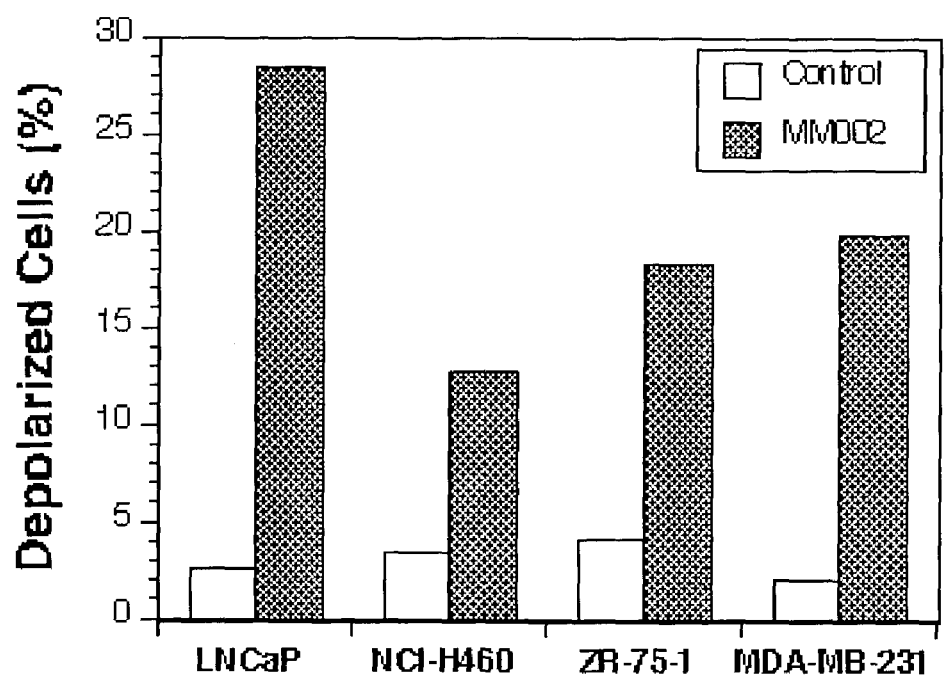

4,6-Diamidino-2-phenylindole (DAPI) staining was used to study the apoptotic effect of 3-Cl-AHPC in various cancer cell lines, including prostate cancer LNCaP, lung cancer NCI-H460, and breast cancer ZR-75-1 and MDA-MB231 cells. The results demonstrate that 3-Cl-AHPC potently induced apoptosis of these cancer cell lines (FIG. 11). A well-established apoptotic pathway involves mitochondria. Cytochrome c is exclusively present in mitochondria and is released from mitochondria in response to various apoptotic stimuli. To determine whether 3-Cl-AHPC-induced apoptosis involved regulation of mitochondrial function, its effect on mitochondrial membrane potential ($\Delta\psi$m) was investigated using Rh123. 3-Cl-AHPC induced significant increases in the percentage of cells with $\Delta\psi$m loss (FIG. 12). Thus, 3-Cl-AHPC-induced apoptosis of cancer cells is partly mediated through disruption of $\Delta\psi$m.

In FIG. 11, the indicated cancer cells were treated with $10^{-6}$ M 3-Cl-AHPC, trypsinized, washed with PBS, fixed with 3.7% paraformaldehyde, and stained with 50 µg/ml DAPI containing 100 µg/ml DNase-free RNase A to visualize nuclei by fluorescent microscopy. The number of apoptotic cells with nuclear morphology typical of apoptosis, including nuclear fragmentation and condensation, was scored in at least 400 cells in each sample using a fluorescence microscope. In FIG. 12, the indicated cancer cells were treated with $10^{-6}$ M 3-Cl-AHPC, trypsinized, washed with PBS, fixed with 3.7% paraformaldehyde, and stained with 50 µg/ml DAPI containing 100 µg/ml DNase-free RNase A to visualize nuclei and examined by fluorescent microscopy. Number of apoptotic cells with nuclear morphology typical of apoptosis, including nuclear fragmentation and condensation, was scored in at least 400 cells in each sample using a fluorescence microscope.

In Vitro Efficacy of 3-Cl-AHPC Against Breast Carcinoma Cells

The ability of 3-Cl-AHPC to induce cell death in a number of breast carcinoma cells is documented in Table 3, which presents the concentration of either tRA or 3-Cl-AHPC that results in 50% cell death ($ED_{50}$). The results demonstrate that 3-Cl-AHPC is more active in killing the breast carcinoma cells than tRA. Low concentrations of 3-Cl-AHPC are capable of killing the breast carcinoma cells while even concentrations of 10 µM tRA did not kill the cells. As further documented in Table 3, 3-Cl-AHPC induced cell death in a variety of breast carcinoma cell lines (MDA-MD-231, MDA-MB-468), which are totally resistant to tRA-mediated inhibition of growth.

TABLE 3

Effects of trans-RA and 3-Cl-AHPC on Apoptosis Induction in Human Breast Cancer Cells
$ED_{50}$ (µM)

| Cell Type | Trans-RA* | 3-Cl-AHPC |
|---|---|---|
| MCF-7 | >10 | 0.85 |
| T47-D | >10 | 0.91 |
| ZR-75 | >10 | 0.70 |

TABLE 3-continued

Effects of trans-RA and 3-Cl-AHPC on Apoptosis Induction in Human Breast Cancer Cells
$ED_{50}$ (µM)

| Cell Type | Trans-RA* | 3-Cl-AHPC |
|---|---|---|
| MDA-MB-231 | >10 | 0.65 |
| MDA-MB-468 | >10 | 0.71 |

*<5% apoptosis

In Vitro Efficacy of 3-Cl-AHPC Against Primary Cultures of Human Acute Myeloid Leukemia Cells.

Figure 13:
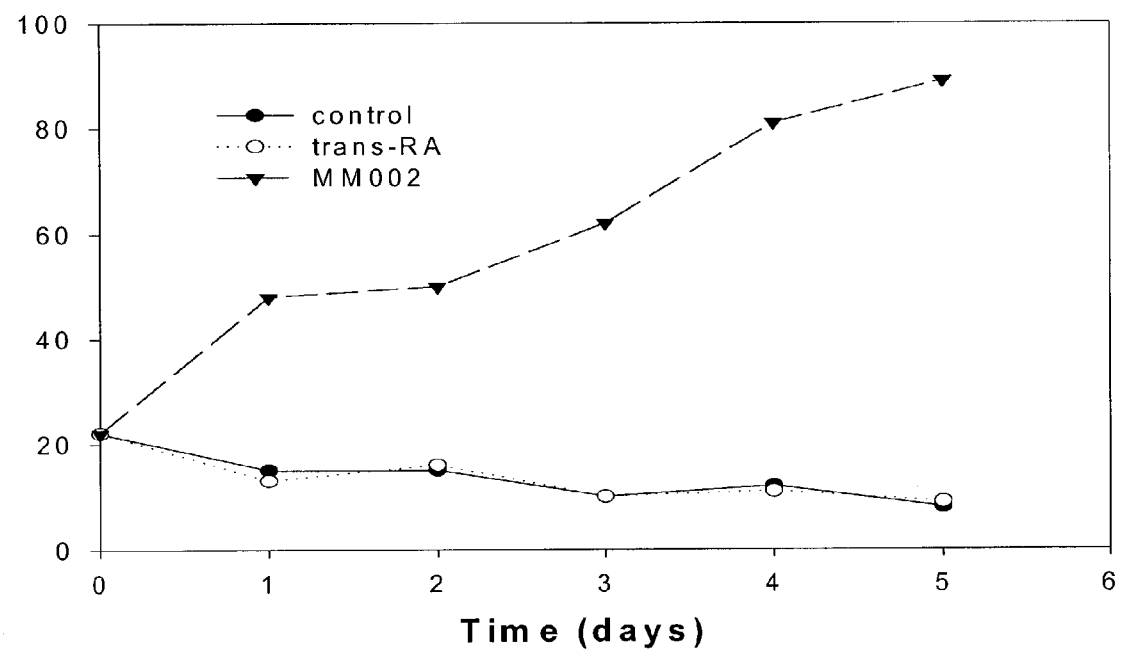
FIG. 13 illustrates the induction of cell death (apoptosis) in human primary acute myelogenous leukemia (AML) cells after treatment with tRA and 3-Cl-AHPC.

3-Cl-AHPC induced cell death (apoptosis) in primary cultures of human acute myeloid leukemia cells (AML) obtained from patients. These human AML cells are resistant to tRA (FIG. 13). None of the leukemias were acute promyelocytic leukemia but other types of AML which are known to be resistant to the differentiating and anti-proliferative effects of classical retinoids. As illustrated in FIG. 13, 3-Cl-AHPC inhibited the proliferation and induced apoptosis in these leukemia cell samples whereas tRA had no effect.

3-Cl-AHPC Inhibits the In Vivo Growth of Breast Cancer

The ability of 3-Cl-AHPC to inhibit the in vivo growth of breast carcinoma cells was tested using syngeneic mouse mammary and human breast adenocarcinoma SCID xenograft models. The ability of 3-Cl-AHPC to inhibit the growth of the mouse mammary adenocarcinoma 16/C in female C3H mice is shown in Table 4. Compared to AHPN, 3-Cl-AHPC induced minimal toxicity as evidenced by weight loss of the mice and it inhibited tumor growth by 80% (T/C=20% where T is the volume of the tumor in the treated group and C is the volume of the tumor in the control group).

AHPN and 3-Cl-AHPC Inhibition of Murine Mammary Adenocarcinoma 16/c in Syngeneic Mice

| Treatment | Schedule (days) | Total Dose (mg/kg) | % body wt loss | Drug deaths | T/C % | Log cell kill |
|---|---|---|---|---|---|---|
| None |  |  | −4 |  | 0/5 |  |
| AHPN | 1, 2, 7–9 | 150 | −21 | 1/5 | 30 | 0.63 |
|  | 1, 2, 5–9 | 133 | −11 | 0/5 | 39 | 0.49 |
|  | 1–9 | 99 | −4 | 0/5 | 47 |  |
| 3-Cl-AHPC | 1–4, 6,8 | 178 | −4 | 0/5 | 20 | 0.9 |
|  | 1–4, 6–8 | 89 | −3 | 0/5 | 47 |  |
|  | 1–4, 6–8 | 44 | 4 | 0/5 | >100 |  |

In addition, 3-Cl-AHPC treatment of SCID mice implanted with human MX-1 breast adenocarcinoma cells resulted in a 70% inhibition of tumor growth with minimal animal toxicity (no animal deaths and weight loss less than 4%) (Table 5). Thus, 3-Cl-AHPC fits the National Cancer Institute definition of a compound with anti-neoplastic activity.

TABLE 5

3-Cl-AHPC Inhibition of MX-1 Human Mammary Adenocarcinoma Growth in SCID Mice.

| Treatment | Schedule (days) | Total Dose (mg/kg) | % body wt loss | Drug deaths | T/C % | Log cell kill |
|---|---|---|---|---|---|---|
| None | | | | 2 | 0/5 | |
| 3-Cl-AHPC | Qd (3–9) | 210 | −4 | 0/5 | 30 | 1.2 |
| | Qd (3–9) | 140 | −4 | 0/5 | 56 | |
| | Qd (3–9) | 91 | −2 | 0/5 | 62 | |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound having formula (I):

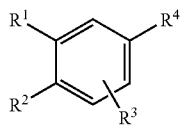

(I)

wherein $R^1$ is adamantyl, bicyclooctyl, bicyclooctenyl, aza-bicyclooctyl, or aza-bicyclooctenyl;
wherein the $R^1$ groups are optionally substituted with one or more $C_{1-10}$alkyl groups;
$R^2$ is hydroxy, —SH, amino, —CN, $(C_{1-10}$alkyl)NH—, $(C_{1-10}$alkyl)$_2$N—, —COOR$^{14}$, —C(=O)R$^{14}$, —C(=O)N(R$^{14}$)$_2$, —N(R$^{14}$)C(=O)R$^{14}$, —P(O)(OR$^{14}$)$_2$(phosphonic acid), —S(O)$_2$OR$^{14}$(sulfonic acid), —S(O)$_2$N(R$^{14}$)$_2$(sulfonamide), —N—C(NH)—N(R$^{14}$)$_2$(guanidino), (hydroxy)$C_{1-10}$alkylene-, $(C_{1-10}$alkyl)-C(O)—, —C(O)—NHOR$^{14}$(hydroxamic acid), or oxime;
$R^3$ hydrogen, $C_{1-10}$alkyl, hydroxy, amino, $(C_{1-10}$alkyl)NH—, $(C_{1-10}$alkyl)$_2$N—, —COOR$^{14}$(carboxylic acid), —P(O)(OR$^{14}$)$_2$(phosphonic acid), —S(O)$_2$OR$^{14}$(sulfonic acid), —S(O)$_2$N(R$^{14}$)$_2$(sulfonamide), —N—C(NH)—N(R$^{15}$)$_2$(guanidino), (hydroxy)$C_{1-10}$alkylene, $(C_{1-10}$alkyl)—C(O)—, —C(O)—NHOR$^{14}$(hydroxamic acid), carbonyl oxime, fluoro, chloro, bromo, iodo, —CF$_3$ or nitro; or $R^1$ and $R^3$ taken together with the ring to which they are attached can form a polycyclic group which can be fully saturated, partially saturated or aromatic;
$R^4$ is

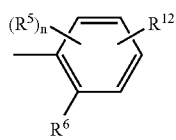

wherein each $R^5$ is independently hydroxy, $C_{1-10}$alkyl, $C_{1-10}$alkoxy, amino, $(C_{1-10}$alkyl)NH—, $(C_{1-10}$alkyl)$_2$N—, (amino)$C_{1-10}$alkyleneoxy)—, (acetamido) alkoxy, $(C_{1-10})$mercapto, (hydroxy)$C_{1-10}$alkylene-, halo, halo($C_{1-10}$)alkyl, $(C_{1-10}$alkoxy)-$C_{1-10}$alkylene-, nitro, acetamido, phenyl, or substituted phenyl;
$R^6$ is hydrogen, hydroxy, $C_{1-10}$alkyl, $C_{1-10}$alkoxy, amino, $(C_{1-10}$alkyl)NH—, $(C_{1-10}$alkyl)$_2$N—, (amino)$C_{1-10}$alkyleneoxy)-, (acetamido)alkoxy, $(C_{1-10}$alkyl)mercapto, (hydroxy)$C_{1-10}$alkylene-, halo, halo($C_{1-10}$)alkyl, $(C_{1-10}$alkoxy)$C_{1-10}$alkylene-, nitro, acetamido, phenyl, or substituted phenyl;
$R^9$ is —COOR$^{14}$, —P(O)(OR$^{14}$)$_2$, —S(O)$_2$OR$^{14}$, —C(O)—NHOR$^{14}$, thiazolidenedione, tropolone, tetrazole, nitro, —(CH$_2$)$_j$OR$^{15}$, or —N—C(NH)—N(R$^{15}$)$_2$;
$R^{12}$ is —C(R$^{16}$)=C(R$^{16}$)(R$^9$), aryl-R$^9$, or 2-cyclopropyl-R$^9$, where each $R^{16}$ is independently hydrogen or fluorine;
$R^{14}$ is hydrogen, $(C_{1-25})$alkyl or aryl;
$R^{15}$ is hydrogen, $(C_{1-10}$alkyl)—C(O)—, or (aryl)-C(O)—;
j is from 1 to 10; and is 0, 1, 2, or 3;
wherein any alkyl, alkenyl, alkynyl, cycloalkyl, cycloalkenyl, polycyclo alkyl, polycycloalkenyl, heterocycloalkyl, polyheterocycloalkyl, heterocycloalkenyl, polyheterocycloalkenyl, aryl, or heteroaryl group of $R^1$, $R^2$, $R^3$, $R^5$, and $R^6$ is optionally substituted with one or more, such as 1, 2, 3, or 4, substituents independently selected from oxo(=O), halo, —OH, —CN, —NO$_2$, —CF$_3$, —OCF$_3$, —S(O)$_{0-2}$C$_{1-6}$ alkyl, $C_{1-8}$alkyl, $C_{1-8}$alkoxy, $C_{1-8}$alkyl-NR$_a$R$_b$, phenyl, $C_{1-8}$alkanoyl, —NR$_a$R$_b$, —C(=O)NR$_a$R$_b$, or —SO$_2$NNR$_a$R$_b$;
wherein each R$_a$ and R$_b$ is independently hydrogen, $C_{1-6}$alkyl, $C_{1-6}$alkanoyl, $C_{1-6}$alkoxycarbonyl, aryl, (aryl)($C_{1-8}$alkylene-, arylcarbonyl, or aryloxycarbonyl; or R$_a$ and R$_b$ together with the nitrogen to which they are attached form a pyrrolidino, piperidino, morpholino, or thiomorpholino ring; or
a pharmaceutical acceptable salt thereof.

2. The compound of claim 1 wherein $R^1$ adamantyl.

3. The compound of claim 1 wherein $R^2$ is hydroxy, —COOR$^{14}$, —C(=O)CH$_3$, or —SH.

4. The compound of claim 3 wherein $R^2$ is hydroxy.

5. The compound of claim 1 wherein $R^3$ is hydrogen, methyl, ethyl, chloro, bromo, fluoro, or —CF$_3$.

6. The compound of claim 5 wherein $R^3$ is hydrogen, or methyl.

7. The compound of claim 1 wherein $R^4$ is

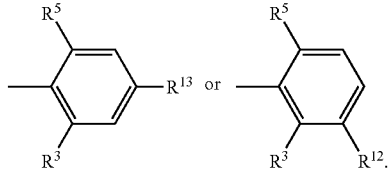

8. The compound of claim 7 wherein $R^5$ and $R^6$ are independently hydrogen, methyl, ethyl, methoxy, ethoxy, chloro, bromo, fluoro, —CF$_3$, —O—(CH$_2$)$_3$—NH$_2$, or —O—(CH$_2$)$_3$—NH—C(=O)CH$_3$.

9. The compound of claim 8 wherein $R^5$ and $R^6$ are independently hydrogen, methyl, methoxy, ethoxy, chloro, bromo, fluoro, —CF$_3$, —O—(CH$_2$)$_3$—NH$_2$ or —O—(CH$_2$)$_3$—NH—C(=O)CH$_3$.

10. The compound of claim 9 wherein $R^5$ and $R^6$ are independently hydrogen, methyl, chloro, bromo, or fluoro, —CF$_3$, —O—(CH$_2$)$_3$—NH$_2$ or —O—(CH$_2$)$_3$—NH—C(=O)CH$_3$.

11. The compound of claim 10 wherein one of $R^5$ and $R^6$ is hydrogen and the other is methyl, chloro, bromo, —$CF_3$, —O—$(CH_2)_3$—$NH_2$, or —O—$(CH_2)_3$—NH—C(=O)$CH_3$.

12. The compound of claim 1 wherein $R^9$ is —$COOR^{14}$, —P(O)$(OR^{14})_2$, —S(O)$_2OR^{14}$, or —C(O)—$NHOR^{14}$.

13. The compound of claim 12 wherein $R^9$ is —$COOR^{14}$.

14. The compound of claim 1 wherein $R^{12}$ is —C(H)=C(H)($R^9$), or aryl-$R^9$.

15. The compound of claim 1 wherein having the formula (II):

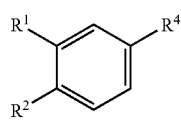

wherein $R^2$ is —OH, $R^4$ is

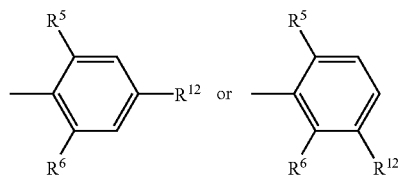

$R^{12}$ is —C(H)=C(H)—C(=O)$OR^{14}$ where $R^{14}$ is hydrogen or ethyl; and $R^5$ and $R^6$ are independently hydrogen, methyl, methoxy, chloro, or fluoro.

16. The compound of claim 15 wherein $R^{12}$ is the E-isomer.

17. The compound of claim 1 wherein $R^3$ is —$CF_3$.

18. The compound of claim 15 having the formula:

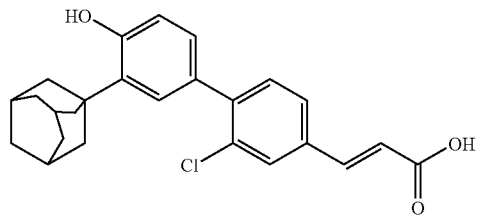

or a pharmaceutically acceptable salt thereof.

19. The compound of claim 15 having the formula:

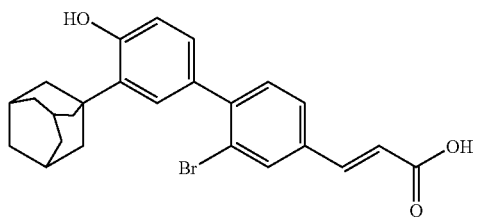

or a pharmaceutically acceptable salt thereof.

20. The compound of claim 15 having the formula:

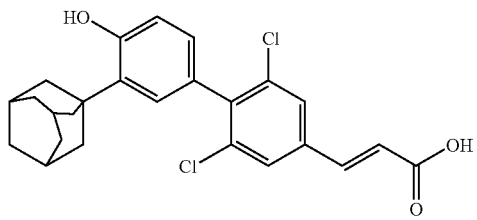

or a pharmaceutically acceptable salt thereof.

21. The compound of claim 15 having the formula:

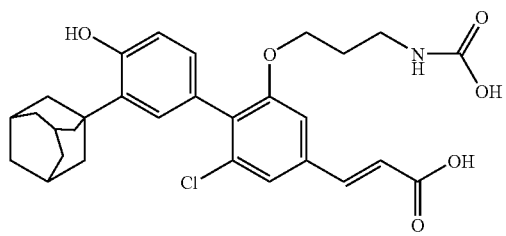

or a pharmaceutically acceptable salt thereof.

22. A method of treating cancer in a mammal comprising contacting the cancer cells with a compound of claim 1, effective to reduce the viability of the cancerous cells, wherein the cancer is lung cancer, breast cancer, prostate cancer, or leukemia.

23. The method of claim 22 wherein the leukemia is acute lymphocytic leukemia, acute myelogenous leukemia, or chronic myelogenous leukemia.

24. A method for inducing apoptosis, inducing caspase activity, or inducing cell death in a mammal comprising contacting target cells with a compound of claim 1, effective to induce apoptosis, induce caspase activity, or induce cell death the target cells, wherein the target cells are lung cancer, breast cancer, prostate cancer, or leukemia cells.

* * * * *